United States Patent
Kobold et al.

(10) Patent No.: US 11,192,935 B2
(45) Date of Patent: Dec. 7, 2021

(54) PD-1-CD28 FUSION PROTEINS AND THEIR USE IN MEDICINE

(71) Applicants: Sebastian Kobold, Munich (DE); Stefan Endres, Munich (DE)

(72) Inventors: Sebastian Kobold, Munich (DE); Stefan Endres, Munich (DE)

( * ) Notice: Subject to any disclaimer, the term of this patent is extended or adjusted under 35 U.S.C. 154(b) by 439 days.

(21) Appl. No.: 15/737,877

(22) PCT Filed: Jun. 20, 2016

(86) PCT No.: PCT/EP2016/064195
§ 371 (c)(1),
(2) Date: Dec. 19, 2017

(87) PCT Pub. No.: WO2016/203048
PCT Pub. Date: Dec. 22, 2016

(65) Prior Publication Data
US 2019/0010207 A1    Jan. 10, 2019

(30) Foreign Application Priority Data

Jun. 19, 2015 (EP) ..................................... 15172913

(51) Int. Cl.
| C07K 14/705 | (2006.01) |
| A61P 35/00 | (2006.01) |
| C12N 15/62 | (2006.01) |
| C12N 15/85 | (2006.01) |

(52) U.S. Cl.
CPC ........ *C07K 14/70521* (2013.01); *A61P 35/00* (2018.01); *C07K 14/70503* (2013.01); *C12N 15/62* (2013.01); *C12N 15/85* (2013.01); *C07K 2319/00* (2013.01); *C07K 2319/03* (2013.01)

(58) Field of Classification Search
None
See application file for complete search history.

(56) References Cited

U.S. PATENT DOCUMENTS

2014/0242049 A1   8/2014   Kyungho

FOREIGN PATENT DOCUMENTS

| WO | 2013019615 A2 | 2/2013 |
| WO | 2013062365 A2 | 5/2013 |

OTHER PUBLICATIONS

International Search Report and Written Opinion to corresponding International Application No. PCT/EP2016/064195 dated Oct. 5, 2016 (16 pages).
Shen et al., "Human T Cells Engineered to Express a Programmed Death 1/28 Costimulatory Retargeting Molecule Display Enhanced Antitumor Activity," Journal of Immunology, vol. 191, No. 8, pp. 4121-4129 (2013).
Kobold et al., "P68. A new EGFR-EpCAM bispecific antibody enhances the efficacy of adoptive T-cell therapy in a murine gastric tumour model," Journal for Immunotherapy of Cancer Biomed Central Ltd., London, UK, vol. 2, No. Suppl 2, pp. P42 (2014).
Kobold et al., "Impact of a New Fusion Receptor on PD-1-Mediated Immunosuppression in Adoptive T Cell Therapy,"Journal of the National Cancer Institute, vol. 107, No. 8 (2015).
Prosser et al., "Tumor PD-L1 co-stimulates primary human CD8cytotoxic T cells modified to express a PD1:CD28 chimeric receptor," Molecular Immunology, Pergamon, GB, vol. 51, No. 3, pp. 263-272 (2012).
Shin et al., "Positive conversion of negative signaling of CTLA4 potentiates antitumor efficacy of adoptive T-cell therapy in murine tumor models," Blood, vol. 119, No. 24, pp. 5678-5687 (2012).
Tang, et al., "The advantages of PD1 activating chimeric receptor (PD1-ACR) engineered lymphocytes for PDL1(+) cancer therapy," American Journal of Translational Research, vol. 7, No. 3, pp. 460-473 (2015).
International Preliminary Report on Patentability and Written Opinion to corresponding International Application No. PCT/EP2016/064195 dated Dec. 28, 2017 (18 pages).

*Primary Examiner* — Brad Duffy
(74) *Attorney, Agent, or Firm* — Wolf, Greenfield & Sacks, P.C.

(57) ABSTRACT

The present invention relates to PD-1-CD28 fusion proteins, nucleic acid molecules, vectors, transduced cells carrying nucleic acid molecules or vectors of the present invention or expressing the fusion proteins of the present invention, methods and kits comprising the nucleic acid molecules, vectors and/or the fusion proteins of the present invention. The invention also provides the use of said transduced cells in a method for the treatment of particular diseases as well as a pharmaceutical composition/medicament comprising said transduced cells expressing the fusion proteins of the present invention for use in a method of treating of diseases, in particular in the medical intervention of diseases characterized by PD-L1 and/or PD-L2 expression.

11 Claims, 31 Drawing Sheets
Specification includes a Sequence Listing.

Figure 2:
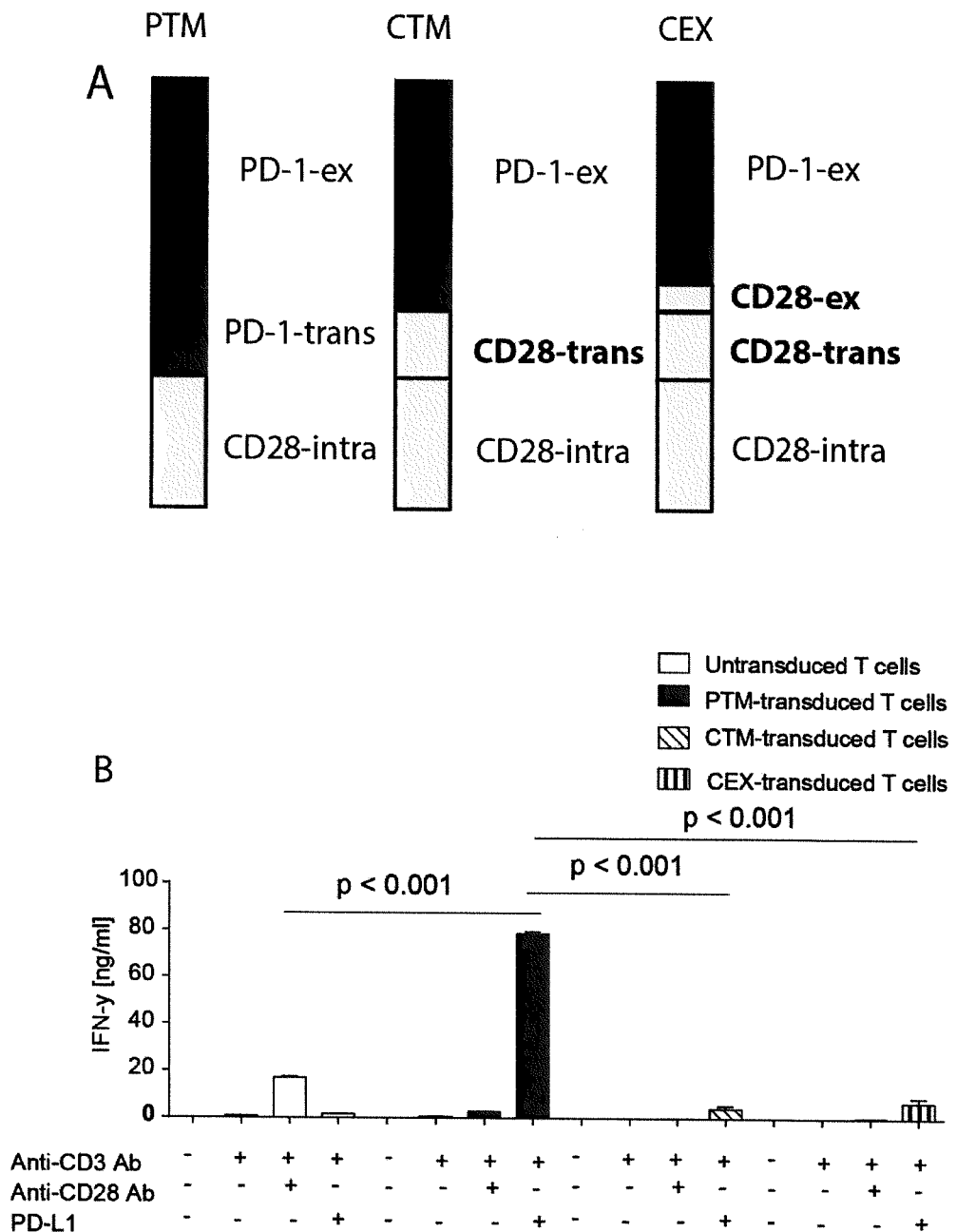
Figure 2:
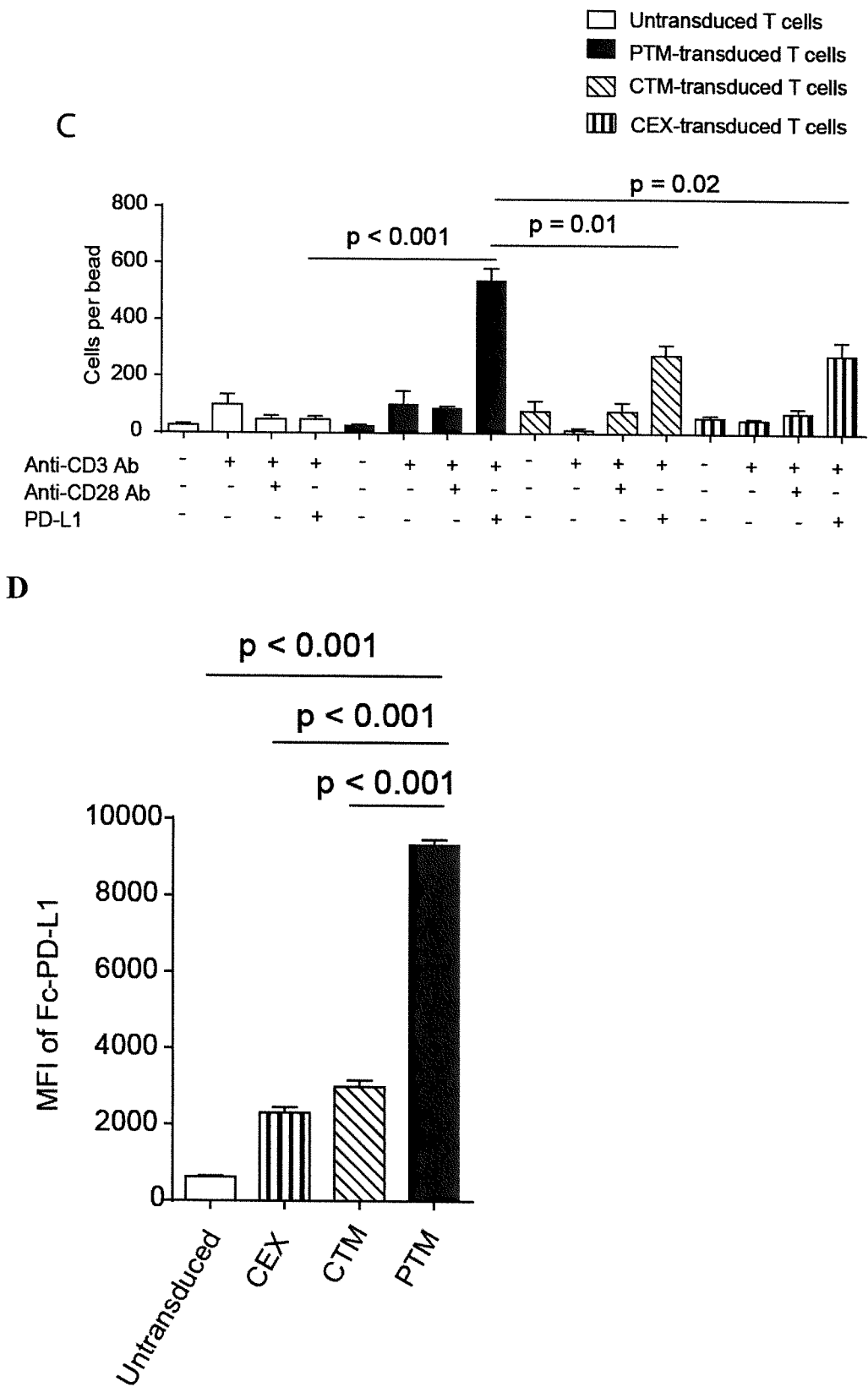
Figure 3:
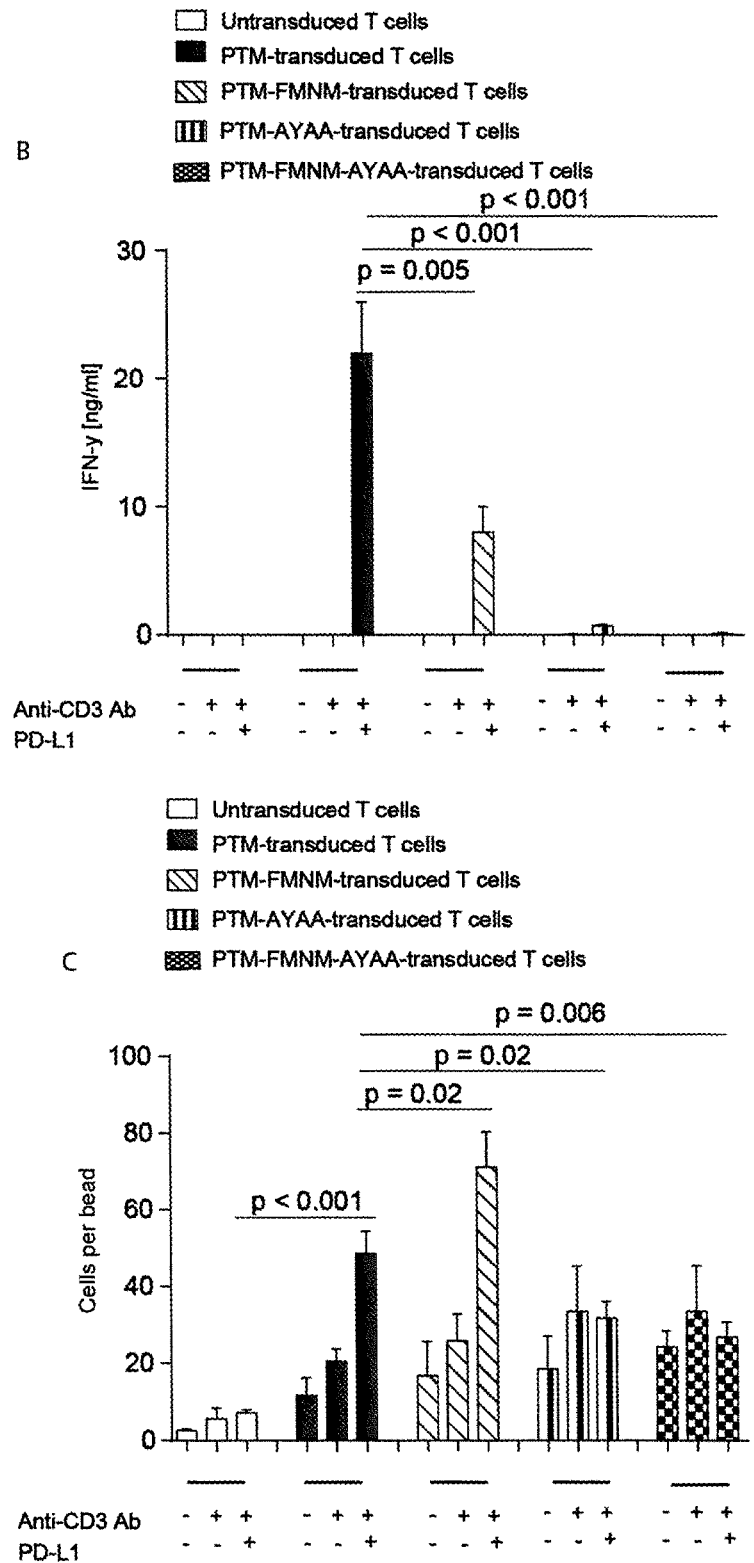
Figure 3:
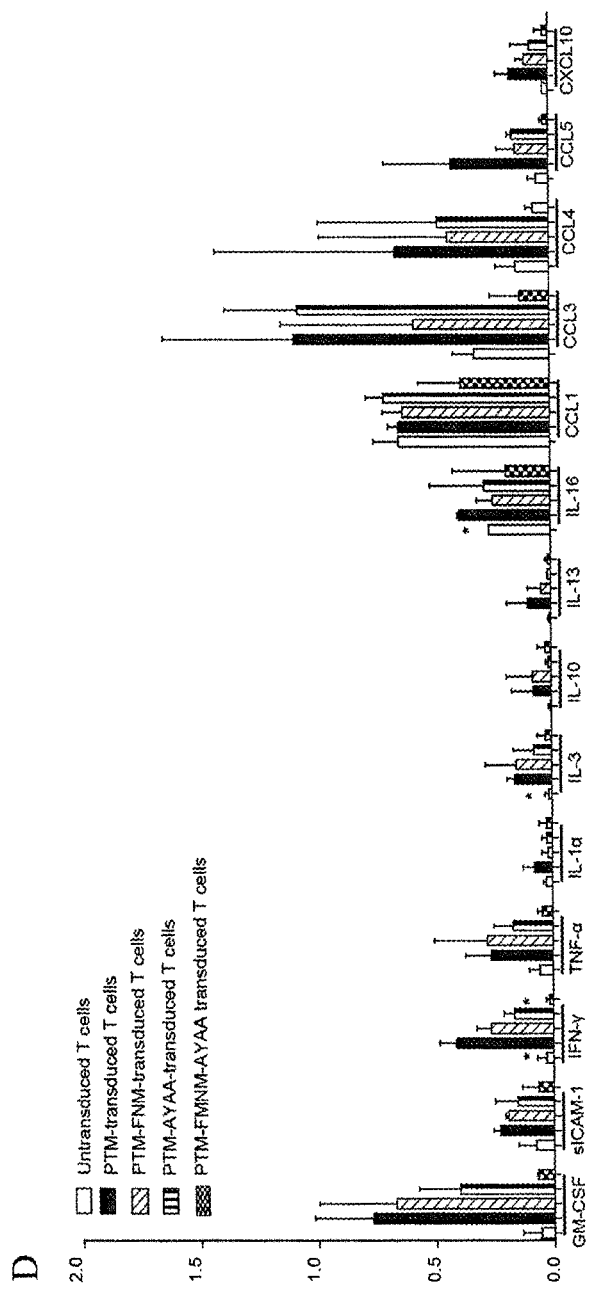

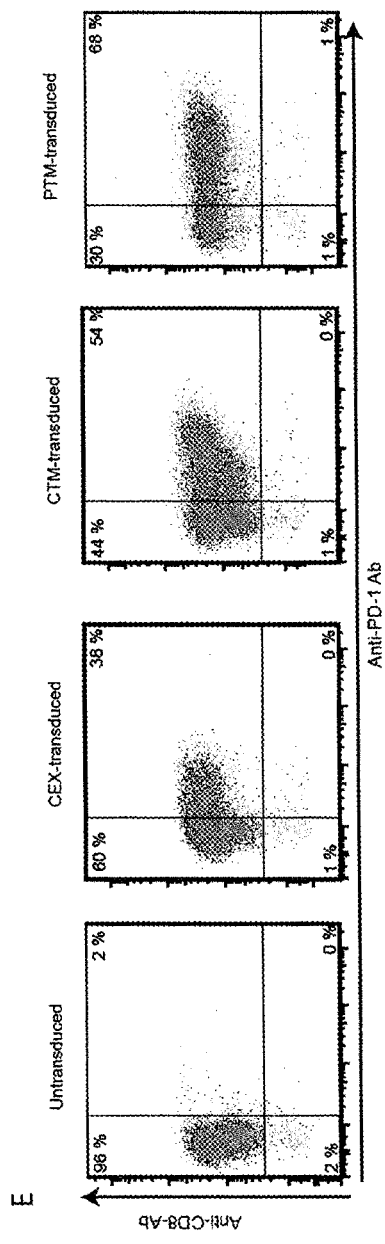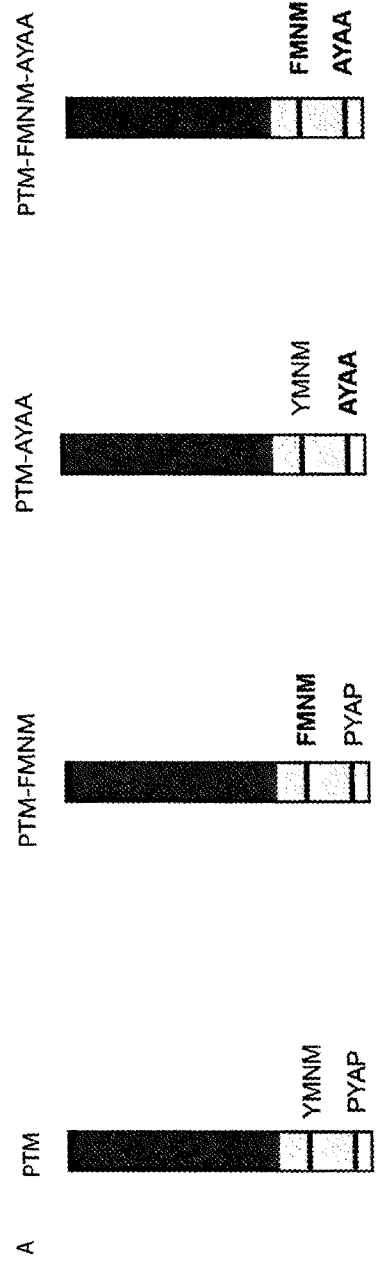
Figure 2 (continued)
Figure 3

B

C

A

B

C

D

E

A

B

C

D

E

A

B

E

F

A

B

SEQUENCE LISTING

<160> NUMBER OF SEQ ID NOS: 65

<210> SEQ ID NO 1
<211> LENGTH: 864
<212> TYPE: DNA
<213> ORGANISM: Artificial Sequence
<220> FEATURE:
<221> NAME/KEY: source
<222> LOCATION: 1..864
<223> OTHER INFORMATION: /mol_type="unassigned DNA"
    /note="murine full-length PD-1"
    /organism="Artificial Sequence"
<220> FEATURE:
<221> NAME/KEY: CDS
<222> LOCATION: 1..864
<223> OTHER INFORMATION: /transl_table=1

<400> SEQUENCE: 1

| | | | | | | | | | | | | | | | | |
|---|---|---|---|---|---|---|---|---|---|---|---|---|---|---|---|---|
| atg | tgg | gtg | cgc | cag | gtg | ccg | tgg | agc | ttt | acc | tgg | gcg | gtg | ctg | cag | 48 |
| Met | Trp | Val | Arg | Gln | Val | Pro | Trp | Ser | Phe | Thr | Trp | Ala | Val | Leu | Gln | |
| 1 | | | | 5 | | | | | 10 | | | | | 15 | | |

| ctg | agc | tgg | cag | agc | ggc | tgg | ctg | ctg | gaa | gtg | ccg | aac | ggc | ccg | tgg | 96 |
|---|---|---|---|---|---|---|---|---|---|---|---|---|---|---|---|---|
| Leu | Ser | Trp | Gln | Ser | Gly | Trp | Leu | Leu | Glu | Val | Pro | Asn | Gly | Pro | Trp | |
| | | | 20 | | | | | 25 | | | | | 30 | | | |

| cgc | agc | ctg | acc | ttt | tat | ccg | gcg | tgg | ctg | acc | gtg | agc | gaa | ggc | gcg | 144 |
|---|---|---|---|---|---|---|---|---|---|---|---|---|---|---|---|---|
| Arg | Ser | Leu | Thr | Phe | Tyr | Pro | Ala | Trp | Leu | Thr | Val | Ser | Glu | Gly | Ala | |
| | | | 35 | | | | | 40 | | | | | 45 | | | |

| aac | gcg | acc | ttt | acc | tgc | agc | ctg | agc | aac | tgg | agc | gaa | gat | ctg | atg | 192 |
|---|---|---|---|---|---|---|---|---|---|---|---|---|---|---|---|---|
| Asn | Ala | Thr | Phe | Thr | Cys | Ser | Leu | Ser | Asn | Trp | Ser | Glu | Asp | Leu | Met | |
| | 50 | | | | | 55 | | | | | 60 | | | | | |

| ctg | aac | tgg | aac | cgc | ctg | agc | ccg | agc | aac | cag | acc | gaa | aaa | cag | gcg | 240 |
|---|---|---|---|---|---|---|---|---|---|---|---|---|---|---|---|---|
| Leu | Asn | Trp | Asn | Arg | Leu | Ser | Pro | Ser | Asn | Gln | Thr | Glu | Lys | Gln | Ala | |
| 65 | | | | | 70 | | | | | 75 | | | | | 80 | |

| gcg | ttt | tgc | aac | ggc | ctg | agc | cag | ccg | gtg | cag | gat | gcg | cgc | ttt | cag | 288 |
|---|---|---|---|---|---|---|---|---|---|---|---|---|---|---|---|---|
| Ala | Phe | Cys | Asn | Gly | Leu | Ser | Gln | Pro | Val | Gln | Asp | Ala | Arg | Phe | Gln | |
| | | | | 85 | | | | | 90 | | | | | 95 | | |

| att | att | cag | ctg | ccg | aac | cgc | cat | gat | ttt | cat | atg | aac | att | ctg | gat | 336 |
|---|---|---|---|---|---|---|---|---|---|---|---|---|---|---|---|---|
| Ile | Ile | Gln | Leu | Pro | Asn | Arg | His | Asp | Phe | His | Met | Asn | Ile | Leu | Asp | |
| | | | 100 | | | | | 105 | | | | | 110 | | | |

| acc | cgc | cgc | aac | gat | agc | ggc | att | tat | ctg | tgc | ggc | gcg | att | agc | ctg | 384 |
|---|---|---|---|---|---|---|---|---|---|---|---|---|---|---|---|---|
| Thr | Arg | Arg | Asn | Asp | Ser | Gly | Ile | Tyr | Leu | Cys | Gly | Ala | Ile | Ser | Leu | |
| | | 115 | | | | | 120 | | | | | 125 | | | | |

| cat | ccg | aaa | gcg | aaa | att | gaa | gaa | agc | ccg | ggc | gcg | gaa | ctg | gtg | gtg | 432 |
|---|---|---|---|---|---|---|---|---|---|---|---|---|---|---|---|---|
| His | Pro | Lys | Ala | Lys | Ile | Glu | Glu | Ser | Pro | Gly | Ala | Glu | Leu | Val | Val | |
| | | 130 | | | | | 135 | | | | | 140 | | | | |

| acc | gaa | cgc | att | ctg | gaa | acc | agc | acc | cgc | tat | ccg | agc | ccg | agc | ccg | 480 |
|---|---|---|---|---|---|---|---|---|---|---|---|---|---|---|---|---|
| Thr | Glu | Arg | Ile | Leu | Glu | Thr | Ser | Thr | Arg | Tyr | Pro | Ser | Pro | Ser | Pro | |
| 145 | | | | | 150 | | | | | 155 | | | | | 160 | |

| aaa | ccg | gaa | ggc | cgc | ttt | cag | ggc | atg | gtg | att | ggc | att | atg | agc | gcg | 528 |
|---|---|---|---|---|---|---|---|---|---|---|---|---|---|---|---|---|
| Lys | Pro | Glu | Gly | Arg | Phe | Gln | Gly | Met | Val | Ile | Gly | Ile | Met | Ser | Ala | |
| | | | | 165 | | | | | 170 | | | | | 175 | | |

| ctg | gtg | ggc | att | ccg | gtg | ctg | ctg | ctg | gcg | tgg | gcg | ctg | gcg | gtg | | 576 |
|---|---|---|---|---|---|---|---|---|---|---|---|---|---|---|---|---|
| Leu | Val | Gly | Ile | Pro | Val | Leu | Leu | Leu | Ala | Trp | Ala | Leu | Ala | Val | | |
| | | | 180 | | | | | 185 | | | | | 190 | | | |

| ttt | tgc | agc | acc | agc | atg | agc | gaa | gcg | cgc | ggc | gcg | ggc | agc | aaa | gat | 624 |
|---|---|---|---|---|---|---|---|---|---|---|---|---|---|---|---|---|
| Phe | Cys | Ser | Thr | Ser | Met | Ser | Glu | Ala | Arg | Gly | Ala | Gly | Ser | Lys | Asp | |
| | | | 195 | | | | | 200 | | | | | 205 | | | |

| gat | acc | ctg | aaa | gaa | gaa | ccg | agc | gcg | gcg | ccg | gtg | ccg | agc | gtg | gcg | 672 |
|---|---|---|---|---|---|---|---|---|---|---|---|---|---|---|---|---|
| Asp | Thr | Leu | Lys | Glu | Glu | Pro | Ser | Ala | Ala | Pro | Val | Pro | Ser | Val | Ala | |
| | | 210 | | | | | 215 | | | | | 220 | | | | |

| tat | gaa | gaa | ctg | gat | ttt | cag | ggc | cgc | gaa | aaa | acc | ccg | gaa | ctg | ccg | 720 |
|---|---|---|---|---|---|---|---|---|---|---|---|---|---|---|---|---|
| Tyr | Glu | Glu | Leu | Asp | Phe | Gln | Gly | Arg | Glu | Lys | Thr | Pro | Glu | Leu | Pro | |
| 225 | | | | | 230 | | | | | 235 | | | | | 240 | |

```
acc gcg tgc gtg cat acc gaa tat gcg acc att gtg ttt acc gaa ggc    768
Thr Ala Cys Val His Thr Glu Tyr Ala Thr Ile Val Phe Thr Glu Gly
            245                 250                 255 ctg ggc gcg agc gcg atg ggc cgc cgc ggc agc gcg gat ggc ctg cag    816
Leu Gly Ala Ser Ala Met Gly Arg Arg Gly Ser Ala Asp Gly Leu Gln
        260                 265                 270 ggc ccg cgc ccg ccg cgc cat gaa gat ggc cat tgc agc tgg ccg ctg    864
Gly Pro Arg Pro Pro Arg His Glu Asp Gly His Cys Ser Trp Pro Leu
    275                 280                 285

<210> SEQ ID NO 2
<211> LENGTH: 288
<212> TYPE: PRT
<213> ORGANISM: Artificial Sequence
<220> FEATURE:
<223> OTHER INFORMATION: [CDS]:1..864 from SEQ ID NO 1

<400> SEQUENCE: 2
```

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
                165                 170                 175

Leu Val Gly Ile Pro Val Leu Leu Leu Leu Ala Trp Ala Leu Ala Val
            180                 185                 190

Phe Cys Ser Thr Ser Met Ser Glu Ala Arg Gly Ala Gly Ser Lys Asp
        195                 200                 205

Asp Thr Leu Lys Glu Glu Pro Ser Ala Ala Pro Val Pro Ser Val Ala
    210                 215                 220

Tyr Glu Glu Leu Asp Phe Gln Gly Arg Glu Lys Thr Pro Glu Leu Pro
225                 230                 235                 240

Thr Ala Cys Val His Thr Glu Tyr Ala Thr Ile Val Phe Thr Glu Gly
                245                 250                 255

Leu Gly Ala Ser Ala Met Gly Arg Arg Gly Ser Ala Asp Gly Leu Gln
            260                 265                 270

Gly Pro Arg Pro Pro Arg His Glu Asp Gly His Cys Ser Trp Pro Leu
        275                 280                 285

```
<210> SEQ ID NO 3
```

```
<211> LENGTH: 864
<212> TYPE: DNA
<213> ORGANISM: Artificial Sequence
<220> FEATURE:
<221> NAME/KEY: source
<222> LOCATION: 1..864
<223> OTHER INFORMATION: /mol_type="unassigned DNA"
      /note="human full-length PD-1"
      /organism="Artificial Sequence"
<220> FEATURE:
<221> NAME/KEY: CDS
<222> LOCATION: 1..864
<223> OTHER INFORMATION: /transl_table=1

<400> SEQUENCE: 3
```

| | | | | | | | | | | | | | | | | |
|---|---|---|---|---|---|---|---|---|---|---|---|---|---|---|---|---|
| atg | cag | att | ccg | cag | gcg | ccg | tgg | ccg | gtg | gtg | tgg | gcg | gtg | ctg | cag | 48 |
| Met | Gln | Ile | Pro | Gln | Ala | Pro | Trp | Pro | Val | Val | Trp | Ala | Val | Leu | Gln | |
| 1 | | | | 5 | | | | | 10 | | | | | 15 | | |
| ctg | ggc | tgg | cgc | ccg | ggc | tgg | ttt | ctg | gat | agc | ccg | gat | cgc | ccg | tgg | 96 |
| Leu | Gly | Trp | Arg | Pro | Gly | Trp | Phe | Leu | Asp | Ser | Pro | Asp | Arg | Pro | Trp | |
| | | | 20 | | | | | 25 | | | | | 30 | | | |
| aac | ccg | ccg | acc | ttt | agc | ccg | gcg | ctg | ctg | gtg | gtg | acc | gaa | ggc | gat | 144 |
| Asn | Pro | Pro | Thr | Phe | Ser | Pro | Ala | Leu | Leu | Val | Val | Thr | Glu | Gly | Asp | |
| | | 35 | | | | | 40 | | | | | 45 | | | | |
| aac | gcg | acc | ttt | acc | tgc | agc | ttt | agc | aac | acc | agc | gaa | agc | ttt | gtg | 192 |
| Asn | Ala | Thr | Phe | Thr | Cys | Ser | Phe | Ser | Asn | Thr | Ser | Glu | Ser | Phe | Val | |
| | 50 | | | | | 55 | | | | | 60 | | | | | |
| ctg | aac | tgg | tat | cgc | atg | agc | ccg | agc | aac | cag | acc | gat | aaa | ctg | gcg | 240 |
| Leu | Asn | Trp | Tyr | Arg | Met | Ser | Pro | Ser | Asn | Gln | Thr | Asp | Lys | Leu | Ala | |
| 65 | | | | | 70 | | | | | 75 | | | | | 80 | |
| gcg | ttt | ccg | gaa | gat | cgc | agc | cag | ccg | ggc | cag | gat | tgc | cgc | ttt | cgc | 288 |
| Ala | Phe | Pro | Glu | Asp | Arg | Ser | Gln | Pro | Gly | Gln | Asp | Cys | Arg | Phe | Arg | |
| | | | | 85 | | | | | 90 | | | | | 95 | | |
| gtg | acc | cag | ctg | ccg | aac | ggc | cgc | gat | ttt | cat | atg | agc | gtg | gtg | cgc | 336 |
| Val | Thr | Gln | Leu | Pro | Asn | Gly | Arg | Asp | Phe | His | Met | Ser | Val | Val | Arg | |
| | | | 100 | | | | | 105 | | | | | 110 | | | |
| gcg | cgc | cgc | aac | gat | agc | ggc | acc | tat | ctg | tgc | ggc | gcg | att | agc | ctg | 384 |
| Ala | Arg | Arg | Asn | Asp | Ser | Gly | Thr | Tyr | Leu | Cys | Gly | Ala | Ile | Ser | Leu | |
| | | 115 | | | | | 120 | | | | | 125 | | | | |
| gcg | ccg | aaa | gcg | cag | att | aaa | gaa | agc | ctg | cgc | gcg | gaa | ctg | cgc | gtg | 432 |
| Ala | Pro | Lys | Ala | Gln | Ile | Lys | Glu | Ser | Leu | Arg | Ala | Glu | Leu | Arg | Val | |
| | 130 | | | | | 135 | | | | | 140 | | | | | |
| acc | gaa | cgc | cgc | gcg | gaa | gtg | ccg | acc | gcg | cat | ccg | agc | ccg | agc | ccg | 480 |
| Thr | Glu | Arg | Arg | Ala | Glu | Val | Pro | Thr | Ala | His | Pro | Ser | Pro | Ser | Pro | |
| 145 | | | | | 150 | | | | | 155 | | | | | 160 | |
| cgc | ccg | gcg | ggc | cag | ttt | cag | acc | ctg | gtg | gtg | ggc | gtg | gtg | ggc | ggc | 528 |
| Arg | Pro | Ala | Gly | Gln | Phe | Gln | Thr | Leu | Val | Val | Gly | Val | Val | Gly | Gly | |
| | | | | 165 | | | | | 170 | | | | | 175 | | |
| ctg | ctg | ggc | agc | ctg | gtg | ctg | ctg | gtg | tgg | gtg | ctg | gcg | gtg | att | tgc | 576 |
| Leu | Leu | Gly | Ser | Leu | Val | Leu | Leu | Val | Trp | Val | Leu | Ala | Val | Ile | Cys | |
| | | | 180 | | | | | 185 | | | | | 190 | | | |
| agc | cgc | gcg | gcg | cgc | ggc | acc | att | ggc | gcg | cgc | cgc | acc | ggc | cag | ccg | 624 |
| Ser | Arg | Ala | Ala | Arg | Gly | Thr | Ile | Gly | Ala | Arg | Arg | Thr | Gly | Gln | Pro | |
| | | 195 | | | | | 200 | | | | | 205 | | | | |
| ctg | aaa | gaa | gat | ccg | agc | gcg | gtg | ccg | gtg | ttt | agc | gtg | gat | tat | ggc | 672 |
| Leu | Lys | Glu | Asp | Pro | Ser | Ala | Val | Pro | Val | Phe | Ser | Val | Asp | Tyr | Gly | |
| | 210 | | | | | 215 | | | | | 220 | | | | | |
| gaa | ctg | gat | ttt | cag | tgg | cgc | gaa | aaa | acc | ccg | gaa | ccg | ccg | gtg | ccg | 720 |
| Glu | Leu | Asp | Phe | Gln | Trp | Arg | Glu | Lys | Thr | Pro | Glu | Pro | Pro | Val | Pro | |
| 225 | | | | | 230 | | | | | 235 | | | | | 240 | |
| tgc | gtg | ccg | gaa | cag | acc | gaa | tat | gcg | acc | att | gtg | ttt | ccg | agc | ggc | 768 |
| Cys | Val | Pro | Glu | Gln | Thr | Glu | Tyr | Ala | Thr | Ile | Val | Phe | Pro | Ser | Gly | |
| | | | | 245 | | | | | 250 | | | | | 255 | | |

```
atg ggc acc agc agc ccg gcg cgc cgc ggc agc gcg gat ggc ccg cgc     816
Met Gly Thr Ser Ser Pro Ala Arg Arg Gly Ser Ala Asp Gly Pro Arg
    260                 265                 270 agc gcg cag ccg ctg cgc ccg gaa gat ggc cat tgc agc tgg ccg ctg     864
Ser Ala Gln Pro Leu Arg Pro Glu Asp Gly His Cys Ser Trp Pro Leu
275                 280                 285

<210> SEQ ID NO 4
<211> LENGTH: 288
<212> TYPE: PRT
<213> ORGANISM: Artificial Sequence
<220> FEATURE:
<223> OTHER INFORMATION: [CDS]:1..864 from SEQ ID NO 3

<400> SEQUENCE: 4

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 5
<211> LENGTH: 570
<212> TYPE: DNA
<213> ORGANISM: Artificial Sequence
<220> FEATURE:
```

```
<221> NAME/KEY: source
<222> LOCATION: 1..570
<223> OTHER INFORMATION: /mol_type="unassigned DNA"
      /note="murine P1 extracellular and transmembrane domain (AA1-190)
      (PTM construct)"
      /organism="Artificial Sequence"
<220> FEATURE:
<221> NAME/KEY: CDS
<222> LOCATION: 1..570
<223> OTHER INFORMATION: /transl_table=1

<400> SEQUENCE: 5 atg tgg gtg cgc cag gtg ccg tgg agc ttt acc tgg gcg gtg ctg cag      48
Met Trp Val Arg Gln Val Pro Trp Ser Phe Thr Trp Ala Val Leu Gln
1               5                   10                  15 ctg agc tgg cag agc ggc tgg ctg ctg gaa gtg ccg aac ggc ccg tgg      96
Leu Ser Trp Gln Ser Gly Trp Leu Leu Glu Val Pro Asn Gly Pro Trp
            20                  25                  30 cgc agc ctg acc ttt tat ccg gcg tgg ctg acc gtg agc gaa ggc gcg     144
Arg Ser Leu Thr Phe Tyr Pro Ala Trp Leu Thr Val Ser Glu Gly Ala
        35                  40                  45 aac gcg acc ttt acc tgc agc ctg agc aac tgg agc gaa gat ctg atg     192
Asn Ala Thr Phe Thr Cys Ser Leu Ser Asn Trp Ser Glu Asp Leu Met
50                  55                  60 ctg aac tgg aac cgc ctg agc ccg agc aac cag acc gaa aaa cag gcg     240
Leu Asn Trp Asn Arg Leu Ser Pro Ser Asn Gln Thr Glu Lys Gln Ala
65                  70                  75                  80 gcg ttt tgc aac ggc ctg agc cag ccg gtg cag gat gcg cgc ttt cag     288
Ala Phe Cys Asn Gly Leu Ser Gln Pro Val Gln Asp Ala Arg Phe Gln
                85                  90                  95 att att cag ctg ccg aac cgc cat gat ttt cat atg aac att ctg gat     336
Ile Ile Gln Leu Pro Asn Arg His Asp Phe His Met Asn Ile Leu Asp
            100                 105                 110 acc cgc cgc aac gat agc ggc att tat ctg tgc ggc gcg att agc ctg     384
Thr Arg Arg Asn Asp Ser Gly Ile Tyr Leu Cys Gly Ala Ile Ser Leu
        115                 120                 125 cat ccg aaa gcg aaa att gaa gaa agc ccg ggc gcg gaa ctg gtg gtg     432
His Pro Lys Ala Lys Ile Glu Glu Ser Pro Gly Ala Glu Leu Val Val
130                 135                 140 acc gaa cgc att ctg gaa acc agc acc cgc tat ccg agc ccg agc ccg     480
Thr Glu Arg Ile Leu Glu Thr Ser Thr Arg Tyr Pro Ser Pro Ser Pro
145                 150                 155                 160 aaa ccg gaa ggc cgc ttt cag ggc atg gtg att ggc att atg agc gcg     528
Lys Pro Glu Gly Arg Phe Gln Gly Met Val Ile Gly Ile Met Ser Ala
                165                 170                 175 ctg gtg ggc att ccg gtg ctg ctg ctg gcg tgg gcg ctg              570
Leu Val Gly Ile Pro Val Leu Leu Leu Ala Trp Ala Leu
            180                 185                 190

<210> SEQ ID NO 6
<211> LENGTH: 190
<212> TYPE: PRT
<213> ORGANISM: Artificial Sequence
<220> FEATURE:
<223> OTHER INFORMATION: [CDS]:1..570 from SEQ ID NO 5

<400> SEQUENCE: 6

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45
```

| | | | | | | | | | | | | |
|---|---|---|---|---|---|---|---|---|---|---|---|---|
| Asn | Ala | Thr | Phe | Thr | Cys | Ser | Leu | Ser | Asn | Trp | Ser | Glu | Asp | Leu | Met |
| | 50 | | | | 55 | | | | 60 | | | |

Asn Ala Thr Phe Thr Cys Ser Leu Ser Asn Trp Ser Glu Asp Leu Met
       50                      55                     60

Leu Asn Trp Asn Arg Leu Ser Pro Ser Asn Gln Thr Glu Lys Gln Ala
65                   70                      75                 80

Ala Phe Cys Asn Gly Leu Ser Gln Pro Val Gln Asp Ala Arg Phe Gln
                     85                      90                 95

Ile Ile Gln Leu Pro Asn Arg His Asp Phe His Met Asn Ile Leu Asp
               100                  105                110

Thr Arg Arg Asn Asp Ser Gly Ile Tyr Leu Cys Gly Ala Ile Ser Leu
               115                  120                125

His Pro Lys Ala Lys Ile Glu Glu Ser Pro Gly Ala Glu Leu Val Val
     130                    135                140

Thr Glu Arg Ile Leu Glu Thr Ser Thr Arg Tyr Pro Ser Pro Ser Pro
145                   150                  155              160

Lys Pro Glu Gly Arg Phe Gln Gly Met Val Ile Gly Ile Met Ser Ala
               165                  170              175

Leu Val Gly Ile Pro Val Leu Leu Leu Leu Ala Trp Ala Leu
               180                  185              190

<210> SEQ ID NO 7
<211> LENGTH: 507
<212> TYPE: DNA
<213> ORGANISM: Artificial Sequence
<220> FEATURE:
<221> NAME/KEY: source
<222> LOCATION: 1..507
<223> OTHER INFORMATION: /mol_type="unassigned DNA"
    /note="murine PTM PD-1 extracellular domain (without
    transmembrane PD-1 domain)"
    /organism="Artificial Sequence"
<220> FEATURE:
<221> NAME/KEY: CDS
<222> LOCATION: 1..507
<223> OTHER INFORMATION: /transl_table=1

<400> SEQUENCE: 7

```
atg tgg gtg cgc cag gtg ccg tgg agc ttt acc tgg gcg gtg ctg cag      48
Met Trp Val Arg Gln Val Pro Trp Ser Phe Thr Trp Ala Val Leu Gln
1               5                   10                  15 ctg agc tgg cag agc ggc tgg ctg ctg gaa gtg ccg aac ggc ccg tgg      96
Leu Ser Trp Gln Ser Gly Trp Leu Leu Glu Val Pro Asn Gly Pro Trp
            20                  25                  30 cgc agc ctg acc ttt tat ccg gcg tgg ctg acc gtg agc gaa ggc gcg     144
Arg Ser Leu Thr Phe Tyr Pro Ala Trp Leu Thr Val Ser Glu Gly Ala
        35                  40                  45 aac gcg acc ttt acc tgc agc ctg agc aac tgg agc gaa gat ctg atg     192
Asn Ala Thr Phe Thr Cys Ser Leu Ser Asn Trp Ser Glu Asp Leu Met
    50                  55                  60 ctg aac tgg aac cgc ctg agc ccg agc aac cag acc gaa aaa cag gcg     240
Leu Asn Trp Asn Arg Leu Ser Pro Ser Asn Gln Thr Glu Lys Gln Ala
65                  70                  75                  80 gcg ttt tgc aac ggc ctg agc cag ccg gtg cag gat gcg cgc ttt cag     288
Ala Phe Cys Asn Gly Leu Ser Gln Pro Val Gln Asp Ala Arg Phe Gln
                85                  90                  95 att att cag ctg ccg aac cgc cat gat ttt cat atg aac att ctg gat     336
Ile Ile Gln Leu Pro Asn Arg His Asp Phe His Met Asn Ile Leu Asp
            100                 105                 110 acc cgc cgc aac gat agc ggc att tat ctg tgc ggc gcg att agc ctg     384
Thr Arg Arg Asn Asp Ser Gly Ile Tyr Leu Cys Gly Ala Ile Ser Leu
        115                 120                 125
```

```
cat ccg aaa gcg aaa att gaa gaa agc ccg ggc gcg gaa ctg gtg gtg    432
His Pro Lys Ala Lys Ile Glu Glu Ser Pro Gly Ala Glu Leu Val Val
            130                 135                 140 acc gaa cgc att ctg gaa acc agc acc cgc tat ccg agc ccg agc ccg    480
Thr Glu Arg Ile Leu Glu Thr Ser Thr Arg Tyr Pro Ser Pro Ser Pro
145                 150                 155                 160 aaa ccg gaa ggc cgc ttt cag ggc atg                                507
Lys Pro Glu Gly Arg Phe Gln Gly Met
                165

<210> SEQ ID NO 8
<211> LENGTH: 169
<212> TYPE: PRT
<213> ORGANISM: Artificial Sequence
<220> FEATURE:
<223> OTHER INFORMATION: [CDS]:1..507 from SEQ ID NO 7

<400> SEQUENCE: 8

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met
                165

<210> SEQ ID NO 9
<211> LENGTH: 63
<212> TYPE: DNA
<213> ORGANISM: Artificial Sequence
<220> FEATURE:
<221> NAME/KEY: source
<222> LOCATION: 1..63
<223> OTHER INFORMATION: /mol_type="unassigned DNA"
      /note="murine PTM PD-1 transmembrane domain"
      /organism="Artificial Sequence"
<220> FEATURE:
<221> NAME/KEY: CDS
<222> LOCATION: 1..63
<223> OTHER INFORMATION: /transl_table=1

<400> SEQUENCE: 9 gtg att ggc att atg agc gcg ctg gtg ggc att ccg gtg ctg ctg ctg    48
Val Ile Gly Ile Met Ser Ala Leu Val Gly Ile Pro Val Leu Leu Leu
1               5                   10                  15 ctg gcg tgg gcg ctg                                                 63
Leu Ala Trp Ala Leu
```

<210> SEQ ID NO 10
<211> LENGTH: 21
<212> TYPE: PRT
<213> ORGANISM: Artificial Sequence
<220> FEATURE:
<223> OTHER INFORMATION: [CDS]:1..63 from SEQ ID NO 9

<400> SEQUENCE: 10

Val Ile Gly Ile Met Ser Ala Leu Val Gly Ile Pro Val Leu Leu Leu
1               5                   10                  15

Leu Ala Trp Ala Leu
            20

<210> SEQ ID NO 11
<211> LENGTH: 123
<212> TYPE: DNA
<213> ORGANISM: Artificial Sequence
<220> FEATURE:
<221> NAME/KEY: source
<222> LOCATION: 1..123
<223> OTHER INFORMATION: /mol_type="unassigned DNA"
      /note="murine CD28 intracellular domain (AA178-218) (PTM
      construct)"
      /organism="Artificial Sequence"
<220> FEATURE:
<221> NAME/KEY: CDS
<222> LOCATION: 1..123
<223> OTHER INFORMATION: /transl_table=1

<400> SEQUENCE: 11 aac agc cgc cgc aac cgc ctg ctg cag agc gat tat atg aac atg acc      48
Asn Ser Arg Arg Asn Arg Leu Leu Gln Ser Asp Tyr Met Asn Met Thr
1               5                   10                  15 ccg cgc cgc ccg ggc ctg acc cgc aaa ccg tat cag ccg tat gcg ccg      96
Pro Arg Arg Pro Gly Leu Thr Arg Lys Pro Tyr Gln Pro Tyr Ala Pro
                20                  25                  30 gcg cgc gat ttt gcg gcg tat cgc ccg                                  123
Ala Arg Asp Phe Ala Ala Tyr Arg Pro
        35                  40

<210> SEQ ID NO 12
<211> LENGTH: 41
<212> TYPE: PRT
<213> ORGANISM: Artificial Sequence
<220> FEATURE:
<223> OTHER INFORMATION: [CDS]:1..123 from SEQ ID NO 11

<400> SEQUENCE: 12

Asn Ser Arg Arg Asn Arg Leu Leu Gln Ser Asp Tyr Met Asn Met Thr
1               5                   10                  15

Pro Arg Arg Pro Gly Leu Thr Arg Lys Pro Tyr Gln Pro Tyr Ala Pro
                20                  25                  30

Ala Arg Asp Phe Ala Ala Tyr Arg Pro
        35                  40

<210> SEQ ID NO 13
<211> LENGTH: 693
<212> TYPE: DNA
<213> ORGANISM: Artificial Sequence
<220> FEATURE:
<221> NAME/KEY: source
<222> LOCATION: 1..693
<223> OTHER INFORMATION: /mol_type="unassigned DNA"
      /note="murine PD1-CD28 (PTM construct)"
      /organism="Artificial Sequence"

<220> FEATURE:
<221> NAME/KEY: CDS
<222> LOCATION: 1..693
<223> OTHER INFORMATION: /transl_table=1

<400> SEQUENCE: 13

| | | | | | | | | | | | | | | | | |
|---|---|---|---|---|---|---|---|---|---|---|---|---|---|---|---|---|
| atg | tgg | gtg | cgc | cag | gtg | ccg | tgg | agc | ttt | acc | tgg | gcg | gtg | ctg | cag | 48 |
| Met | Trp | Val | Arg | Gln | Val | Pro | Trp | Ser | Phe | Thr | Trp | Ala | Val | Leu | Gln | |
| 1 | | | | 5 | | | | | 10 | | | | | 15 | | |
| ctg | agc | tgg | cag | agc | ggc | tgg | ctg | ctg | gaa | gtg | ccg | aac | ggc | ccg | tgg | 96 |
| Leu | Ser | Trp | Gln | Ser | Gly | Trp | Leu | Leu | Glu | Val | Pro | Asn | Gly | Pro | Trp | |
| | | | 20 | | | | | 25 | | | | | 30 | | | |
| cgc | agc | ctg | acc | ttt | tat | ccg | gcg | tgg | ctg | acc | gtg | agc | gaa | ggc | gcg | 144 |
| Arg | Ser | Leu | Thr | Phe | Tyr | Pro | Ala | Trp | Leu | Thr | Val | Ser | Glu | Gly | Ala | |
| | | 35 | | | | | 40 | | | | | 45 | | | | |
| aac | gcg | acc | ttt | acc | tgc | agc | ctg | agc | aac | tgg | agc | gaa | gat | ctg | atg | 192 |
| Asn | Ala | Thr | Phe | Thr | Cys | Ser | Leu | Ser | Asn | Trp | Ser | Glu | Asp | Leu | Met | |
| | 50 | | | | | 55 | | | | | 60 | | | | | |
| ctg | aac | tgg | aac | cgc | ctg | agc | ccg | agc | aac | cag | acc | gaa | aaa | cag | gcg | 240 |
| Leu | Asn | Trp | Asn | Arg | Leu | Ser | Pro | Ser | Asn | Gln | Thr | Glu | Lys | Gln | Ala | |
| 65 | | | | | 70 | | | | | 75 | | | | | 80 | |
| gcg | ttt | tgc | aac | ggc | ctg | agc | cag | ccg | gtg | cag | gat | gcg | cgc | ttt | cag | 288 |
| Ala | Phe | Cys | Asn | Gly | Leu | Ser | Gln | Pro | Val | Gln | Asp | Ala | Arg | Phe | Gln | |
| | | | | 85 | | | | | 90 | | | | | 95 | | |
| att | att | cag | ctg | ccg | aac | cgc | cat | gat | ttt | cat | atg | aac | att | ctg | gat | 336 |
| Ile | Ile | Gln | Leu | Pro | Asn | Arg | His | Asp | Phe | His | Met | Asn | Ile | Leu | Asp | |
| | | | 100 | | | | | 105 | | | | | 110 | | | |
| acc | cgc | cgc | aac | gat | agc | ggc | att | tat | ctg | tgc | ggc | gcg | att | agc | ctg | 384 |
| Thr | Arg | Arg | Asn | Asp | Ser | Gly | Ile | Tyr | Leu | Cys | Gly | Ala | Ile | Ser | Leu | |
| | | 115 | | | | | 120 | | | | | 125 | | | | |
| cat | ccg | aaa | gcg | aaa | att | gaa | gaa | agc | ccg | ggc | gcg | gaa | ctg | gtg | gtg | 432 |
| His | Pro | Lys | Ala | Lys | Ile | Glu | Glu | Ser | Pro | Gly | Ala | Glu | Leu | Val | Val | |
| | 130 | | | | | 135 | | | | | 140 | | | | | |
| acc | gaa | cgc | att | ctg | gaa | acc | agc | acc | cgc | tat | ccg | agc | ccg | agc | ccg | 480 |
| Thr | Glu | Arg | Ile | Leu | Glu | Thr | Ser | Thr | Arg | Tyr | Pro | Ser | Pro | Ser | Pro | |
| 145 | | | | | 150 | | | | | 155 | | | | | 160 | |
| aaa | ccg | gaa | ggc | cgc | ttt | cag | ggc | atg | gtg | att | ggc | att | atg | agc | gcg | 528 |
| Lys | Pro | Glu | Gly | Arg | Phe | Gln | Gly | Met | Val | Ile | Gly | Ile | Met | Ser | Ala | |
| | | | | 165 | | | | | 170 | | | | | 175 | | |
| ctg | gtg | ggc | att | ccg | gtg | ctg | ctg | ctg | gcg | tgg | gcg | ctg | aac | agc | | 576 |
| Leu | Val | Gly | Ile | Pro | Val | Leu | Leu | Leu | Ala | Trp | Ala | Leu | Asn | Ser | | |
| | | | 180 | | | | | 185 | | | | | 190 | | | |
| cgc | cgc | aac | cgc | ctg | ctg | cag | agc | gat | tat | atg | aac | atg | acc | ccg | cgc | 624 |
| Arg | Arg | Asn | Arg | Leu | Leu | Gln | Ser | Asp | Tyr | Met | Asn | Met | Thr | Pro | Arg | |
| | | 195 | | | | | 200 | | | | | 205 | | | | |
| cgc | ccg | ggc | ctg | acc | cgc | aaa | ccg | tat | cag | ccg | tat | gcg | ccg | gcg | cgc | 672 |
| Arg | Pro | Gly | Leu | Thr | Arg | Lys | Pro | Tyr | Gln | Pro | Tyr | Ala | Pro | Ala | Arg | |
| | 210 | | | | | 215 | | | | | 220 | | | | | |
| gat | ttt | gcg | gcg | tat | cgc | ccg | | | | | | | | | | 693 |
| Asp | Phe | Ala | Ala | Tyr | Arg | Pro | | | | | | | | | | |
| 225 | | | | 230 | | | | | | | | | | | | |

<210> SEQ ID NO 14
<211> LENGTH: 231
<212> TYPE: PRT
<213> ORGANISM: Artificial Sequence
<220> FEATURE:
<223> OTHER INFORMATION: [CDS]:1..693 from SEQ ID NO 13

<400> SEQUENCE: 14

| | | | | | | | | | | | | | | | |
|---|---|---|---|---|---|---|---|---|---|---|---|---|---|---|---|
| Met | Trp | Val | Arg | Gln | Val | Pro | Trp | Ser | Phe | Thr | Trp | Ala | Val | Leu | Gln |
| 1 | | | | 5 | | | | | 10 | | | | | 15 | |

Leu Ser Trp Gln Ser Gly Trp Leu Leu Glu Val Pro Asn Gly Pro Trp
    20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
                165                 170                 175

Leu Val Gly Ile Pro Val Leu Leu Leu Leu Ala Trp Ala Leu Asn Ser
            180                 185                 190

Arg Arg Asn Arg Leu Leu Gln Ser Asp Tyr Met Asn Met Thr Pro Arg
        195                 200                 205

Arg Pro Gly Leu Thr Arg Lys Pro Tyr Gln Pro Tyr Ala Pro Ala Arg
    210                 215                 220

Asp Phe Ala Ala Tyr Arg Pro
225                 230

<210> SEQ ID NO 15
<211> LENGTH: 573
<212> TYPE: DNA
<213> ORGANISM: Artificial Sequence
<220> FEATURE:
<221> NAME/KEY: source
<222> LOCATION: 1..573
<223> OTHER INFORMATION: /mol_type="unassigned DNA"
     /note="human PTM PD-1 extracellular domain plus transmembrane
     PD-1 domain"
     /organism="Artificial Sequence"
<220> FEATURE:
<221> NAME/KEY: CDS
<222> LOCATION: 1..573
<223> OTHER INFORMATION: /transl_table=1

<400> SEQUENCE: 15

```
atg cag att ccg cag gcg ccg tgg ccg gtg gtg tgg gcg gtg ctg cag      48
Met Gln Ile Pro Gln Ala Pro Trp Pro Val Val Trp Ala Val Leu Gln
1               5                   10                  15 ctg ggc tgg cgc ccg ggc tgg ttt ctg gat agc ccg gat cgc ccg tgg      96
Leu Gly Trp Arg Pro Gly Trp Phe Leu Asp Ser Pro Asp Arg Pro Trp
            20                  25                  30 aac ccg ccg acc ttt agc ccg gcg ctg ctg gtg gtg acc gaa ggc gat     144
Asn Pro Pro Thr Phe Ser Pro Ala Leu Leu Val Val Thr Glu Gly Asp
        35                  40                  45 aac gcg acc ttt acc tgc agc ttt agc aac acc agc gaa agc ttt gtg     192
Asn Ala Thr Phe Thr Cys Ser Phe Ser Asn Thr Ser Glu Ser Phe Val
    50                  55                  60 ctg aac tgg tat cgc atg agc ccg agc aac cag acc gat aaa ctg gcg     240
```

| | | | | | | | | | | | | | | |
|---|---|---|---|---|---|---|---|---|---|---|---|---|---|---|
|Leu|Asn|Trp|Tyr|Arg|Met|Ser|Pro|Ser|Asn|Gln|Thr|Asp|Lys|Leu|Ala|
|65| | | |70| | | |75| | | | |80| | |

```
gcg ttt ccg gaa gat cgc agc cag ccg ggc cag gat tgc cgc ttt cgc    288
Ala Phe Pro Glu Asp Arg Ser Gln Pro Gly Gln Asp Cys Arg Phe Arg
                85                  90                  95 gtg acc cag ctg ccg aac ggc cgc gat ttt cat atg agc gtg gtg cgc    336
Val Thr Gln Leu Pro Asn Gly Arg Asp Phe His Met Ser Val Val Arg
            100                 105                 110 gcg cgc cgc aac gat agc ggc acc tat ctg tgc ggc gcg att agc ctg    384
Ala Arg Arg Asn Asp Ser Gly Thr Tyr Leu Cys Gly Ala Ile Ser Leu
        115                 120                 125 gcg ccg aaa gcg cag att aaa gaa agc ctg cgc gcg gaa ctg cgc gtg    432
Ala Pro Lys Ala Gln Ile Lys Glu Ser Leu Arg Ala Glu Leu Arg Val
    130                 135                 140 acc gaa cgc cgc gcg gaa gtg ccg acc gcg cat ccg agc ccg agc ccg    480
Thr Glu Arg Arg Ala Glu Val Pro Thr Ala His Pro Ser Pro Ser Pro
145                 150                 155                 160 cgc ccg gcg ggc cag ttt cag acc ctg gtg gtg ggc gtg gtg ggc ggc    528
Arg Pro Ala Gly Gln Phe Gln Thr Leu Val Val Gly Val Val Gly Gly
                165                 170                 175 ctg ctg ggc agc ctg gtg ctg ctg gtg tgg gtg ctg gcg gtg att        573
Leu Leu Gly Ser Leu Val Leu Leu Val Trp Val Leu Ala Val Ile
            180                 185                 190

<210> SEQ ID NO 16
<211> LENGTH: 191
<212> TYPE: PRT
<213> ORGANISM: Artificial Sequence
<220> FEATURE:
<223> OTHER INFORMATION: [CDS]:1..573 from SEQ ID NO 15

<400> SEQUENCE: 16

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65              70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile
            180                 185                 190

<210> SEQ ID NO 17
```

```
<211> LENGTH: 510
<212> TYPE: DNA
<213> ORGANISM: Artificial Sequence
<220> FEATURE:
<221> NAME/KEY: source
<222> LOCATION: 1..510
<223> OTHER INFORMATION: /mol_type="unassigned DNA"
      /note="human PD1 extracellular domain (without transmembrane
      domain) (PD1-CD28 construct)"
      /organism="Artificial Sequence"
<220> FEATURE:
<221> NAME/KEY: CDS
<222> LOCATION: 1..510
<223> OTHER INFORMATION: /transl_table=1

<400> SEQUENCE: 17 atg cag atc cca cag gcg ccc tgg cca gtc gtc tgg gcg gtg cta caa      48
Met Gln Ile Pro Gln Ala Pro Trp Pro Val Val Trp Ala Val Leu Gln
1               5                   10                  15 ctg ggc tgg cgg cca gga tgg ttc tta gac tcc cca gac agg ccc tgg      96
Leu Gly Trp Arg Pro Gly Trp Phe Leu Asp Ser Pro Asp Arg Pro Trp
            20                  25                  30 aac ccc ccc acc ttc tcc cca gcc ctg ctc gtg gtg acc gaa ggg gac     144
Asn Pro Pro Thr Phe Ser Pro Ala Leu Leu Val Val Thr Glu Gly Asp
        35                  40                  45 aac gcc acc ttc acc tgc agc ttc tcc aac aca tcg gag agc ttc gtg     192
Asn Ala Thr Phe Thr Cys Ser Phe Ser Asn Thr Ser Glu Ser Phe Val
    50                  55                  60 cta aac tgg tac cgc atg agc ccc agc aac cag acg gac aag ctg gcc     240
Leu Asn Trp Tyr Arg Met Ser Pro Ser Asn Gln Thr Asp Lys Leu Ala
65                  70                  75                  80 gcc ttc ccc gag gac cgc agc cag ccc ggc cag gac tgc cgc ttc cgt     288
Ala Phe Pro Glu Asp Arg Ser Gln Pro Gly Gln Asp Cys Arg Phe Arg
                85                  90                  95 gtc aca caa ctg ccc aac ggg cgt gac ttc cac atg agc gtg gtc agg     336
Val Thr Gln Leu Pro Asn Gly Arg Asp Phe His Met Ser Val Val Arg
            100                 105                 110 gcc cgg cgc aat gac agc ggc acc tac ctc tgt ggg gcc atc tcc ctg     384
Ala Arg Arg Asn Asp Ser Gly Thr Tyr Leu Cys Gly Ala Ile Ser Leu
        115                 120                 125 gcc ccc aag gcg cag atc aaa gag agc ctg cgg gca gag ctc agg gtg     432
Ala Pro Lys Ala Gln Ile Lys Glu Ser Leu Arg Ala Glu Leu Arg Val
    130                 135                 140 aca gag aga agg gca gaa gtg ccc aca gcc cac ccc agc ccc tca ccc     480
Thr Glu Arg Arg Ala Glu Val Pro Thr Ala His Pro Ser Pro Ser Pro
145                 150                 155                 160 agg cca gcc ggc cag ttc caa acc ctg gtg                             510
Arg Pro Ala Gly Gln Phe Gln Thr Leu Val
                165                 170

<210> SEQ ID NO 18
<211> LENGTH: 170
<212> TYPE: PRT
<213> ORGANISM: Artificial Sequence
<220> FEATURE:
<223> OTHER INFORMATION: [CDS]:1..510 from SEQ ID NO 17

<400> SEQUENCE: 18

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45
```

```
Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
                115                 120                 125

Ala Pro Lys Ala Gln Ile Lys Glu Ser Leu Arg Ala Glu Leu Arg Val
                130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val
                165                 170

<210> SEQ ID NO 19
<211> LENGTH: 63
<212> TYPE: DNA
<213> ORGANISM: Artificial Sequence
<220> FEATURE:
<221> NAME/KEY: source
<222> LOCATION: 1..63
<223> OTHER INFORMATION: /mol_type="unassigned DNA"
      /note="human PD1, transmembrane region (PD1-CD28 construct)"
      /organism="Artificial Sequence"
<220> FEATURE:
<221> NAME/KEY: CDS
<222> LOCATION: 1..63
<223> OTHER INFORMATION: /transl_table=1

<400> SEQUENCE: 19 gtt ggt gtc gtg ggc ggc ctg ctg ggc agc ctg gtg ctg cta gtc tgg    48
Val Gly Val Val Gly Gly Leu Leu Gly Ser Leu Val Leu Leu Val Trp
1               5                   10                  15 gtc ctg gcc gtc atc                                                63
Val Leu Ala Val Ile
            20

<210> SEQ ID NO 20
<211> LENGTH: 21
<212> TYPE: PRT
<213> ORGANISM: Artificial Sequence
<220> FEATURE:
<223> OTHER INFORMATION: [CDS]:1..63 from SEQ ID NO 19

<400> SEQUENCE: 20

Val Gly Val Val Gly Gly Leu Leu Gly Ser Leu Val Leu Leu Val Trp
1               5                   10                  15

Val Leu Ala Val Ile
            20

<210> SEQ ID NO 21
<211> LENGTH: 126
<212> TYPE: DNA
<213> ORGANISM: Artificial Sequence
<220> FEATURE:
<221> NAME/KEY: source
<222> LOCATION: 1..126
<223> OTHER INFORMATION: /mol_type="unassigned DNA"
      /note="human CD28 (PD1-CD28 construct)"
      /organism="Artificial Sequence"
<220> FEATURE:
```

```
<221> NAME/KEY: CDS
<222> LOCATION: 1..126
<223> OTHER INFORMATION: /transl_table=1

<400> SEQUENCE: 21 agg agt aag agg agc agg ctc ctg cac agt gac tac atg aac atg act       48
Arg Ser Lys Arg Ser Arg Leu Leu His Ser Asp Tyr Met Asn Met Thr
1               5                   10                  15 ccc cgc cgc ccc ggg ccc acc cgc aag cat tac cag ccc tat gcc cca       96
Pro Arg Arg Pro Gly Pro Thr Arg Lys His Tyr Gln Pro Tyr Ala Pro
                20                  25                  30 cca cgc gac ttc gca gcc tat cgc tcc taa                              126
Pro Arg Asp Phe Ala Ala Tyr Arg Ser
        35                  40

<210> SEQ ID NO 22
<211> LENGTH: 41
<212> TYPE: PRT
<213> ORGANISM: Artificial Sequence
<220> FEATURE:
<223> OTHER INFORMATION: [CDS]:1..126 from SEQ ID NO 21

<400> SEQUENCE: 22

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
        35                  40

<210> SEQ ID NO 23
<211> LENGTH: 699
<212> TYPE: DNA
<213> ORGANISM: Artificial Sequence
<220> FEATURE:
<221> NAME/KEY: source
<222> LOCATION: 1..699
<223> OTHER INFORMATION: /mol_type="unassigned DNA"
      /note="human PD1-CD28 construct"
      /organism="Artificial Sequence"
<220> FEATURE:
<221> NAME/KEY: CDS
<222> LOCATION: 1..699
<223> OTHER INFORMATION: /transl_table=1

<400> SEQUENCE: 23 atg cag atc cca cag gcg ccc tgg cca gtc gtc tgg gcg gtg cta caa       48
Met Gln Ile Pro Gln Ala Pro Trp Pro Val Val Trp Ala Val Leu Gln
1               5                   10                  15 ctg ggc tgg cgg cca gga tgg ttc tta gac tcc cca gac agg ccc tgg       96
Leu Gly Trp Arg Pro Gly Trp Phe Leu Asp Ser Pro Asp Arg Pro Trp
                20                  25                  30 aac ccc ccc acc ttc tcc cca gcc ctg ctc gtg gtg acc gaa ggg gac      144
Asn Pro Pro Thr Phe Ser Pro Ala Leu Leu Val Val Thr Glu Gly Asp
                35                  40                  45 aac gcc acc ttc acc tgc agc ttc tcc aac aca tcg gag agc ttc gtg      192
Asn Ala Thr Phe Thr Cys Ser Phe Ser Asn Thr Ser Glu Ser Phe Val
    50                  55                  60 cta aac tgg tac cgc atg agc ccc agc aac cag acg gac aag ctg gcc      240
Leu Asn Trp Tyr Arg Met Ser Pro Ser Asn Gln Thr Asp Lys Leu Ala
65                  70                  75                  80 gcc ttc ccc gag gac cgc agc cag ccc ggc cag gac tgc cgc ttc cgt      288
Ala Phe Pro Glu Asp Arg Ser Gln Pro Gly Gln Asp Cys Arg Phe Arg
                85                  90                  95
```

```
gtc aca caa ctg ccc aac ggg cgt gac ttc cac atg agc gtg gtc agg      336
Val Thr Gln Leu Pro Asn Gly Arg Asp Phe His Met Ser Val Val Arg
        100                 105                 110 gcc cgg cgc aat gac agc ggc acc tac ctc tgt ggg gcc atc tcc ctg      384
Ala Arg Arg Asn Asp Ser Gly Thr Tyr Leu Cys Gly Ala Ile Ser Leu
        115                 120                 125 gcc ccc aag gcg cag atc aaa gag agc ctg cgg gca gag ctc agg gtg      432
Ala Pro Lys Ala Gln Ile Lys Glu Ser Leu Arg Ala Glu Leu Arg Val
130                 135                 140 aca gag aga agg gca gaa gtg ccc aca gcc cac ccc agc ccc tca ccc      480
Thr Glu Arg Arg Ala Glu Val Pro Thr Ala His Pro Ser Pro Ser Pro
145                 150                 155                 160 agg cca gcc ggc cag ttc caa acc ctg gtg gtt ggt gtc gtg ggc ggc      528
Arg Pro Ala Gly Gln Phe Gln Thr Leu Val Val Gly Val Val Gly Gly
        165                 170                 175 ctg ctg ggc agc ctg gtg ctg cta gtc tgg gtc ctg gcc gtc atc agg      576
Leu Leu Gly Ser Leu Val Leu Leu Val Trp Val Leu Ala Val Ile Arg
        180                 185                 190 agt aag agg agc agg ctc ctg cac agt gac tac atg aac atg act ccc      624
Ser Lys Arg Ser Arg Leu Leu His Ser Asp Tyr Met Asn Met Thr Pro
        195                 200                 205 cgc cgc ccc ggg ccc acc cgc aag cat tac cag ccc tat gcc cca cca      672
Arg Arg Pro Gly Pro Thr Arg Lys His Tyr Gln Pro Tyr Ala Pro Pro
210                 215                 220 cgc gac ttc gca gcc tat cgc tcc taa                                  699
Arg Asp Phe Ala Ala Tyr Arg Ser
225                 230

<210> SEQ ID NO 24
<211> LENGTH: 232
<212> TYPE: PRT
<213> ORGANISM: Artificial Sequence
<220> FEATURE:
<223> OTHER INFORMATION: [CDS]:1..699 from SEQ ID NO 23

<400> SEQUENCE: 24

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175
```

```
Leu Leu Gly Ser Leu Val Leu Val Trp Val Leu Ala Val Ile Arg
        180                 185                 190

Ser Lys Arg Ser Arg Leu Leu His Ser Asp Tyr Met Asn Met Thr Pro
        195                 200                 205

Arg Arg Pro Gly Pro Thr Arg Lys His Tyr Gln Pro Tyr Ala Pro Pro
        210                 215                 220

Arg Asp Phe Ala Ala Tyr Arg Ser
225                 230
```

<210> SEQ ID NO 25
<211> LENGTH: 654
<212> TYPE: DNA
<213> ORGANISM: Artificial Sequence
<220> FEATURE:
<221> NAME/KEY: source
<222> LOCATION: 1..654
<223> OTHER INFORMATION: /mol_type="unassigned DNA"
    /note="murine full-length CD28"
    /organism="Artificial Sequence"
<220> FEATURE:
<221> NAME/KEY: CDS
<222> LOCATION: 1..654
<223> OTHER INFORMATION: /transl_table=1

<400> SEQUENCE: 25

```
atg acc ctg cgc ctg ctg ttt ctg gcg ctg aac ttt ttt agc gtg cag      48
Met Thr Leu Arg Leu Leu Phe Leu Ala Leu Asn Phe Phe Ser Val Gln
1               5                   10                  15 gtg acc gaa aac aaa att ctg gtg aaa cag agc ccg ctg ctg gtg gtg      96
Val Thr Glu Asn Lys Ile Leu Val Lys Gln Ser Pro Leu Leu Val Val
            20                  25                  30 gat agc aac gaa gtg agc ctg agc tgc cgc tat agc tat aac ctg ctg     144
Asp Ser Asn Glu Val Ser Leu Ser Cys Arg Tyr Ser Tyr Asn Leu Leu
        35                  40                  45 gcg aaa gaa ttt cgc gcg agc ctg tat aaa ggc gtg aac agc gat gtg     192
Ala Lys Glu Phe Arg Ala Ser Leu Tyr Lys Gly Val Asn Ser Asp Val
    50                  55                  60 gaa gtg tgc gtg ggc aac ggc aac ttt acc tat cag ccg cag ttt cgc     240
Glu Val Cys Val Gly Asn Gly Asn Phe Thr Tyr Gln Pro Gln Phe Arg
65                  70                  75                  80 agc aac gcg gaa ttt aac tgc gat ggc gat ttt gat aac gaa acc gtg     288
Ser Asn Ala Glu Phe Asn Cys Asp Gly Asp Phe Asp Asn Glu Thr Val
                85                  90                  95 acc ttt cgc ctg tgg aac ctg cat gtg aac cat acc gat att tat ttt     336
Thr Phe Arg Leu Trp Asn Leu His Val Asn His Thr Asp Ile Tyr Phe
            100                 105                 110 tgc aaa att gaa ttt atg tat ccg ccg ccg tat ctg gat aac gaa cgc     384
Cys Lys Ile Glu Phe Met Tyr Pro Pro Pro Tyr Leu Asp Asn Glu Arg
        115                 120                 125 agc aac ggc acc att att cat att aaa gaa aaa cat ctg tgc cat acc     432
Ser Asn Gly Thr Ile Ile His Ile Lys Glu Lys His Leu Cys His Thr
    130                 135                 140 cag agc agc ccg aaa ctg ttt tgg gcg ctg gtg gtg gtg gcg ggc gtg     480
Gln Ser Ser Pro Lys Leu Phe Trp Ala Leu Val Val Val Ala Gly Val
145                 150                 155                 160 ctg ttt tgc tat ggc ctg ctg gtg acc gtg gcg ctg tgc gtg att tgg     528
Leu Phe Cys Tyr Gly Leu Leu Val Thr Val Ala Leu Cys Val Ile Trp
                165                 170                 175 acc aac agc cgc cgc aac cgc ctg ctg cag agc gat tat atg aac atg     576
Thr Asn Ser Arg Arg Asn Arg Leu Leu Gln Ser Asp Tyr Met Asn Met
            180                 185                 190 acc ccg cgc cgc ccg ggc ctg acc cgc aaa ccg tat cag ccg tat gcg     624
```

```
Thr Pro Arg Arg Pro Gly Leu Thr Arg Lys Pro Tyr Gln Pro Tyr Ala
        195                 200                 205 ccg gcg cgc gat ttt gcg gcg tat cgc ccg                              654
Pro Ala Arg Asp Phe Ala Ala Tyr Arg Pro
    210                 215
```

<210> SEQ ID NO 26
<211> LENGTH: 218
<212> TYPE: PRT
<213> ORGANISM: Artificial Sequence
<220> FEATURE:
<223> OTHER INFORMATION: [CDS]:1..654 from SEQ ID NO 25

<400> SEQUENCE: 26

```
Met Thr Leu Arg Leu Leu Phe Leu Ala Leu Asn Phe Phe Ser Val Gln
1               5                   10                  15

Val Thr Glu Asn Lys Ile Leu Val Lys Gln Ser Pro Leu Leu Val Val
            20                  25                  30

Asp Ser Asn Glu Val Ser Leu Ser Cys Arg Tyr Ser Tyr Asn Leu Leu
        35                  40                  45

Ala Lys Glu Phe Arg Ala Ser Leu Tyr Lys Gly Val Asn Ser Asp Val
    50                  55                  60

Glu Val Cys Val Gly Asn Gly Asn Phe Thr Tyr Gln Pro Gln Phe Arg
65                  70                  75                  80

Ser Asn Ala Glu Phe Asn Cys Asp Gly Asp Phe Asp Asn Glu Thr Val
                85                  90                  95

Thr Phe Arg Leu Trp Asn Leu His Val Asn His Thr Asp Ile Tyr Phe
            100                 105                 110

Cys Lys Ile Glu Phe Met Tyr Pro Pro Pro Tyr Leu Asp Asn Glu Arg
        115                 120                 125

Ser Asn Gly Thr Ile Ile His Ile Lys Glu Lys His Leu Cys His Thr
    130                 135                 140

Gln Ser Ser Pro Lys Leu Phe Trp Ala Leu Val Val Val Ala Gly Val
145                 150                 155                 160

Leu Phe Cys Tyr Gly Leu Leu Val Thr Val Ala Leu Cys Val Ile Trp
                165                 170                 175

Thr Asn Ser Arg Arg Asn Arg Leu Leu Gln Ser Asp Tyr Met Asn Met
            180                 185                 190

Thr Pro Arg Arg Pro Gly Leu Thr Arg Lys Pro Tyr Gln Pro Tyr Ala
        195                 200                 205

Pro Ala Arg Asp Phe Ala Ala Tyr Arg Pro
    210                 215
```

<210> SEQ ID NO 27
<211> LENGTH: 660
<212> TYPE: DNA
<213> ORGANISM: Artificial Sequence
<220> FEATURE:
<221> NAME/KEY: source
<222> LOCATION: 1..660
<223> OTHER INFORMATION: /mol_type="unassigned DNA"
    /note="human full-length CD28"
    /organism="Artificial Sequence"
<220> FEATURE:
<221> NAME/KEY: CDS
<222> LOCATION: 1..660
<223> OTHER INFORMATION: /transl_table=1

<400> SEQUENCE: 27

```
atg ctg cgc ctg ctg ctg gcg ctg aac ctg ttt ccg agc att cag gtg      48
Met Leu Arg Leu Leu Leu Ala Leu Asn Leu Phe Pro Ser Ile Gln Val
```

```
                1               5                   10                  15
acc ggc aac aaa att ctg gtg aaa cag agc ccg atg ctg gtg gcg tat        96
Thr Gly Asn Lys Ile Leu Val Lys Gln Ser Pro Met Leu Val Ala Tyr
                20                  25                  30 gat aac gcg gtg aac ctg agc tgc aaa tat agc tat aac ctg ttt agc       144
Asp Asn Ala Val Asn Leu Ser Cys Lys Tyr Ser Tyr Asn Leu Phe Ser
                35                  40                  45 cgc gaa ttt cgc gcg agc ctg cat aaa ggc ctg gat agc gcg gtg gaa       192
Arg Glu Phe Arg Ala Ser Leu His Lys Gly Leu Asp Ser Ala Val Glu
        50                  55                  60 gtg tgc gtg gtg tat ggc aac tat agc cag cag ctg cag gtg tat agc       240
Val Cys Val Val Tyr Gly Asn Tyr Ser Gln Gln Leu Gln Val Tyr Ser
65                  70                  75                  80 aaa acc ggc ttt aac tgc gat ggc aaa ctg ggc aac gaa agc gtg acc       288
Lys Thr Gly Phe Asn Cys Asp Gly Lys Leu Gly Asn Glu Ser Val Thr
                85                  90                  95 ttt tat ctg cag aac ctg tat gtg aac cag acc gat att tat ttt tgc       336
Phe Tyr Leu Gln Asn Leu Tyr Val Asn Gln Thr Asp Ile Tyr Phe Cys
                100                 105                 110 aaa att gaa gtg atg tat ccg ccg ccg tat ctg gat aac gaa aaa agc       384
Lys Ile Glu Val Met Tyr Pro Pro Pro Tyr Leu Asp Asn Glu Lys Ser
                115                 120                 125 aac ggc acc att att cat gtg aaa ggc aaa cat ctg tgc ccg agc ccg       432
Asn Gly Thr Ile Ile His Val Lys Gly Lys His Leu Cys Pro Ser Pro
        130                 135                 140 ctg ttt ccg ggc ccg agc aaa ccg ttt tgg gtg ctg gtg gtg gtg ggc       480
Leu Phe Pro Gly Pro Ser Lys Pro Phe Trp Val Leu Val Val Val Gly
145                 150                 155                 160 ggc gtg ctg gcg tgc tat agc ctg ctg gtg acc gtg gcg ttt att att       528
Gly Val Leu Ala Cys Tyr Ser Leu Leu Val Thr Val Ala Phe Ile Ile
                165                 170                 175 ttt tgg gtg cgc agc aaa cgc agc cgc ctg ctg cat agc gat tat atg       576
Phe Trp Val Arg Ser Lys Arg Ser Arg Leu Leu His Ser Asp Tyr Met
                180                 185                 190 aac atg acc ccg cgc cgc ccg ggc ccg acc cgc aaa cat tat cag ccg       624
Asn Met Thr Pro Arg Arg Pro Gly Pro Thr Arg Lys His Tyr Gln Pro
                195                 200                 205 tat gcg ccg ccg cgc gat ttt gcg gcg tat cgc agc                       660
Tyr Ala Pro Pro Arg Asp Phe Ala Ala Tyr Arg Ser
        210                 215                 220
```

<210> SEQ ID NO 28
<211> LENGTH: 220
<212> TYPE: PRT
<213> ORGANISM: Artificial Sequence
<220> FEATURE:
<223> OTHER INFORMATION: [CDS]:1..660 from SEQ ID NO 27

<400> SEQUENCE: 28

```
Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
                20                  25                  30

Asp Asn Ala Val Asn Leu Ser Cys Lys Tyr Ser Tyr Asn Leu Phe Ser
                35                  40                  45

Arg Glu Phe Arg Ala Ser Leu His Lys Gly Leu Asp Ser Ala Val Glu
        50                  55                  60

Val Cys Val Val Tyr Gly Asn Tyr Ser Gln Gln Leu Gln Val Tyr Ser
65                  70                  75                  80
```

```
Lys Thr Gly Phe Asn Cys Asp Gly Lys Leu Gly Asn Glu Ser Val Thr
                 85                  90                  95
Phe Tyr Leu Gln Asn Leu Tyr Val Asn Gln Thr Asp Ile Tyr Phe Cys
            100                 105                 110
Lys Ile Glu Val Met Tyr Pro Pro Pro Tyr Leu Asp Asn Glu Lys Ser
        115                 120                 125
Asn Gly Thr Ile Ile His Val Lys Gly Lys His Leu Cys Pro Ser Pro
    130                 135                 140
Leu Phe Pro Gly Pro Ser Lys Pro Phe Trp Val Leu Val Val Val Gly
145                 150                 155                 160
Gly Val Leu Ala Cys Tyr Ser Leu Leu Val Thr Val Ala Phe Ile Ile
                165                 170                 175
Phe Trp Val Arg Ser Lys Arg Ser Arg Leu Leu His Ser Asp Tyr Met
            180                 185                 190
Asn Met Thr Pro Arg Arg Pro Gly Pro Thr Arg Lys His Tyr Gln Pro
        195                 200                 205
Tyr Ala Pro Pro Arg Asp Phe Ala Ala Tyr Arg Ser
    210                 215                 220
```

<210> SEQ ID NO 29
<211> LENGTH: 4
<212> TYPE: PRT
<213> ORGANISM: Artificial Sequence
<220> FEATURE:
<223> OTHER INFORMATION: CD28 domain (not mutated)

<400> SEQUENCE: 29

Tyr Met Asn Met
1

<210> SEQ ID NO 30
<211> LENGTH: 4
<212> TYPE: PRT
<213> ORGANISM: Artificial Sequence
<220> FEATURE:
<223> OTHER INFORMATION: CD28 domain (not mutated)

<400> SEQUENCE: 30

Pro Tyr Ala Pro
1

<210> SEQ ID NO 31
<211> LENGTH: 4
<212> TYPE: PRT
<213> ORGANISM: Artificial Sequence
<220> FEATURE:
<223> OTHER INFORMATION: CD28 domain (mutated)

<400> SEQUENCE: 31

Phe Met Asn Met
1

<210> SEQ ID NO 32
<211> LENGTH: 4
<212> TYPE: PRT
<213> ORGANISM: Artificial Sequence
<220> FEATURE:
<223> OTHER INFORMATION: CD28 domain (mutated)

<400> SEQUENCE: 32

Ala Tyr Ala Ala
1

```
<210> SEQ ID NO 33
<211> LENGTH: 870
<212> TYPE: DNA
<213> ORGANISM: Artificial Sequence
<220> FEATURE:
<221> NAME/KEY: source
<222> LOCATION: 1..870
<223> OTHER INFORMATION: /mol_type="unassigned DNA"
      /note="human PDL-1"
      /organism="Artificial Sequence"
<220> FEATURE:
<221> NAME/KEY: CDS
<222> LOCATION: 1..870
<223> OTHER INFORMATION: /transl_table=1

<400> SEQUENCE: 33 atg cgc att ttt gcg gtg ttt att ttt atg acc tat tgg cat ctg ctg    48
Met Arg Ile Phe Ala Val Phe Ile Phe Met Thr Tyr Trp His Leu Leu
1               5                   10                  15 aac gcg ttt acc gtg acc gtg ccg aaa gat ctg tat gtg gtg gaa tat    96
Asn Ala Phe Thr Val Thr Val Pro Lys Asp Leu Tyr Val Val Glu Tyr
                20                  25                  30 ggc agc aac atg acc att gaa tgc aaa ttt ccg gtg gaa aaa cag ctg    144
Gly Ser Asn Met Thr Ile Glu Cys Lys Phe Pro Val Glu Lys Gln Leu
            35                  40                  45 gat ctg gcg gcg ctg att gtg tat tgg gaa atg gaa gat aaa aac att    192
Asp Leu Ala Ala Leu Ile Val Tyr Trp Glu Met Glu Asp Lys Asn Ile
        50                  55                  60 att cag ttt gtg cat ggc gaa gaa gat ctg aaa gtg cag cat agc agc    240
Ile Gln Phe Val His Gly Glu Glu Asp Leu Lys Val Gln His Ser Ser
65                  70                  75                  80 tat cgc cag cgc gcg cgc ctg ctg aaa gat cag ctg agc ctg ggc aac    288
Tyr Arg Gln Arg Ala Arg Leu Leu Lys Asp Gln Leu Ser Leu Gly Asn
                85                  90                  95 gcg gcg ctg cag att acc gat gtg aaa ctg cag gat gcg ggc gtg tat    336
Ala Ala Leu Gln Ile Thr Asp Val Lys Leu Gln Asp Ala Gly Val Tyr
            100                 105                 110 cgc tgc atg att agc tat ggc ggc gcg gat tat aaa cgc att acc gtg    384
Arg Cys Met Ile Ser Tyr Gly Gly Ala Asp Tyr Lys Arg Ile Thr Val
        115                 120                 125 aaa gtg aac gcg ccg tat aac aaa att aac cag cgc att ctg gtg gtg    432
Lys Val Asn Ala Pro Tyr Asn Lys Ile Asn Gln Arg Ile Leu Val Val
    130                 135                 140 gat ccg gtg acc agc gaa cat gaa ctg acc tgc cag gcg gaa ggc tat    480
Asp Pro Val Thr Ser Glu His Glu Leu Thr Cys Gln Ala Glu Gly Tyr
145                 150                 155                 160 ccg aaa gcg gaa gtg att tgg acc agc agc gat cat cag gtg ctg agc    528
Pro Lys Ala Glu Val Ile Trp Thr Ser Ser Asp His Gln Val Leu Ser
                165                 170                 175 ggc aaa acc acc acc acc aac agc aaa cgc gaa gaa aaa ctg ttt aac    576
Gly Lys Thr Thr Thr Thr Asn Ser Lys Arg Glu Glu Lys Leu Phe Asn
            180                 185                 190 gtg acc agc acc ctg cgc att aac acc acc aac gaa att ttt tat        624
Val Thr Ser Thr Leu Arg Ile Asn Thr Thr Asn Glu Ile Phe Tyr
        195                 200                 205 tgc acc ttt cgc cgc ctg gat ccg gaa gaa aac cat acc gcg gaa ctg    672
Cys Thr Phe Arg Arg Leu Asp Pro Glu Glu Asn His Thr Ala Glu Leu
    210                 215                 220 gtg att ccg gaa ctg ccg ctg gcg cat ccg ccg aac gaa cgc acc cat    720
Val Ile Pro Glu Leu Pro Leu Ala His Pro Pro Asn Glu Arg Thr His
225                 230                 235                 240 ctg gtg att ctg ggc gcg att ctg ctg tgc ctg ggc gtg gcg ctg acc    768
Leu Val Ile Leu Gly Ala Ile Leu Leu Cys Leu Gly Val Ala Leu Thr
```

```
Leu Val Ile Leu Gly Ala Ile Leu Leu Cys Leu Gly Val Ala Leu Thr
                245                 250                 255 ttt att ttt cgc ctg cgc aaa ggc cgc atg atg gat gtg aaa aaa tgc      816
Phe Ile Phe Arg Leu Arg Lys Gly Arg Met Met Asp Val Lys Lys Cys
            260                 265                 270 ggc att cag gat acc aac agc aaa aaa cag agc gat acc cat ctg gaa      864
Gly Ile Gln Asp Thr Asn Ser Lys Lys Gln Ser Asp Thr His Leu Glu
            275                 280                 285 gaa acc                                                              870
Glu Thr
    290
```

<210> SEQ ID NO 34
<211> LENGTH: 290
<212> TYPE: PRT
<213> ORGANISM: Artificial Sequence
<220> FEATURE:
<223> OTHER INFORMATION: [CDS]:1..870 from SEQ ID NO 33

<400> SEQUENCE: 34

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285
```

```
Glu Thr
    290

<210> SEQ ID NO 35
<211> LENGTH: 819
<212> TYPE: DNA
<213> ORGANISM: Artificial Sequence
<220> FEATURE:
<221> NAME/KEY: source
<222> LOCATION: 1..819
<223> OTHER INFORMATION: /mol_type="unassigned DNA"
      /note="human PDL-2"
      /organism="Artificial Sequence"
<220> FEATURE:
<221> NAME/KEY: CDS
<222> LOCATION: 1..819
<223> OTHER INFORMATION: /transl_table=1

<400> SEQUENCE: 35 atg att ttt ctg ctg ctg atg ctg agc ctg gaa ctg cag ctg cat cag    48
Met Ile Phe Leu Leu Leu Met Leu Ser Leu Glu Leu Gln Leu His Gln
1               5                   10                  15 att gcg gcg ctg ttt acc gtg acc gtg ccg aaa gaa ctg tat att att    96
Ile Ala Ala Leu Phe Thr Val Thr Val Pro Lys Glu Leu Tyr Ile Ile
            20                  25                  30 gaa cat ggc agc aac gtg acc ctg gaa tgc aac ttt gat acc ggc agc    144
Glu His Gly Ser Asn Val Thr Leu Glu Cys Asn Phe Asp Thr Gly Ser
        35                  40                  45 cat gtg aac ctg ggc gcg att acc gcg agc ctg cag aaa gtg gaa aac    192
His Val Asn Leu Gly Ala Ile Thr Ala Ser Leu Gln Lys Val Glu Asn
    50                  55                  60 gat acc agc ccg cat cgc gaa cgc gcg acc ctg ctg gaa gaa cag ctg    240
Asp Thr Ser Pro His Arg Glu Arg Ala Thr Leu Leu Glu Glu Gln Leu
65                  70                  75                  80 ccg ctg ggc aaa gcg agc ttt cat att ccg cag gtg cag gtg cgc gat    288
Pro Leu Gly Lys Ala Ser Phe His Ile Pro Gln Val Gln Val Arg Asp
                85                  90                  95 gaa ggc cag tat cag tgc att att att tat ggc gtg gcg tgg gat tat    336
Glu Gly Gln Tyr Gln Cys Ile Ile Ile Tyr Gly Val Ala Trp Asp Tyr
            100                 105                 110 aaa tat ctg acc ctg aaa gtg aaa gcg agc tat cgc aaa att aac acc    384
Lys Tyr Leu Thr Leu Lys Val Lys Ala Ser Tyr Arg Lys Ile Asn Thr
        115                 120                 125 cat att ctg aaa gtg ccg gaa acc gat gaa gtg gaa ctg acc tgc cag    432
His Ile Leu Lys Val Pro Glu Thr Asp Glu Val Glu Leu Thr Cys Gln
    130                 135                 140 gcg acc ggc tat ccg ctg gcg gaa gtg agc tgg ccg aac gtg agc gtg    480
Ala Thr Gly Tyr Pro Leu Ala Glu Val Ser Trp Pro Asn Val Ser Val
145                 150                 155                 160 ccg gcg aac acc agc cat agc cgc acc ccg gaa ggc ctg tat cag gtg    528
Pro Ala Asn Thr Ser His Ser Arg Thr Pro Glu Gly Leu Tyr Gln Val
                165                 170                 175 acc agc gtg ctg cgc ctg aaa ccg ccg ccg ggc cgc aac ttt agc tgc    576
Thr Ser Val Leu Arg Leu Lys Pro Pro Pro Gly Arg Asn Phe Ser Cys
            180                 185                 190 gtg ttt tgg aac acc cat gtg cgc gaa ctg acc ctg gcg agc att gat    624
Val Phe Trp Asn Thr His Val Arg Glu Leu Thr Leu Ala Ser Ile Asp
        195                 200                 205 ctg cag agc cag atg gaa ccg cgc acc cat ccg acc tgg ctg ctg cat    672
Leu Gln Ser Gln Met Glu Pro Arg Thr His Pro Thr Trp Leu Leu His
    210                 215                 220 att ttt att ccg ttt tgc att att gcg ttt att ttt att gcg acc gtg    720
Ile Phe Ile Pro Phe Cys Ile Ile Ala Phe Ile Phe Ile Ala Thr Val
```

```
                225                 230                 235                 240 att gcg ctg cgc aaa cag ctg tgc cag aaa ctg tat agc agc aaa gat       768
Ile Ala Leu Arg Lys Gln Leu Cys Gln Lys Leu Tyr Ser Ser Lys Asp
                245                 250                 255 acc acc aaa cgc ccg gtg acc acc acc aaa cgc gaa gtg aac agc gcg       816
Thr Thr Lys Arg Pro Val Thr Thr Thr Lys Arg Glu Val Asn Ser Ala
            260                 265                 270 att                                                                   819
Ile

<210> SEQ ID NO 36
<211> LENGTH: 273
<212> TYPE: PRT
<213> ORGANISM: Artificial Sequence
<220> FEATURE:
<223> OTHER INFORMATION: [CDS]:1..819 from SEQ ID NO 35

<400> SEQUENCE: 36
```

Met Ile Phe Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
                20                  25                  30

Glu His Gly Ser Asn Val Thr Leu Glu Cys Asn Phe Asp Thr Gly Ser
                35                  40                  45

His Val Asn Leu Gly Ala Ile Thr Ala Ser Leu Gln Lys Val Glu Asn
            50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
                100                 105                 110

Lys Tyr Leu Thr Leu Lys Val Lys Ala Ser Tyr Arg Lys Ile Asn Thr
            115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Trp Leu Leu His
    210                 215                 220

Ile Phe Ile Pro Phe Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
                245                 250                 255

Thr Thr Lys Arg Pro Val Thr Thr Thr Lys Arg Glu Val Asn Ser Ala
            260                 265                 270

Ile

```
<210> SEQ ID NO 37
<211> LENGTH: 870
```

```
<212> TYPE: DNA
<213> ORGANISM: Artificial Sequence
<220> FEATURE:
<221> NAME/KEY: source
<222> LOCATION: 1..870
<223> OTHER INFORMATION: /mol_type="unassigned DNA"
      /note="full length murine PD-L1 (recombinant murine)"
      /organism="Artificial Sequence"
<220> FEATURE:
<221> NAME/KEY: CDS
<222> LOCATION: 1..870
<223> OTHER INFORMATION: /transl_table=1

<400> SEQUENCE: 37 atg cgc att ttt gcg ggc att att ttt acc gcg tgc tgc cat ctg ctg      48
Met Arg Ile Phe Ala Gly Ile Ile Phe Thr Ala Cys Cys His Leu Leu
 1               5                  10                  15 cgc gcg ttt acc att acc gcg ccg aaa gat ctg tat gtg gtg gaa tat      96
Arg Ala Phe Thr Ile Thr Ala Pro Lys Asp Leu Tyr Val Val Glu Tyr
                20                  25                  30 ggc agc aac gtg acc atg gaa tgc cgc ttt ccg gtg gaa cgc gaa ctg     144
Gly Ser Asn Val Thr Met Glu Cys Arg Phe Pro Val Glu Arg Glu Leu
            35                  40                  45 gat ctg ctg gcg ctg gtg gtg tat tgg gaa aaa gaa gat gaa cag gtg     192
Asp Leu Leu Ala Leu Val Val Tyr Trp Glu Lys Glu Asp Glu Gln Val
50                  55                  60 att cag ttt gtg gcg ggc gaa gaa gat ctg aaa ccg cag cat agc aac     240
Ile Gln Phe Val Ala Gly Glu Glu Asp Leu Lys Pro Gln His Ser Asn
65                  70                  75                  80 ttt cgc ggc cgc gcg agc ctg ccg aaa gat cag ctg ctg aaa ggc aac     288
Phe Arg Gly Arg Ala Ser Leu Pro Lys Asp Gln Leu Leu Lys Gly Asn
                85                  90                  95 gcg gcg ctg cag att acc gat gtg aaa ctg cag gat gcg ggc gtg tat     336
Ala Ala Leu Gln Ile Thr Asp Val Lys Leu Gln Asp Ala Gly Val Tyr
            100                 105                 110 tgc tgc att att agc tat ggc ggc gcg gat tat aaa cgc att acc ctg     384
Cys Cys Ile Ile Ser Tyr Gly Gly Ala Asp Tyr Lys Arg Ile Thr Leu
        115                 120                 125 aaa gtg aac gcg ccg tat cgc aaa att aac cag cgc att agc gtg gat     432
Lys Val Asn Ala Pro Tyr Arg Lys Ile Asn Gln Arg Ile Ser Val Asp
130                 135                 140 ccg gcg acc agc gaa cat gaa ctg att tgc cag gcg gaa ggc tat ccg     480
Pro Ala Thr Ser Glu His Glu Leu Ile Cys Gln Ala Glu Gly Tyr Pro
145                 150                 155                 160 gaa gcg gaa gtg att tgg acc aac agc gat cat cag ccg gtg agc ggc     528
Glu Ala Glu Val Ile Trp Thr Asn Ser Asp His Gln Pro Val Ser Gly
                165                 170                 175 aaa cgc agc gtg acc acc agc cgc acc gaa ggc atg ctg ctg aac gtg     576
Lys Arg Ser Val Thr Thr Ser Arg Thr Glu Gly Met Leu Leu Asn Val
            180                 185                 190 acc agc agc ctg cgc gtg aac gcg acc gcg aac gat gtg ttt tat tgc     624
Thr Ser Ser Leu Arg Val Asn Ala Thr Ala Asn Asp Val Phe Tyr Cys
        195                 200                 205 acc ttt tgg cgc agc cag ccg ggc cag aac cat acc gcg gaa ctg att     672
Thr Phe Trp Arg Ser Gln Pro Gly Gln Asn His Thr Ala Glu Leu Ile
    210                 215                 220 att ccg gaa ctg ccg gcg acc cat ccg ccg cag aac cgc acc cat tgg     720
Ile Pro Glu Leu Pro Ala Thr His Pro Pro Gln Asn Arg Thr His Trp
225                 230                 235                 240 gtg ctg ctg ggc agc att ctg ctg ttt ctg att gtg gtg agc acc gtg     768
Val Leu Leu Gly Ser Ile Leu Leu Phe Leu Ile Val Val Ser Thr Val
                245                 250                 255
```

```
ctg ctg ttt ctg cgc aaa cag gtg cgc atg ctg gat gtg gaa aaa tgc     816
Leu Leu Phe Leu Arg Lys Gln Val Arg Met Leu Asp Val Glu Lys Cys
            260             265                 270 ggc gtg gaa gat acc agc agc aaa aac cgc aac gat acc cag ttt gaa     864
Gly Val Glu Asp Thr Ser Ser Lys Asn Arg Asn Asp Thr Gln Phe Glu
        275                 280                 285 gaa acc                                                             870
Glu Thr
    290
```

<210> SEQ ID NO 38
<211> LENGTH: 290
<212> TYPE: PRT
<213> ORGANISM: Artificial Sequence
<220> FEATURE:
<223> OTHER INFORMATION: [CDS]:1..870 from SEQ ID NO 37

<400> SEQUENCE: 38

```
Met Arg Ile Phe Ala Gly Ile Ile Phe Thr Ala Cys Cys His Leu Leu
1               5                   10                  15

Arg Ala Phe Thr Ile Thr Ala Pro Lys Asp Leu Tyr Val Val Glu Tyr
            20                  25                  30

Gly Ser Asn Val Thr Met Glu Cys Arg Phe Pro Val Glu Arg Glu Leu
        35                  40                  45

Asp Leu Leu Ala Leu Val Val Tyr Trp Glu Lys Glu Asp Glu Gln Val
    50                  55                  60

Ile Gln Phe Val Ala Gly Glu Glu Asp Leu Lys Pro Gln His Ser Asn
65                  70                  75                  80

Phe Arg Gly Arg Ala Ser Leu Pro Lys Asp Gln Leu Leu Lys Gly Asn
                85                  90                  95

Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
        115                 120                 125

Lys Val Asn Ala Pro Tyr Arg Lys Ile Asn Gln Arg Ile Ser Val Asp
    130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
            180                 185                 190

Thr Ser Ser Leu Arg Val Asn Ala Thr Ala Asn Asp Val Phe Tyr Cys
        195                 200                 205

Thr Phe Trp Arg Ser Gln Pro Gly Gln Asn His Thr Ala Glu Leu Ile
    210                 215                 220

Ile Pro Glu Leu Pro Ala Thr His Pro Pro Gln Asn Arg Thr His Trp
225                 230                 235                 240

Val Leu Leu Gly Ser Ile Leu Leu Phe Leu Ile Val Val Ser Thr Val
                245                 250                 255

Leu Leu Phe Leu Arg Lys Gln Val Arg Met Leu Asp Val Glu Lys Cys
            260                 265                 270

Gly Val Glu Asp Thr Ser Ser Lys Asn Arg Asn Asp Thr Gln Phe Glu
        275                 280                 285

Glu Thr
    290
```

<210> SEQ ID NO 39
<211> LENGTH: 507
<212> TYPE: DNA
<213> ORGANISM: Artificial Sequence
<220> FEATURE:
<221> NAME/KEY: source
<222> LOCATION: 1..507
<223> OTHER INFORMATION: /mol_type="unassigned DNA"
      /note="murine PD-1 (AA1-169) (CTM construct)"
      /organism="Artificial Sequence"
<220> FEATURE:
<221> NAME/KEY: CDS
<222> LOCATION: 1..507
<223> OTHER INFORMATION: /transl_table=1

<400> SEQUENCE: 39

```
atg tgg gtg cgc cag gtg ccg tgg agc ttt acc tgg gcg gtg ctg cag      48
Met Trp Val Arg Gln Val Pro Trp Ser Phe Thr Trp Ala Val Leu Gln
 1               5                  10                  15 ctg agc tgg cag agc ggc tgg ctg ctg gaa gtg ccg aac ggc ccg tgg      96
Leu Ser Trp Gln Ser Gly Trp Leu Leu Glu Val Pro Asn Gly Pro Trp
             20                  25                  30 cgc agc ctg acc ttt tat ccg gcg tgg ctg acc gtg agc gaa ggc gcg     144
Arg Ser Leu Thr Phe Tyr Pro Ala Trp Leu Thr Val Ser Glu Gly Ala
         35                  40                  45 aac gcg acc ttt acc tgc agc ctg agc aac tgg agc gaa gat ctg atg     192
Asn Ala Thr Phe Thr Cys Ser Leu Ser Asn Trp Ser Glu Asp Leu Met
     50                  55                  60 ctg aac tgg aac cgc ctg agc ccg agc aac cag acc gaa aaa cag gcg     240
Leu Asn Trp Asn Arg Leu Ser Pro Ser Asn Gln Thr Glu Lys Gln Ala
 65                  70                  75                  80 gcg ttt tgc aac ggc ctg agc cag ccg gtg cag gat gcg cgc ttt cag     288
Ala Phe Cys Asn Gly Leu Ser Gln Pro Val Gln Asp Ala Arg Phe Gln
                 85                  90                  95 att att cag ctg ccg aac cgc cat gat ttt cat atg aac att ctg gat     336
Ile Ile Gln Leu Pro Asn Arg His Asp Phe His Met Asn Ile Leu Asp
            100                 105                 110 acc cgc cgc aac gat agc ggc att tat ctg tgc ggc gcg att agc ctg     384
Thr Arg Arg Asn Asp Ser Gly Ile Tyr Leu Cys Gly Ala Ile Ser Leu
        115                 120                 125 cat ccg aaa gcg aaa att gaa gaa agc ccg ggc gcg gaa ctg gtg gtg     432
His Pro Lys Ala Lys Ile Glu Glu Ser Pro Gly Ala Glu Leu Val Val
    130                 135                 140 acc gaa cgc att ctg gaa acc agc acc cgc tat ccg agc ccg agc ccg     480
Thr Glu Arg Ile Leu Glu Thr Ser Thr Arg Tyr Pro Ser Pro Ser Pro
145                 150                 155                 160 aaa ccg gaa ggc cgc ttt cag ggc atg                                  507
Lys Pro Glu Gly Arg Phe Gln Gly Met
                165
```

<210> SEQ ID NO 40
<211> LENGTH: 169
<212> TYPE: PRT
<213> ORGANISM: Artificial Sequence
<220> FEATURE:
<223> OTHER INFORMATION: [CDS]:1..507 from SEQ ID NO 39

<400> SEQUENCE: 40

```
Met Trp Val Arg Gln Val Pro Trp Ser Phe Thr Trp Ala Val Leu Gln
 1               5                  10                  15

Leu Ser Trp Gln Ser Gly Trp Leu Leu Glu Val Pro Asn Gly Pro Trp
             20                  25                  30

Arg Ser Leu Thr Phe Tyr Pro Ala Trp Leu Thr Val Ser Glu Gly Ala
```

```
                35                  40                  45
Asn Ala Thr Phe Thr Cys Ser Leu Ser Asn Trp Ser Glu Asp Leu Met
 50                  55                  60

Leu Asn Trp Asn Arg Leu Ser Pro Ser Asn Gln Thr Glu Lys Gln Ala
 65                  70                  75                  80

Ala Phe Cys Asn Gly Leu Ser Gln Pro Val Gln Asp Ala Arg Phe Gln
                 85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met
                165
```

<210> SEQ ID NO 41
<211> LENGTH: 204
<212> TYPE: DNA
<213> ORGANISM: Artificial Sequence
<220> FEATURE:
<221> NAME/KEY: source
<222> LOCATION: 1..204
<223> OTHER INFORMATION: /mol_type="unassigned DNA"
      /note="murine CD28 (AA151-218) (CTM construct)"
      /organism="Artificial Sequence"
<220> FEATURE:
<221> NAME/KEY: CDS
<222> LOCATION: 1..204
<223> OTHER INFORMATION: /transl_table=1

<400> SEQUENCE: 41

```
ttt tgg gcg ctg gtg gtg gtg gcg ggc gtg ctg ttt tgc tat ggc ctg      48
Phe Trp Ala Leu Val Val Val Ala Gly Val Leu Phe Cys Tyr Gly Leu
 1               5                  10                  15 ctg gtg acc gtg gcg ctg tgc gtg att tgg acc aac agc cgc cgc aac      96
Leu Val Thr Val Ala Leu Cys Val Ile Trp Thr Asn Ser Arg Arg Asn
             20                  25                  30 cgc ctg ctg cag agc gat tat atg aac atg acc ccg cgc cgc ccg ggc     144
Arg Leu Leu Gln Ser Asp Tyr Met Asn Met Thr Pro Arg Arg Pro Gly
         35                  40                  45 ctg acc cgc aaa ccg tat cag ccg tat gcg ccg gcg cgc gat ttt gcg     192
Leu Thr Arg Lys Pro Tyr Gln Pro Tyr Ala Pro Ala Arg Asp Phe Ala
     50                  55                  60 gcg tat cgc ccg                                                     204
Ala Tyr Arg Pro
 65
```

<210> SEQ ID NO 42
<211> LENGTH: 68
<212> TYPE: PRT
<213> ORGANISM: Artificial Sequence
<220> FEATURE:
<223> OTHER INFORMATION: [CDS]:1..204 from SEQ ID NO 41

<400> SEQUENCE: 42

```
Phe Trp Ala Leu Val Val Val Ala Gly Val Leu Phe Cys Tyr Gly Leu
 1               5                  10                  15

Leu Val Thr Val Ala Leu Cys Val Ile Trp Thr Asn Ser Arg Arg Asn
             20                  25                  30
```

```
Arg Leu Leu Gln Ser Asp Tyr Met Asn Met Thr Pro Arg Arg Pro Gly
            35                  40                  45

Leu Thr Arg Lys Pro Tyr Gln Pro Tyr Ala Pro Ala Arg Asp Phe Ala
 50                  55                  60

Ala Tyr Arg Pro
 65

<210> SEQ ID NO 43
<211> LENGTH: 711
<212> TYPE: DNA
<213> ORGANISM: Artificial Sequence
<220> FEATURE:
<221> NAME/KEY: source
<222> LOCATION: 1..711
<223> OTHER INFORMATION: /mol_type="unassigned DNA"
      /note="murine PD1-CD28 (CTM construct)"
      /organism="Artificial Sequence"
<220> FEATURE:
<221> NAME/KEY: CDS
<222> LOCATION: 1..711
<223> OTHER INFORMATION: /transl_table=1

<400> SEQUENCE: 43
```

| | |
|---|---|
| atg tgg gtg cgc cag gtg ccg tgg agc ttt acc tgg gcg gtg ctg cag<br>Met Trp Val Arg Gln Val Pro Trp Ser Phe Thr Trp Ala Val Leu Gln<br>1               5                   10                  15 | 48 |
| ctg agc tgg cag agc ggc tgg ctg ctg gaa gtg ccg aac ggc ccg tgg<br>Leu Ser Trp Gln Ser Gly Trp Leu Leu Glu Val Pro Asn Gly Pro Trp<br>            20                  25                  30 | 96 |
| cgc agc ctg acc ttt tat ccg gcg tgg ctg acc gtg agc gaa ggc gcg<br>Arg Ser Leu Thr Phe Tyr Pro Ala Trp Leu Thr Val Ser Glu Gly Ala<br>        35                  40                  45 | 144 |
| aac gcg acc ttt acc tgc agc ctg agc aac tgg agc gaa gat ctg atg<br>Asn Ala Thr Phe Thr Cys Ser Leu Ser Asn Trp Ser Glu Asp Leu Met<br>    50                  55                  60 | 192 |
| ctg aac tgg aac cgc ctg agc ccg agc aac cag acc gaa aaa cag gcg<br>Leu Asn Trp Asn Arg Leu Ser Pro Ser Asn Gln Thr Glu Lys Gln Ala<br>65                  70                  75                  80 | 240 |
| gcg ttt tgc aac ggc ctg agc cag ccg gtg cag gat gcg cgc ttt cag<br>Ala Phe Cys Asn Gly Leu Ser Gln Pro Val Gln Asp Ala Arg Phe Gln<br>                85                  90                  95 | 288 |
| att att cag ctg ccg aac cgc cat gat ttt cat atg aac att ctg gat<br>Ile Ile Gln Leu Pro Asn Arg His Asp Phe His Met Asn Ile Leu Asp<br>            100                 105                 110 | 336 |
| acc cgc cgc aac gat agc ggc att tat ctg tgc ggc gcg att agc ctg<br>Thr Arg Arg Asn Asp Ser Gly Ile Tyr Leu Cys Gly Ala Ile Ser Leu<br>        115                 120                 125 | 384 |
| cat ccg aaa gcg aaa att gaa gaa agc ccg ggc gcg gaa ctg gtg gtg<br>His Pro Lys Ala Lys Ile Glu Glu Ser Pro Gly Ala Glu Leu Val Val<br>    130                 135                 140 | 432 |
| acc gaa cgc att ctg gaa acc agc acc cgc tat ccg agc ccg agc ccg<br>Thr Glu Arg Ile Leu Glu Thr Ser Thr Arg Tyr Pro Ser Pro Ser Pro<br>145                 150                 155                 160 | 480 |
| aaa ccg gaa ggc cgc ttt cag ggc atg ttt tgg gcg ctg gtg gtg gtg<br>Lys Pro Glu Gly Arg Phe Gln Gly Met Phe Trp Ala Leu Val Val Val<br>                165                 170                 175 | 528 |
| gcg ggc gtg ctg ttt tgc tat ggc ctg ctg gtg acc gtg gcg ctg tgc<br>Ala Gly Val Leu Phe Cys Tyr Gly Leu Leu Val Thr Val Ala Leu Cys<br>            180                 185                 190 | 576 |
| gtg att tgg acc aac agc cgc cgc aac cgc ctg ctg cag agc gat tat<br>Val Ile Trp Thr Asn Ser Arg Arg Asn Arg Leu Leu Gln Ser Asp Tyr<br>        195                 200                 205 | 624 |

```
atg aac atg acc ccg cgc cgc ccg ggc ctg acc cgc aaa ccg tat cag      672
Met Asn Met Thr Pro Arg Arg Pro Gly Leu Thr Arg Lys Pro Tyr Gln
    210                 215                 220 ccg tat gcg ccg gcg cgc gat ttt gcg gcg tat cgc ccg                  711
Pro Tyr Ala Pro Ala Arg Asp Phe Ala Ala Tyr Arg Pro
225                 230                 235
```

<210> SEQ ID NO 44
<211> LENGTH: 237
<212> TYPE: PRT
<213> ORGANISM: Artificial Sequence
<220> FEATURE:
<223> OTHER INFORMATION: [CDS]:1..711 from SEQ ID NO 43

<400> SEQUENCE: 44

```
Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Phe Trp Ala Leu Val Val Val
                165                 170                 175

Ala Gly Val Leu Phe Cys Tyr Gly Leu Leu Val Thr Val Ala Leu Cys
            180                 185                 190

Val Ile Trp Thr Asn Ser Arg Arg Asn Arg Leu Leu Gln Ser Asp Tyr
        195                 200                 205

Met Asn Met Thr Pro Arg Arg Pro Gly Leu Thr Arg Lys Pro Tyr Gln
    210                 215                 220

Pro Tyr Ala Pro Ala Arg Asp Phe Ala Ala Tyr Arg Pro
225                 230                 235
```

<210> SEQ ID NO 45
<211> LENGTH: 507
<212> TYPE: DNA
<213> ORGANISM: Artificial Sequence
<220> FEATURE:
<221> NAME/KEY: source
<222> LOCATION: 1..507
<223> OTHER INFORMATION: /mol_type="unassigned DNA"
      /note="murine PD1 (AA1-169) (CEX construct)"
      /organism="Artificial Sequence"
<220> FEATURE:
<221> NAME/KEY: CDS
<222> LOCATION: 1..507
<223> OTHER INFORMATION: /transl_table=1

<400> SEQUENCE: 45

```
atg tgg gtg cgc cag gtg ccg tgg agc ttt acc tgg gcg gtg ctg cag        48
Met Trp Val Arg Gln Val Pro Trp Ser Phe Thr Trp Ala Val Leu Gln
1               5                   10                  15 ctg agc tgg cag agc ggc tgg ctg ctg gaa gtg ccg aac ggc ccg tgg        96
Leu Ser Trp Gln Ser Gly Trp Leu Leu Glu Val Pro Asn Gly Pro Trp
            20                  25                  30 cgc agc ctg acc ttt tat ccg gcg tgg ctg acc gtg agc gaa ggc gcg       144
Arg Ser Leu Thr Phe Tyr Pro Ala Trp Leu Thr Val Ser Glu Gly Ala
        35                  40                  45 aac gcg acc ttt acc tgc agc ctg agc aac tgg agc gaa gat ctg atg       192
Asn Ala Thr Phe Thr Cys Ser Leu Ser Asn Trp Ser Glu Asp Leu Met
50                  55                  60 ctg aac tgg aac cgc ctg agc ccg agc aac cag acc gaa aaa cag gcg       240
Leu Asn Trp Asn Arg Leu Ser Pro Ser Asn Gln Thr Glu Lys Gln Ala
65                  70                  75                  80 gcg ttt tgc aac ggc ctg agc cag ccg gtg cag gat gcg cgc ttt cag       288
Ala Phe Cys Asn Gly Leu Ser Gln Pro Val Gln Asp Ala Arg Phe Gln
                85                  90                  95 att att cag ctg ccg aac cgc cat gat ttt cat atg aac att ctg gat       336
Ile Ile Gln Leu Pro Asn Arg His Asp Phe His Met Asn Ile Leu Asp
            100                 105                 110 acc cgc cgc aac gat agc ggc att tat ctg tgc ggc gcg att agc ctg       384
Thr Arg Arg Asn Asp Ser Gly Ile Tyr Leu Cys Gly Ala Ile Ser Leu
        115                 120                 125 cat ccg aaa gcg aaa att gaa gaa agc ccg ggc gcg gaa ctg gtg gtg       432
His Pro Lys Ala Lys Ile Glu Glu Ser Pro Gly Ala Glu Leu Val Val
    130                 135                 140 acc gaa cgc att ctg gaa acc agc acc cgc tat ccg agc ccg agc ccg       480
Thr Glu Arg Ile Leu Glu Thr Ser Thr Arg Tyr Pro Ser Pro Ser Pro
145                 150                 155                 160 aaa ccg gaa ggc cgc ttt cag ggc atg                                   507
Lys Pro Glu Gly Arg Phe Gln Gly Met
                165
```

<210> SEQ ID NO 46
<211> LENGTH: 169
<212> TYPE: PRT
<213> ORGANISM: Artificial Sequence
<220> FEATURE:
<223> OTHER INFORMATION: [CDS]:1..507 from SEQ ID NO 45

<400> SEQUENCE: 46

```
Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
```

```
                    115                 120                 125
His Pro Lys Ala Lys Ile Glu Glu Ser Pro Gly Ala Glu Leu Val Val
            130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met
                165
```

<210> SEQ ID NO 47
<211> LENGTH: 312
<212> TYPE: DNA
<213> ORGANISM: Artificial Sequence
<220> FEATURE:
<221> NAME/KEY: source
<222> LOCATION: 1..312
<223> OTHER INFORMATION: /mol_type="unassigned DNA"
      /note="murine CD28 (AA115-218) (CEX construct)"
      /organism="Artificial Sequence"
<220> FEATURE:
<221> NAME/KEY: CDS
<222> LOCATION: 1..312
<223> OTHER INFORMATION: /transl_table=1

<400> SEQUENCE: 47

```
att gaa ttt atg tat ccg ccg ccg tat ctg gat aac gaa cgc agc aac      48
Ile Glu Phe Met Tyr Pro Pro Pro Tyr Leu Asp Asn Glu Arg Ser Asn
1               5                   10                  15 ggc acc att att cat att aaa gaa aaa cat ctg tgc cat acc cag agc      96
Gly Thr Ile Ile His Ile Lys Glu Lys His Leu Cys His Thr Gln Ser
            20                  25                  30 agc ccg aaa ctg ttt tgg gcg ctg gtg gtg gtg gcg ggc gtg ctg ttt     144
Ser Pro Lys Leu Phe Trp Ala Leu Val Val Val Ala Gly Val Leu Phe
        35                  40                  45 tgc tat ggc ctg ctg gtg acc gtg gcg ctg tgc gtg att tgg acc aac     192
Cys Tyr Gly Leu Leu Val Thr Val Ala Leu Cys Val Ile Trp Thr Asn
    50                  55                  60 agc cgc cgc aac cgc ctg ctg cag agc gat tat atg aac atg acc ccg     240
Ser Arg Arg Asn Arg Leu Leu Gln Ser Asp Tyr Met Asn Met Thr Pro
65                  70                  75                  80 cgc cgc ccg ggc ctg acc cgc aaa ccg tat cag ccg tat gcg ccg gcg     288
Arg Arg Pro Gly Leu Thr Arg Lys Pro Tyr Gln Pro Tyr Ala Pro Ala
                85                  90                  95 cgc gat ttt gcg gcg tat cgc ccg                                     312
Arg Asp Phe Ala Ala Tyr Arg Pro
                100
```

<210> SEQ ID NO 48
<211> LENGTH: 104
<212> TYPE: PRT
<213> ORGANISM: Artificial Sequence
<220> FEATURE:
<223> OTHER INFORMATION: [CDS]:1..312 from SEQ ID NO 47

<400> SEQUENCE: 48

```
Ile Glu Phe Met Tyr Pro Pro Pro Tyr Leu Asp Asn Glu Arg Ser Asn
1               5                   10                  15

Gly Thr Ile Ile His Ile Lys Glu Lys His Leu Cys His Thr Gln Ser
            20                  25                  30

Ser Pro Lys Leu Phe Trp Ala Leu Val Val Val Ala Gly Val Leu Phe
        35                  40                  45

Cys Tyr Gly Leu Leu Val Thr Val Ala Leu Cys Val Ile Trp Thr Asn
    50                  55                  60
```

```
Ser Arg Arg Asn Arg Leu Leu Gln Ser Asp Tyr Met Asn Met Thr Pro
 65                  70                  75                  80

Arg Arg Pro Gly Leu Thr Arg Lys Pro Tyr Gln Pro Tyr Ala Pro Ala
                 85                  90                  95

Arg Asp Phe Ala Ala Tyr Arg Pro
            100
```

<210> SEQ ID NO 49
<211> LENGTH: 819
<212> TYPE: DNA
<213> ORGANISM: Artificial Sequence
<220> FEATURE:
<221> NAME/KEY: source
<222> LOCATION: 1..819
<223> OTHER INFORMATION: /mol_type="unassigned DNA"
      /note="murine PD1-CD28 (CEX construct)"
      /organism="Artificial Sequence"
<220> FEATURE:
<221> NAME/KEY: CDS
<222> LOCATION: 1..819
<223> OTHER INFORMATION: /transl_table=1

<400> SEQUENCE: 49

```
atg tgg gtg cgc cag gtg ccg tgg agc ttt acc tgg gcg gtg ctg cag     48
Met Trp Val Arg Gln Val Pro Trp Ser Phe Thr Trp Ala Val Leu Gln
 1               5                  10                  15 ctg agc tgg cag agc ggc tgg ctg ctg gaa gtg ccg aac ggc ccg tgg     96
Leu Ser Trp Gln Ser Gly Trp Leu Leu Glu Val Pro Asn Gly Pro Trp
             20                  25                  30 cgc agc ctg acc ttt tat ccg gcg tgg ctg acc gtg agc gaa ggc gcg    144
Arg Ser Leu Thr Phe Tyr Pro Ala Trp Leu Thr Val Ser Glu Gly Ala
         35                  40                  45 aac gcg acc ttt acc tgc agc ctg agc aac tgg agc gaa gat ctg atg    192
Asn Ala Thr Phe Thr Cys Ser Leu Ser Asn Trp Ser Glu Asp Leu Met
     50                  55                  60 ctg aac tgg aac cgc ctg agc ccg agc aac cag acc gaa aaa cag gcg    240
Leu Asn Trp Asn Arg Leu Ser Pro Ser Asn Gln Thr Glu Lys Gln Ala
 65                  70                  75                  80 gcg ttt tgc aac ggc ctg agc cag ccg gtg cag gat gcg cgc ttt cag    288
Ala Phe Cys Asn Gly Leu Ser Gln Pro Val Gln Asp Ala Arg Phe Gln
                 85                  90                  95 att att cag ctg ccg aac cgc cat gat ttt cat atg aac att ctg gat    336
Ile Ile Gln Leu Pro Asn Arg His Asp Phe His Met Asn Ile Leu Asp
            100                 105                 110 acc cgc cgc aac gat agc ggc att tat ctg tgc ggc gcg att agc ctg    384
Thr Arg Arg Asn Asp Ser Gly Ile Tyr Leu Cys Gly Ala Ile Ser Leu
        115                 120                 125 cat ccg aaa gcg aaa att gaa gaa agc ccg ggc gcg gaa ctg gtg gtg    432
His Pro Lys Ala Lys Ile Glu Glu Ser Pro Gly Ala Glu Leu Val Val
    130                 135                 140 acc gaa cgc att ctg gaa acc agc acc cgc tat ccg agc ccg agc ccg    480
Thr Glu Arg Ile Leu Glu Thr Ser Thr Arg Tyr Pro Ser Pro Ser Pro
145                 150                 155                 160 aaa ccg gaa ggc cgc ttt cag ggc atg att gaa ttt atg tat ccg ccg    528
Lys Pro Glu Gly Arg Phe Gln Gly Met Ile Glu Phe Met Tyr Pro Pro
                165                 170                 175 ccg tat ctg gat aac gaa cgc agc aac ggc acc att att cat att aaa    576
Pro Tyr Leu Asp Asn Glu Arg Ser Asn Gly Thr Ile Ile His Ile Lys
            180                 185                 190 gaa aaa cat ctg tgc cat acc cag agc agc ccg aaa ctg ttt tgg gcg    624
Glu Lys His Leu Cys His Thr Gln Ser Ser Pro Lys Leu Phe Trp Ala
        195                 200                 205
```

```
ctg gtg gtg gtg gcg ggc gtg ctg ttt tgc tat ggc ctg ctg gtg acc      672
Leu Val Val Val Ala Gly Val Leu Phe Cys Tyr Gly Leu Leu Val Thr
    210             215                 220 gtg gcg ctg tgc gtg att tgg acc aac agc cgc cgc aac cgc ctg ctg      720
Val Ala Leu Cys Val Ile Trp Thr Asn Ser Arg Arg Asn Arg Leu Leu
225             230                 235                 240 cag agc gat tat atg aac atg acc ccg cgc cgc ccg ggc ctg acc cgc      768
Gln Ser Asp Tyr Met Asn Met Thr Pro Arg Arg Pro Gly Leu Thr Arg
            245                 250                 255 aaa ccg tat cag ccg tat gcg ccg gcg cgc gat ttt gcg gcg tat cgc      816
Lys Pro Tyr Gln Pro Tyr Ala Pro Ala Arg Asp Phe Ala Ala Tyr Arg
                260                 265                 270 ccg                                                                   819
Pro

<210> SEQ ID NO 50
<211> LENGTH: 273
<212> TYPE: PRT
<213> ORGANISM: Artificial Sequence
<220> FEATURE:
<223> OTHER INFORMATION: [CDS]:1..819 from SEQ ID NO 49

<400> SEQUENCE: 50

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Ile Glu Phe Met Tyr Pro Pro
                165                 170                 175

Pro Tyr Leu Asp Asn Glu Arg Ser Asn Gly Thr Ile Ile His Ile Lys
            180                 185                 190

Glu Lys His Leu Cys His Thr Gln Ser Ser Pro Lys Leu Phe Trp Ala
        195                 200                 205

Leu Val Val Val Ala Gly Val Leu Phe Cys Tyr Gly Leu Leu Val Thr
    210                 215                 220

Val Ala Leu Cys Val Ile Trp Thr Asn Ser Arg Arg Asn Arg Leu Leu
225                 230                 235                 240

Gln Ser Asp Tyr Met Asn Met Thr Pro Arg Arg Pro Gly Leu Thr Arg
                245                 250                 255

Lys Pro Tyr Gln Pro Tyr Ala Pro Ala Arg Asp Phe Ala Ala Tyr Arg
            260                 265                 270
```

Pro

<210> SEQ ID NO 51
<211> LENGTH: 693
<212> TYPE: DNA
<213> ORGANISM: Artificial Sequence
<220> FEATURE:
<221> NAME/KEY: source
<222> LOCATION: 1..693
<223> OTHER INFORMATION: /mol_type="unassigned DNA"
      /note="PTM-FMNM construct (murine)"
      /organism="Artificial Sequence"
<220> FEATURE:
<221> NAME/KEY: CDS
<222> LOCATION: 1..693
<223> OTHER INFORMATION: /transl_table=1

<400> SEQUENCE: 51

| | | | | | | | | | | | | | | | | |
|---|---|---|---|---|---|---|---|---|---|---|---|---|---|---|---|---|
| atg | tgg | gtg | cgc | cag | gtg | ccg | tgg | agc | ttt | acc | tgg | gcg | gtg | ctg | cag | 48 |
| Met | Trp | Val | Arg | Gln | Val | Pro | Trp | Ser | Phe | Thr | Trp | Ala | Val | Leu | Gln | |
| 1 | | | | 5 | | | | | 10 | | | | | 15 | | |

| ctg | agc | tgg | cag | agc | ggc | tgg | ctg | ctg | gaa | gtg | ccg | aac | ggc | ccg | tgg | 96 |
|---|---|---|---|---|---|---|---|---|---|---|---|---|---|---|---|---|
| Leu | Ser | Trp | Gln | Ser | Gly | Trp | Leu | Leu | Glu | Val | Pro | Asn | Gly | Pro | Trp | |
| | | | 20 | | | | | 25 | | | | | 30 | | | |

| cgc | agc | ctg | acc | ttt | tat | ccg | gcg | tgg | ctg | acc | gtg | agc | gaa | ggc | gcg | 144 |
|---|---|---|---|---|---|---|---|---|---|---|---|---|---|---|---|---|
| Arg | Ser | Leu | Thr | Phe | Tyr | Pro | Ala | Trp | Leu | Thr | Val | Ser | Glu | Gly | Ala | |
| | | 35 | | | | | 40 | | | | | 45 | | | | |

| aac | gcg | acc | ttt | acc | tgc | agc | ctg | agc | aac | tgg | agc | gaa | gat | ctg | atg | 192 |
|---|---|---|---|---|---|---|---|---|---|---|---|---|---|---|---|---|
| Asn | Ala | Thr | Phe | Thr | Cys | Ser | Leu | Ser | Asn | Trp | Ser | Glu | Asp | Leu | Met | |
| | 50 | | | | | 55 | | | | | 60 | | | | | |

| ctg | aac | tgg | aac | cgc | ctg | agc | ccg | agc | aac | cag | acc | gaa | aaa | cag | gcg | 240 |
|---|---|---|---|---|---|---|---|---|---|---|---|---|---|---|---|---|
| Leu | Asn | Trp | Asn | Arg | Leu | Ser | Pro | Ser | Asn | Gln | Thr | Glu | Lys | Gln | Ala | |
| 65 | | | | 70 | | | | | 75 | | | | | 80 | | |

| gcg | ttt | tgc | aac | ggc | ctg | agc | cag | ccg | gtg | cag | gat | gcg | cgc | ttt | cag | 288 |
|---|---|---|---|---|---|---|---|---|---|---|---|---|---|---|---|---|
| Ala | Phe | Cys | Asn | Gly | Leu | Ser | Gln | Pro | Val | Gln | Asp | Ala | Arg | Phe | Gln | |
| | | | | 85 | | | | | 90 | | | | | 95 | | |

| att | att | cag | ctg | ccg | aac | cgc | cat | gat | ttt | cat | atg | aac | att | ctg | gat | 336 |
|---|---|---|---|---|---|---|---|---|---|---|---|---|---|---|---|---|
| Ile | Ile | Gln | Leu | Pro | Asn | Arg | His | Asp | Phe | His | Met | Asn | Ile | Leu | Asp | |
| | | | 100 | | | | | 105 | | | | | 110 | | | |

| acc | cgc | cgc | aac | gat | agc | ggc | att | tat | ctg | tgc | ggc | gcg | att | agc | ctg | 384 |
|---|---|---|---|---|---|---|---|---|---|---|---|---|---|---|---|---|
| Thr | Arg | Arg | Asn | Asp | Ser | Gly | Ile | Tyr | Leu | Cys | Gly | Ala | Ile | Ser | Leu | |
| | | 115 | | | | | 120 | | | | | 125 | | | | |

| cat | ccg | aaa | gcg | aaa | att | gaa | gaa | agc | ccg | ggc | gcg | gaa | ctg | gtg | gtg | 432 |
|---|---|---|---|---|---|---|---|---|---|---|---|---|---|---|---|---|
| His | Pro | Lys | Ala | Lys | Ile | Glu | Glu | Ser | Pro | Gly | Ala | Glu | Leu | Val | Val | |
| | 130 | | | | | 135 | | | | | 140 | | | | | |

| acc | gaa | cgc | att | ctg | gaa | acc | agc | acc | cgc | tat | ccg | agc | ccg | agc | ccg | 480 |
|---|---|---|---|---|---|---|---|---|---|---|---|---|---|---|---|---|
| Thr | Glu | Arg | Ile | Leu | Glu | Thr | Ser | Thr | Arg | Tyr | Pro | Ser | Pro | Ser | Pro | |
| 145 | | | | 150 | | | | | 155 | | | | | 160 | | |

| aaa | ccg | gaa | ggc | cgc | ttt | cag | ggc | atg | gtg | att | ggc | att | atg | agc | gcg | 528 |
|---|---|---|---|---|---|---|---|---|---|---|---|---|---|---|---|---|
| Lys | Pro | Glu | Gly | Arg | Phe | Gln | Gly | Met | Val | Ile | Gly | Ile | Met | Ser | Ala | |
| | | | | 165 | | | | | 170 | | | | | 175 | | |

| ctg | gtg | ggc | att | ccg | gtg | ctg | ctg | ctg | gcg | tgg | gcg | ctg | aac | agc | 576 |
|---|---|---|---|---|---|---|---|---|---|---|---|---|---|---|---|
| Leu | Val | Gly | Ile | Pro | Val | Leu | Leu | Leu | Ala | Trp | Ala | Leu | Asn | Ser | |
| | | | 180 | | | | | 185 | | | | | 190 | | |

| cgc | cgc | aac | cgc | ctg | ctg | cag | agc | gat | ttt | atg | aac | atg | acc | ccg | cgc | 624 |
|---|---|---|---|---|---|---|---|---|---|---|---|---|---|---|---|---|
| Arg | Arg | Asn | Arg | Leu | Leu | Gln | Ser | Asp | Phe | Met | Asn | Met | Thr | Pro | Arg | |
| | | 195 | | | | | 200 | | | | | 205 | | | | |

| cgc | ccg | ggc | ctg | acc | cgc | aaa | ccg | tat | cag | ccg | tat | gcg | ccg | gcg | cgc | 672 |
|---|---|---|---|---|---|---|---|---|---|---|---|---|---|---|---|---|
| Arg | Pro | Gly | Leu | Thr | Arg | Lys | Pro | Tyr | Gln | Pro | Tyr | Ala | Pro | Ala | Arg | |
| | 210 | | | | | 215 | | | | | 220 | | | | | |

| gat | ttt | gcg | gcg | tat | cgc | ccg | | | | | | | | | | 693 |
|---|---|---|---|---|---|---|---|---|---|---|---|---|---|---|---|---|
| Asp | Phe | Ala | Ala | Tyr | Arg | Pro | | | | | | | | | | |

<210> SEQ ID NO 52
<211> LENGTH: 231
<212> TYPE: PRT
<213> ORGANISM: Artificial Sequence
<220> FEATURE:
<223> OTHER INFORMATION: [CDS]:1..693 from SEQ ID NO 51

<400> SEQUENCE: 52

```
Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
                165                 170                 175

Leu Val Gly Ile Pro Val Leu Leu Leu Leu Ala Trp Ala Leu Asn Ser
            180                 185                 190

Arg Arg Asn Arg Leu Leu Gln Ser Asp Phe Met Asn Met Thr Pro Arg
        195                 200                 205

Arg Pro Gly Leu Thr Arg Lys Pro Tyr Gln Pro Tyr Ala Pro Ala Arg
    210                 215                 220

Asp Phe Ala Ala Tyr Arg Pro
225                 230
```

<210> SEQ ID NO 53
<211> LENGTH: 693
<212> TYPE: DNA
<213> ORGANISM: Artificial Sequence
<220> FEATURE:
<221> NAME/KEY: source
<222> LOCATION: 1..693
<223> OTHER INFORMATION: /mol_type="unassigned DNA"
    /note="PTM-AYAA construct (murine)"
    /organism="Artificial Sequence"
<220> FEATURE:
<221> NAME/KEY: CDS
<222> LOCATION: 1..693
<223> OTHER INFORMATION: /transl_table=1

<400> SEQUENCE: 53

```
atg tgg gtg cgc cag gtg ccg tgg agc ttt acc tgg gcg gtg ctg cag    48
Met Trp Val Arg Gln Val Pro Trp Ser Phe Thr Trp Ala Val Leu Gln
1               5                   10                  15
```

| | |
|---|---|
| ctg agc tgg cag agc ggc tgg ctg ctg gaa gtg ccg aac ggc ccg tgg<br>Leu Ser Trp Gln Ser Gly Trp Leu Leu Glu Val Pro Asn Gly Pro Trp<br>　　　　　20　　　　　　　　25　　　　　　　　30 | 96 |
| cgc agc ctg acc ttt tat ccg gcg tgg ctg acc gtg agc gaa ggc gcg<br>Arg Ser Leu Thr Phe Tyr Pro Ala Trp Leu Thr Val Ser Glu Gly Ala<br>　　　35　　　　　　　　40　　　　　　　　45 | 144 |
| aac gcg acc ttt acc tgc agc ctg agc aac tgg agc gaa gat ctg atg<br>Asn Ala Thr Phe Thr Cys Ser Leu Ser Asn Trp Ser Glu Asp Leu Met<br>50　　　　　　　　55　　　　　　　　60 | 192 |
| ctg aac tgg aac cgc ctg agc ccg agc aac cag acc gaa aaa cag gcg<br>Leu Asn Trp Asn Arg Leu Ser Pro Ser Asn Gln Thr Glu Lys Gln Ala<br>65　　　　　　　　70　　　　　　　　75　　　　　　　　80 | 240 |
| gcg ttt tgc aac ggc ctg agc cag ccg gtg cag gat gcg cgc ttt cag<br>Ala Phe Cys Asn Gly Leu Ser Gln Pro Val Gln Asp Ala Arg Phe Gln<br>　　　　　85　　　　　　　　90　　　　　　　　95 | 288 |
| att att cag ctg ccg aac cgc cat gat ttt cat atg aac att ctg gat<br>Ile Ile Gln Leu Pro Asn Arg His Asp Phe His Met Asn Ile Leu Asp<br>　　　100　　　　　　　　105　　　　　　　　110 | 336 |
| acc cgc cgc aac gat agc ggc att tat ctg tgc ggc gcg att agc ctg<br>Thr Arg Arg Asn Asp Ser Gly Ile Tyr Leu Cys Gly Ala Ile Ser Leu<br>115　　　　　　　　120　　　　　　　　125 | 384 |
| cat ccg aaa gcg aaa att gaa gaa agc ccg ggc gcg gaa ctg gtg gtg<br>His Pro Lys Ala Lys Ile Glu Glu Ser Pro Gly Ala Glu Leu Val Val<br>130　　　　　　　　135　　　　　　　　140 | 432 |
| acc gaa cgc att ctg gaa acc agc acc cgc tat ccg agc ccg agc ccg<br>Thr Glu Arg Ile Leu Glu Thr Ser Thr Arg Tyr Pro Ser Pro Ser Pro<br>145　　　　　　　　150　　　　　　　　155　　　　　　　　160 | 480 |
| aaa ccg gaa ggc cgc ttt cag ggc atg gtg att ggc att atg agc gcg<br>Lys Pro Glu Gly Arg Phe Gln Gly Met Val Ile Gly Ile Met Ser Ala<br>　　　165　　　　　　　　170　　　　　　　　175 | 528 |
| ctg gtg ggc att ccg gtg ctg ctg ctg gcg tgg gcg ctg aac agc<br>Leu Val Gly Ile Pro Val Leu Leu Leu Ala Trp Ala Leu Asn Ser<br>　　　　　180　　　　　　　　185　　　　　　　　190 | 576 |
| cgc cgc aac cgc ctg ctg cag agc gat tat atg aac atg acc ccg cgc<br>Arg Arg Asn Arg Leu Leu Gln Ser Asp Tyr Met Asn Met Thr Pro Arg<br>　　　195　　　　　　　　200　　　　　　　　205 | 624 |
| cgc ccg ggc ctg acc cgc aaa ccg tat cag gcg tat gcg gcg gcg cgc<br>Arg Pro Gly Leu Thr Arg Lys Pro Tyr Gln Ala Tyr Ala Ala Ala Arg<br>210　　　　　　　　215　　　　　　　　220 | 672 |
| gat ttt gcg gcg tat cgc ccg<br>Asp Phe Ala Ala Tyr Arg Pro<br>225　　　　　　　　230 | 693 |

<210> SEQ ID NO 54
<211> LENGTH: 231
<212> TYPE: PRT
<213> ORGANISM: Artificial Sequence
<220> FEATURE:
<223> OTHER INFORMATION: [CDS]:1..693 from SEQ ID NO 53

<400> SEQUENCE: 54

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala

```
                     65                  70                  75                  80
Ala Phe Cys Asn Gly Leu Ser Gln Pro Val Gln Asp Ala Arg Phe Gln
                 85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
                165                 170                 175

Leu Val Gly Ile Pro Val Leu Leu Leu Leu Ala Trp Ala Leu Asn Ser
            180                 185                 190

Arg Arg Asn Arg Leu Leu Gln Ser Asp Tyr Met Asn Met Thr Pro Arg
        195                 200                 205

Arg Pro Gly Leu Thr Arg Lys Pro Tyr Gln Ala Tyr Ala Ala Ala Arg
    210                 215                 220

Asp Phe Ala Ala Tyr Arg Pro
225                 230

<210> SEQ ID NO 55
<211> LENGTH: 693
<212> TYPE: DNA
<213> ORGANISM: Artificial Sequence
<220> FEATURE:
<221> NAME/KEY: source
<222> LOCATION: 1..693
<223> OTHER INFORMATION: /mol_type="unassigned DNA"
      /note="PTM-FMNM-AYAA construct (murine)"
      /organism="Artificial Sequence"
<220> FEATURE:
<221> NAME/KEY: CDS
<222> LOCATION: 1..693
<223> OTHER INFORMATION: /transl_table=1

<400> SEQUENCE: 55 atg tgg gtg cgc cag gtg ccg tgg agc ttt acc tgg gcg gtg ctg cag        48
Met Trp Val Arg Gln Val Pro Trp Ser Phe Thr Trp Ala Val Leu Gln
1               5                   10                  15 ctg agc tgg cag agc ggc tgg ctg ctg gaa gtg ccg aac ggc ccg tgg        96
Leu Ser Trp Gln Ser Gly Trp Leu Leu Glu Val Pro Asn Gly Pro Trp
            20                  25                  30 cgc agc ctg acc ttt tat ccg gcg tgg ctg acc gtg agc gaa ggc gcg       144
Arg Ser Leu Thr Phe Tyr Pro Ala Trp Leu Thr Val Ser Glu Gly Ala
        35                  40                  45 aac gcg acc ttt acc tgc agc ctg agc aac tgg agc gaa gat ctg atg       192
Asn Ala Thr Phe Thr Cys Ser Leu Ser Asn Trp Ser Glu Asp Leu Met
    50                  55                  60 ctg aac tgg aac cgc ctg agc ccg agc aac cag acc gaa aaa cag gcg       240
Leu Asn Trp Asn Arg Leu Ser Pro Ser Asn Gln Thr Glu Lys Gln Ala
65                  70                  75                  80 gcg ttt tgc aac ggc ctg agc cag ccg gtg cag gat gcg cgc ttt cag       288
Ala Phe Cys Asn Gly Leu Ser Gln Pro Val Gln Asp Ala Arg Phe Gln
                85                  90                  95 att att cag ctg ccg aac cgc cat gat ttt cat atg aac att ctg gat       336
Ile Ile Gln Leu Pro Asn Arg His Asp Phe His Met Asn Ile Leu Asp
            100                 105                 110 acc cgc cgc aac gat agc ggc att tat ctg tgc ggc gcg att agc ctg       384
Thr Arg Arg Asn Asp Ser Gly Ile Tyr Leu Cys Gly Ala Ile Ser Leu
```

```
Thr Arg Arg Asn Asp Ser Gly Ile Tyr Leu Cys Gly Ala Ile Ser Leu
        115                 120                 125 cat ccg aaa gcg aaa att gaa gaa agc ccg ggc gcg gaa ctg gtg gtg    432
His Pro Lys Ala Lys Ile Glu Glu Ser Pro Gly Ala Glu Leu Val Val
    130                 135                 140 acc gaa cgc att ctg gaa acc agc acc cgc tat ccg agc ccg agc ccg    480
Thr Glu Arg Ile Leu Glu Thr Ser Thr Arg Tyr Pro Ser Pro Ser Pro
145                 150                 155                 160 aaa ccg gaa ggc cgc ttt cag ggc atg gtg att ggc att atg agc gcg    528
Lys Pro Glu Gly Arg Phe Gln Gly Met Val Ile Gly Ile Met Ser Ala
                165                 170                 175 ctg gtg ggc att ccg gtg ctg ctg ctg gcg tgg gcg ctg aac agc        576
Leu Val Gly Ile Pro Val Leu Leu Leu Ala Trp Ala Leu Asn Ser
            180                 185                 190 cgc cgc aac cgc ctg ctg cag agc gat ttt atg aac atg acc ccg cgc    624
Arg Arg Asn Arg Leu Leu Gln Ser Asp Phe Met Asn Met Thr Pro Arg
        195                 200                 205 cgc ccg ggc ctg acc cgc aaa ccg tat cag gcg tat gcg gcg gcg cgc    672
Arg Pro Gly Leu Thr Arg Lys Pro Tyr Gln Ala Tyr Ala Ala Ala Arg
    210                 215                 220 gat ttt gcg gcg tat cgc ccg                                        693
Asp Phe Ala Ala Tyr Arg Pro
225                 230

<210> SEQ ID NO 56
<211> LENGTH: 231
<212> TYPE: PRT
<213> ORGANISM: Artificial Sequence
<220> FEATURE:
<223> OTHER INFORMATION: [CDS]:1..693 from SEQ ID NO 55

<400> SEQUENCE: 56

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
                165                 170                 175

Leu Val Gly Ile Pro Val Leu Leu Leu Ala Trp Ala Leu Asn Ser
            180                 185                 190

Arg Arg Asn Arg Leu Leu Gln Ser Asp Phe Met Asn Met Thr Pro Arg
        195                 200                 205
```

Arg Pro Gly Leu Thr Arg Lys Pro Tyr Gln Ala Tyr Ala Ala Arg
    210                 215                 220

Asp Phe Ala Ala Tyr Arg Pro
225                 230

<210> SEQ ID NO 57
<211> LENGTH: 741
<212> TYPE: DNA
<213> ORGANISM: Artificial Sequence
<220> FEATURE:
<221> NAME/KEY: source
<222> LOCATION: 1..741
<223> OTHER INFORMATION: /mol_type="unassigned DNA"
     /note="murine PD1 deletion mutant"
     /organism="Artificial Sequence"
<220> FEATURE:
<221> NAME/KEY: CDS
<222> LOCATION: 1..741
<223> OTHER INFORMATION: /transl_table=1

<400> SEQUENCE: 57

| | | | | | | | | | | | | | | | |
|---|---|---|---|---|---|---|---|---|---|---|---|---|---|---|---|
| atg | tgg | gtg | cgc | cag | gtg | ccg | tgg | agc | ttt | acc | tgg | gcg | gtg | ctg | cag | 48 |
| Met | Trp | Val | Arg | Gln | Val | Pro | Trp | Ser | Phe | Thr | Trp | Ala | Val | Leu | Gln | |
| 1 | | | | 5 | | | | | 10 | | | | | 15 | | |

| ctg | agc | tgg | cag | agc | ggc | tgg | ctg | ctg | gaa | gtg | ccg | aac | ggc | ccg | tgg | 96 |
| Leu | Ser | Trp | Gln | Ser | Gly | Trp | Leu | Leu | Glu | Val | Pro | Asn | Gly | Pro | Trp | |
| | | | 20 | | | | | 25 | | | | | 30 | | | |

| cgc | agc | ctg | acc | ttt | tat | ccg | gcg | tgg | ctg | acc | gtg | agc | gaa | ggc | gcg | 144 |
| Arg | Ser | Leu | Thr | Phe | Tyr | Pro | Ala | Trp | Leu | Thr | Val | Ser | Glu | Gly | Ala | |
| | | | 35 | | | | 40 | | | | | 45 | | | | |

| aac | gcg | acc | ttt | acc | tgc | agc | ctg | agc | aac | tgg | agc | gaa | gat | ctg | atg | 192 |
| Asn | Ala | Thr | Phe | Thr | Cys | Ser | Leu | Ser | Asn | Trp | Ser | Glu | Asp | Leu | Met | |
| | 50 | | | | | 55 | | | | | 60 | | | | | |

| ctg | aac | tgg | aac | cgc | ctg | agc | ccg | agc | aac | cag | acc | gaa | aaa | cag | gcg | 240 |
| Leu | Asn | Trp | Asn | Arg | Leu | Ser | Pro | Ser | Asn | Gln | Thr | Glu | Lys | Gln | Ala | |
| 65 | | | | | 70 | | | | | 75 | | | | | 80 | |

| gcg | ttt | tgc | aac | ggc | ctg | agc | cag | ccg | gtg | cag | gat | gcg | cgc | ttt | cag | 288 |
| Ala | Phe | Cys | Asn | Gly | Leu | Ser | Gln | Pro | Val | Gln | Asp | Ala | Arg | Phe | Gln | |
| | | | | 85 | | | | | 90 | | | | | 95 | | |

| att | att | cag | ctg | ccg | aac | cgc | cat | gat | ttt | cat | atg | aac | att | ctg | gat | 336 |
| Ile | Ile | Gln | Leu | Pro | Asn | Arg | His | Asp | Phe | His | Met | Asn | Ile | Leu | Asp | |
| | | | | 100 | | | | | 105 | | | | | 110 | | |

| acc | cgc | cgc | aac | gat | agc | ggc | att | tat | ctg | tgc | ggc | gcg | att | agc | ctg | 384 |
| Thr | Arg | Arg | Asn | Asp | Ser | Gly | Ile | Tyr | Leu | Cys | Gly | Ala | Ile | Ser | Leu | |
| | | | 115 | | | | | 120 | | | | | 125 | | | |

| cat | ccg | aaa | gcg | aaa | att | gaa | gaa | agc | ccg | ggc | gcg | gaa | ctg | gtg | gtg | 432 |
| His | Pro | Lys | Ala | Lys | Ile | Glu | Glu | Ser | Pro | Gly | Ala | Glu | Leu | Val | Val | |
| | 130 | | | | | 135 | | | | | 140 | | | | | |

| acc | gaa | cgc | att | ctg | gaa | acc | agc | acc | cgc | tat | ccg | agc | ccg | agc | ccg | 480 |
| Thr | Glu | Arg | Ile | Leu | Glu | Thr | Ser | Thr | Arg | Tyr | Pro | Ser | Pro | Ser | Pro | |
| 145 | | | | | 150 | | | | | 155 | | | | | 160 | |

| aaa | ccg | gaa | ggc | cgc | ttt | cag | ggc | atg | gtg | att | ggc | att | atg | agc | gcg | 528 |
| Lys | Pro | Glu | Gly | Arg | Phe | Gln | Gly | Met | Val | Ile | Gly | Ile | Met | Ser | Ala | |
| | | | | 165 | | | | | 170 | | | | | 175 | | |

| ctg | gtg | ggc | att | ccg | gtg | ctg | ctg | ctg | gcg | tgg | gcg | ctg | gcg | gtg | | 576 |
| Leu | Val | Gly | Ile | Pro | Val | Leu | Leu | Leu | Ala | Trp | Ala | Leu | Ala | Val | | |
| | | | 180 | | | | | 185 | | | | | 190 | | | |

| ttt | tgc | agc | acc | agc | atg | agc | gaa | gcg | cgc | ggc | gcg | ggc | agc | aaa | gat | 624 |
| Phe | Cys | Ser | Thr | Ser | Met | Ser | Glu | Ala | Arg | Gly | Ala | Gly | Ser | Lys | Asp | |
| | | | 195 | | | | | 200 | | | | | 205 | | | |

| gat | acc | ctg | aaa | gaa | gaa | ccg | agc | gcg | gcg | ccg | gtg | ccg | agc | gtg | gcg | 672 |
| Asp | Thr | Leu | Lys | Glu | Glu | Pro | Ser | Ala | Ala | Pro | Val | Pro | Ser | Val | Ala | |

```
                    210                 215                 220
tat gaa gaa ctg gat ttt cag ggc cgc gaa aaa acc ccg gaa ctg ccg        720
Tyr Glu Glu Leu Asp Phe Gln Gly Arg Glu Lys Thr Pro Glu Leu Pro
225                 230                 235                 240 acc gcg tgc gtg cat acc gaa                                            741
Thr Ala Cys Val His Thr Glu
                245

<210> SEQ ID NO 58
<211> LENGTH: 247
<212> TYPE: PRT
<213> ORGANISM: Artificial Sequence
<220> FEATURE:
<223> OTHER INFORMATION: [CDS]:1..741 from SEQ ID NO 57

<400> SEQUENCE: 58

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
                165                 170                 175

Leu Val Gly Ile Pro Val Leu Leu Leu Leu Ala Trp Ala Leu Ala Val
            180                 185                 190

Phe Cys Ser Thr Ser Met Ser Glu Ala Arg Gly Ala Gly Ser Lys Asp
        195                 200                 205

Asp Thr Leu Lys Glu Glu Pro Ser Ala Ala Pro Val Pro Ser Val Ala
    210                 215                 220

Tyr Glu Glu Leu Asp Phe Gln Gly Arg Glu Lys Thr Pro Glu Leu Pro
225                 230                 235                 240

Thr Ala Cys Val His Thr Glu
                245

<210> SEQ ID NO 59
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
      /note="Primer"
      /organism="Artificial Sequence"
```

```
<400> SEQUENCE: 59
atagcggccg cgccaccatg tgggtccgg                                    29

<210> SEQ ID NO 60
<211> LENGTH: 23
<212> TYPE: DNA
<213> ORGANISM: Artificial Sequence
<220> FEATURE:
<221> NAME/KEY: source
<222> LOCATION: 1..23
<223> OTHER INFORMATION: /mol_type="unassigned DNA"
      /note="Primer"
      /organism="Artificial Sequence"

<400> SEQUENCE: 60
ccttctacta ttgcagaaga cag                                          23

<210> SEQ ID NO 61
<211> LENGTH: 23
<212> TYPE: DNA
<213> ORGANISM: Artificial Sequence
<220> FEATURE:
<221> NAME/KEY: source
<222> LOCATION: 1..23
<223> OTHER INFORMATION: /mol_type="unassigned DNA"
      /note="Primer"
      /organism="Artificial Sequence"

<400> SEQUENCE: 61
ctgtcttctg caatagtaga agg                                          23

<210> SEQ ID NO 62
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="unassigned DNA"
      /note="Primer"
      /organism="Artificial Sequence"

<400> SEQUENCE: 62
tatgaattct cagggcggt acgctgca                                      28

<210> SEQ ID NO 63
<211> LENGTH: 29
<212> TYPE: DNA
<213> ORGANISM: Artificial Sequence
<220> FEATURE:
<221> NAME/KEY: source
<222> LOCATION: 1..29
<223> OTHER INFORMATION: /mol_type="unassigned DNA"
      /note="Primer"
      /organism="Artificial Sequence"

<400> SEQUENCE: 63
atagcggccg cgccaccatg tgggtccgg                                    29

<210> SEQ ID NO 64
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="unassigned DNA"
      /note="Primer"
```

```
    /organism="Artificial Sequence"

<400> SEQUENCE: 64
tatgaattct cagggcggt acgctgca                                              28

<210> SEQ ID NO 65
<211> LENGTH: 8
<212> TYPE: PRT
<213> ORGANISM: Artificial Sequence
<220> FEATURE:
<223> OTHER INFORMATION: Control peptide

<400> SEQUENCE: 65

Ser Ile Ile Asn Phe Glu Lys Leu
1               5
```

PD-1-CD28 FUSION PROTEINS AND THEIR USE IN MEDICINE

The present application is a National Phase application of International Application No. PCT/EP2016/064195, filed Jun. 20, 2016, which claims priority to European Application No. 15172913,4 filed Jun. 19, 2015. The entirety of each application is incorporated by reference herein. The International Application was published in English on Dec. 22, 2016 as Publication No. WO 2016/203048 A1, the entire contents of which are hereby incorporated by reference herein.

The present invention relates to PD-1-CD28 fusion proteins, nucleic acid molecules, vectors, transduced cells carrying nucleic acid molecules or vectors of the present invention or expressing the fusion proteins of the present invention, methods and kits comprising the nucleic acid molecules, vectors and/or the fusion proteins of the present invention. The invention also provides the use of said transduced cells in a method for the treatment of particular diseases as well as a pharmaceutical composition/medicament comprising said transduced cells expressing the fusion proteins of the present invention for use in a method of treating of diseases, in particular in the medical intervention of diseases characterized by PD-L1 and/or PD-L2 expression.

Adoptive T cell therapy (ACT) is a powerful approach to treat even advanced stages of metastatic cancer (Rosenberg, Nat Rev Clin Oncol 8(10) (2011), 577-585). For ACT, antigen-specific T cells are isolated or engineered and are expanded in vitro prior to reinfusion to the patient (Gattinoni et al., Nat Rev Immunol 6(5) (2006), 383-393). In clinical trials, unparalleled response rates in some cancer patients have been achieved by ACT in conjunction with total body irradiation. However, the majority of patients do not respond to this treatment (Dudley et al., J Clin Oncol 26(32) (2008), 5233-5239; Rosenberg et al., Clin Cancer Res 17(13) (2011), 4550-4557). Tumor-induced immunosuppression which is not counteracted by total body irradiation has been implicated in this resistance to therapy (Leen et al., Annu Rev Immunol 25 (2007), 243-265). Recently, inhibitory receptors upregulated on activated T cells and their respective ligands expressed within the tumor milieu have shown to contribute to T cell therapy failure (Abate-Daga et al., Blood 122(8) (2013), 1399-410). Among the inhibitory receptors, the programmed death receptor-1 (PD-1) plays a central role, given that recent studies have identified PD-1 expressed on tumor-antigen-specific T cells in tumors (Gros et al., J Clin Invest (2014), 10.1172/JCI73639). The interaction of PD-1 with its ligand PD-L1 suppresses TCR signaling and T cell activation and thus prevents effective activation upon target recognition (Gros et al., J Clin Invest (2014), 10.1172/JCI73639; Yokosuka et al., J Exp Med 209(6) (2012), 1201-1217; Ding et al., Cancer Res (2014), 10.1158/0008-5472.CAN-13-3596; Karyampudi et al., Cancer Res (2014), 10.1158/0008-5472.CAN-13-2564). The clinical weight of these mechanisms is underlined by therapeutic studies combining ACT or gene-modified T cells with antibody-based PD-1 blockade that result in a marked improvement of anti-tumor activity (John et al., Clin Cancer Res 19(20) (2013), 5636-5646; Goding et al., J Immunol 190(9) (2013), 4899-4909). The systemic application of PD-1- or PD-L1-blocking antibodies has the disadvantage of potentially targeting T cells of any reactivity and thus of inducing systemic side effects (Topalian et al., N Engl J Med 366(26) (2012), 2443-2454; Brahmer et al., N Engl J Med 366(26) (2012), 2455-2465). Moreover, ACT by itself bears considerable risk of toxicity, as recently seen in phase I studies (Linette et al., Blood 122(6) (2013), 863-871; Morgan et al., J Immunother 36(2) (2013), 133-151). The combination with indiscriminate PD-1 blockade carries the risk of potentiating side effects of either therapy alone. A potential strategy to pursue PD-1-PD-L1 blockade without non-selective T cell activation is to limit its effect to the tumor reactive T cells. The principal compatibility of signaling between a CD28 extracellular and a PD-1 intracellular domain has been demonstrated (Riley and June, Blood (2005), 105(1), 13-21; Chemnitz et al., J Immunol 173(2) (2004), 945-954). Further the compatibility of CTLA-4, PD-1 and CD28 has been employed to boost the T cell response and to use stimulatory CTLA-4-CD28 fusion receptor and to inhibit off-target T cell reactivity using inhibitory receptors with the signaling domain of PD-1 and CTLA-4 (Morales-Kastresana et al., Clin Cancer Res 19(20) (2013), 5546-5548, Yin et al., J Leukoc Biol 73(1) (2003), 178-182). Further, PD-1-CD28 fusion constructs were described containing a truncated extracellular domain of PD-1 and the transmembrane and intracellular domain of CD28 (Ankri et al., J. Immunol 191(8) (2013), 4121-4129). Moreover a PD-1-CD28 fusion protein containing a truncated extracellular domain of PD-1 and the intracellular domain, the transmembrane domain plus part of the CD28 extracellular domain was described (Prosser et al., Mol. Immunol. 51(3-4) (2012), 263-272).

However, in view of the PD-L1 mediated T cell inhibition, there is still a need to provide improved means having the potential to improve safety and efficacy of ACT and overcome the above disadvantages.

This need is addressed by the present invention by providing the embodiments as defined in the claims.

The present invention relates to a fusion protein comprising a PD-1 polypeptide and an intracellular domain of a CD28 polypeptide, wherein the PD-1 polypeptide comprises the extracellular domain and the transmembrane domain of PD-1.

The herein described PD-1-CD28 fusion protein is characterized in that the PD-1 polypeptide which comprises the extracellular domain and the transmembrane domain of PD-1 is operably linked via its C-terminus to the N-terminus of an intracellular domain of a CD28 polypeptide.

Figure 8:
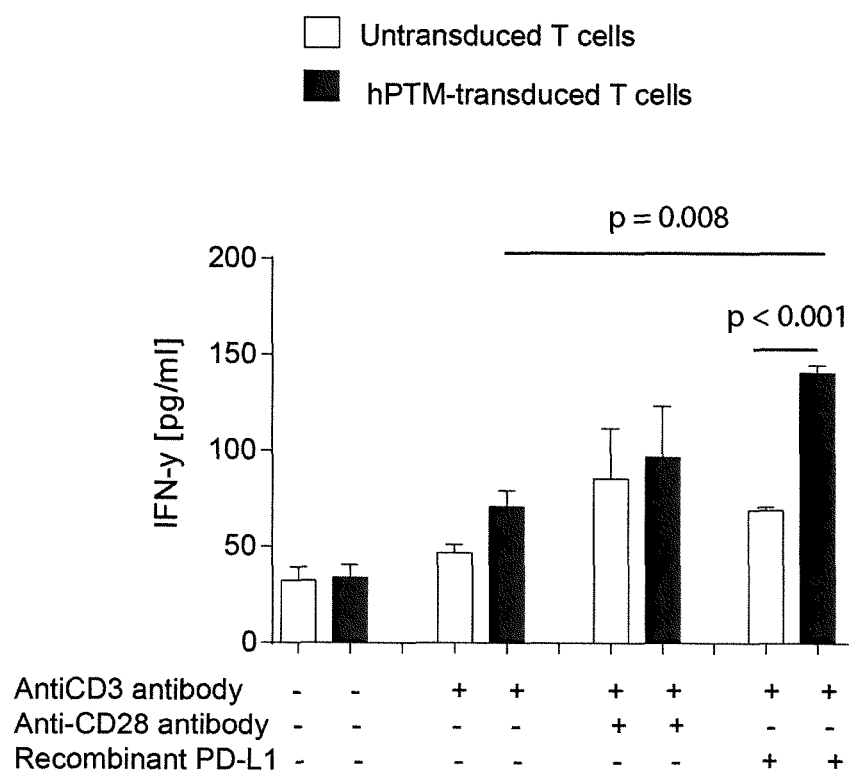

In contrast to the PD-1-CD28 fusion proteins described in Prosser et al., Mol. Immunol. 51(3-4) (2012), 263-272 and Ankri et al., J. Immunol 191(8) (2013), 4121-4129, the PD-1-CD28 fusion protein of the present invention comprises the transmembrane domain of the PD-1 polypeptide. As shown in the appended Examples the architecture of the PD-1-CD28 fusion proteins previously described showed only modest cytokine induction (2- to 3-fold) and little or no difference in lytic activity when transduced into primary T cells. This is in marked contrast to the fusion protein of the present invention, which achieved up to 300-fold increase in IL-2 and IFN-γ secretion and strong T cell proliferation as well as enhancement of tumor cell lytic activity in vitro and in vivo (cf. FIGS. 2, 3, 5 and 9). Accordingly, it was surprisingly found that the PD-1-CD28 fusion protein of the present invention carrying the PD-1 transmembrane domain (PTM) referring to PD-1-CD28 fusion proteins having an amino acid sequence as shown in SEQ ID NO: 14 (murine/mouse) or SEQ ID NO: 24 (human)) is superior to previously described PD-1-CD28 fusion constructs described in Prosser et al., Mol. Immunol. 51(3-4) (2012), 263-272 (referring to a PD-1-CD28 fusion protein with an architecture as the fusion protein named herein "CEX") and Ankri et al., J. Immunol 191(8) (2013), 4121-4129 (referring to a PD-1-CD28 fusion protein with an architecture as the fusion protein named herein "CTM"; cf. FIG. 2). More precisely, it is shown in the appended Examples that the fusing of the extracellular domain plus the transmembrane domain to the intracellular domain of CD28 protects the transduced cells from PD-1-L1-induced T cell inhibition and turns the inhibitory signal into a co-stimulation signal for optimal T cell function. As shown in FIG. 6E (as a proof of concept of the mechanism of action), it was surprisingly found that the fusion protein of the PD-1 extracellular and transmembrane domain with the CD28 intracellular domain protects the antigen-specific T cells from PD-1-PD-L1-mediated anergy and turns the inhibitory signal into a co-stimulation. In other words, cells, like T cells, transduced with the PD-1-CD28 fusion protein of the present invention are resistant to the PD-1-PD-L1-mediated anergy. Furthermore, the functionality of PD-1-CD28 fusion constructs based on the human PD-1 and CD28 sequences is shown in FIG. 8.

Accordingly, the present invention relates to a fusion protein comprising a PD-1 polypeptide that is operably linked via its C-terminus to the N-terminus of an intracellular domain of a CD28 polypeptide, wherein the polypeptide comprises the extracellular domain and the transmembrane domain of PD-1.

In the context of the present invention, the term "fusion protein" relates to a protein which is made of polypeptide parts from different sources. Accordingly, it may be also understood as a "chimeric protein". Usually, fusion proteins are proteins created through the joining of two or more genes (or preferably cDNAs) that originally coded for separate proteins. Translation of this fusion gene (or fusion cDNA) results in a single polypeptide, preferably with functional properties derived from each of the original proteins. Recombinant fusion proteins are created artificially by recombinant DNA technology for use in biological research or therapeutics. Further details to the production of the fusion protein of the present invention are described herein below.

In the context of the present invention, the terms "polypeptide", "peptide" and "protein" are used interchangeably to refer to a polymer of amino acid residues. The term also applies to amino acid polymers in which one or more amino acid residues is an artificial chemical mimetic or a corresponding naturally occurring amino acid, as well as to naturally occurring amino acid polymers. Accordingly, in the context of the present invention, the term "polypeptide" relates to a molecule which comprises or consists of chains of amino acid monomers linked by peptide (amide) bonds. Peptide bonds are covalent chemical bonds which are formed when the carboxyl group of one amino acid reacts with the amino group of another. Herein a "polypeptide" is not restricted to a molecule with a defined length. Thus, herein the term "polypeptide" relates to a peptide, an oligopeptide, a protein, or a polypeptide which encompasses amino acid chains, wherein the amino acid residues are linked by covalent peptide bonds. However, herein the term "polypeptide" also encompasses peptidomimetics of such proteins/polypeptides wherein amino acid(s) and/or peptide bond(s) have been replaced by functional analogs. The term polypeptide also refers to, and does not exclude, modifications of the polypeptide, e.g., glycosylation, acetylation, phosphorylation and the like. Such modifications are well described in the art.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g. hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid. Amino acids may be referred to herein by either their commonly known three letter symbols or by the one-letter symbols recommended by the IUPAC-IUB Biochemical Nomenclature Commission.

In the context of the present invention, the fusion protein may comprise a fragment/polypeptide part of the full length PD-1 polypeptide and a fragment/polypeptide part of the full length CD28 polypeptide. Thus, the "PD-1 polypeptide" which is comprised in the herein provided fusion protein is a fragment/polypeptide part of the full length PD-1 polypeptide. The amino acid sequences of murine/mouse and human full length PD-1 are shown herein as SEQ ID NOs: 2 (murine/mouse as encoded by the cDNA sequence shown in SEQ ID NO: 1) and 4 (human as encoded by the cDNA sequence shown in SEQ ID NO: 3), respectively (the Uni Prot Entry number of human full length PD-1 is Q15116 (accession number with the entry version number 138 and version 3 of the sequence); the Uni Prot Entry number of the murine/mouse full length PD-1 is Q02242 (accession number with the entry version number 125 and version 1 of the sequence). Analogously, the "CD28 polypeptide" which is comprised in the herein provided fusion protein is a fragment/polypeptide part of the full length CD28 polypeptide. The amino acid sequences of human and murine/mouse full length CD28 are shown herein as SEQ ID NOs: 26 (murine/mouse as encoded by the copy DNA (cDNA) sequence shown in SEQ ID NO: 25) and 28 (human as encoded by the cDNA sequence shown in SEQ ID NO: 27), respectively. As mentioned above, the herein provided fusion protein comprises a PD-1 polypeptide which is operably linked via its C-terminus to the N-terminus of an intracellular domain of a CD28 polypeptide, wherein the PD-1 polypeptide comprises the extracellular domain and the transmembrane domain of PD-1.

The herein provided fusion protein may comprise the amino acids 1 to 200, preferably the amino acids 1 to 190 of the amino acid sequence of PD-1 as shown in SEQ ID NO: 2 (murine/mouse full length PD-1 as encoded by the cDNA sequence shown in SEQ ID NO: 1). Further, in the context of the present invention, the herein provided PD-1-CD28 fusion protein may comprise the amino acids 1 to 180, 1 to 181, 1 to 182, 1 to 183, 1 to 184, 1 to 185, 1 to 186, 1 to 187, 1 to 188, 1 to 189, 1 to 190, 1 to 191, 1 to 192, 1 to 193, 1 to 194, 1 to 195, 1 to 196, 1 to 197, 1 to 198, 1 to 199, or 1 to 200 of the amino acid sequence of PD-1 as shown in SEQ ID NO: 2 (as encoded by the cDNA sequence shown in SEQ ID NO: 1). For example, the PD-1 polypeptide which is comprised in the fusion protein of the present invention may comprise or consist of the amino acid sequence as shown in SEQ ID NO: 8 (as encoded by the cDNA sequence shown in SEQ ID NO: 7) (murine/mouse). However, more preferably, the fusion protein of the present invention comprises polypeptides which are derived from a human origin. Thus, more preferably, the herein provided fusion protein comprises the amino acids 1 to 200, even more preferably the amino acids 1 to 191 of the amino acid sequence of PD-1 as shown in SEQ ID NO: 4 (human full length PD-1 as encoded by the cDNA shown in SEQ ID NO: 3). Accordingly, in the context of the present invention, the herein provided fusion protein preferably comprises the amino acids 1 to 180, 1 to 181, 1 to 182, 1 to 183, 1 to 184, 1 to 186, 1 to 187, 1 to 188, 1 to 189, 1 to 190, 1 to 191, 1 to 192, 1 to 193, 1 to 194, 1 to 195, 1 to 196, 1 to 197, 1 to 198, 1 to 199, or 1 to 200 of the amino acid sequence of PD-1 as shown in SEQ ID NO: 4 (human full length PD-1 as encoded by the cDNA shown in SEQ ID NO: 3). For example, the PD-1 polypeptide which is comprised in the fusion protein of the present invention may comprise or consist of the amino acid sequence as shown in SEQ ID NO: 16 (as encoded by the cDNA shown in SEQ ID NO: 15). Accordingly, in the context of the present invention the PD-1-CD28 fusion protein comprises the sequence as shown in SEQ ID NO: 16 or a sequence which has up to 1, 2, 3, 4, 5, 6, 7, 8, 9 or 10 substitutions, deletions or insertions in comparison to SEQ ID NO: 16 and which is characterized by having a PD-L1 or PD-L2 binding activity.

The above-mentioned substation, deletion, insertion/addition may be a conservative mutation. A "conservative mutation" refers to substitutions of amino acids in a protein with other amino acids having similar characteristics (e.g. charge, side-chain size, hydrophobicity/hydrophilicity, backbone conformation, rigidity, etc.) such that the changes can be frequently be made without altering the biological activity of the protein. Those of skill in the art recognize that, in general, single amino acid substitutions in non-essential regions of a polypeptide do not substantially alter biological activity (see, e.g., Watson Molecular Biology of the Gene, The Benjamin/Cummings Pub. Co., p. 224 (4th Ed.)) (1987). In addition, substitutions of structurally or functionally similar amino acids are less likely to disrupt biological activity. Various embodiments of the binding compounds of the present invention comprise polypeptide chains with sequences that include up to none, 1, 2, 3, 4, 5, 6, 7, 8, 9 or 10 conservative amino acid substitutions when compared with the specific amino acid sequences disclosed herein, e.g. SEQ ID NOs: 6, 8, 10, 16, 18 or 20.

Accordingly, in the context of the present invention, the PD-1 polypeptide which comprises the extracellular domain and the transmembrane domain of PD-1 (human full length PD-1 (SEQ ID NO: 4 (as encoded by the cDNA sequence shown in SEQ ID NO: 3)) may comprise a sequence having the amino acid sequence as shown in SEQ ID NO: 16, wherein the amino acid sequence has up to 1, 2, 3, 4, 5, 6, 7, 8, 9 or 10, preferably 1 to 8, more preferably 1 to 6, even more preferably 1 to 5, even more preferably 1 or 2, or even more preferably 1 substitution(s), deletion(s) or insertion(s) in comparison to amino acid sequence as shown in SEQ ID NO: 16. If in the herein provided fusion protein the PD-1 polypeptide comprises one or more substitution(s), deletion(s) or insertion(s) in comparison to the amino acid sequence of SEQ ID NO: 16, respectively, then said fusion protein is characterized by having a PD-L1 and/or PD-L2 binding activity. This binding activity is defined as the ability to bind the PD-L1 and/or PD-L2 ligand either with the same, enhanced or reduced affinity as compared to the natural full length PD-1 protein (e.g. a protein having the amino acid sequence as shown in SEQ ID NO: 4). The natural full length PD-1 protein binds to the PD-L1 ligand with an equilibrium dissociation constant (KD) of 770 nM or less (Butte et al., Molecular Immunology 45 (2008), 3567-3572) and the natural full length PD-1 proteins binds to the PD-L2 ligand with an equilibrium dissociation constant (KD) of 140 nM or less (Butte et al., Molecular Immunology 45 (2008), 3567-3572). Accordingly, in the context of the present invention, the PD-1 polypeptide which comprises the extracellular domain and the transmembrane domain of PD-1 (as e.g. shown in SEQ ID NO: 16 or a variant thereof having up to 1, 2, 3, 4, 5, 6, 7, 8, 9, or 10 substitution(s), deletion(s) or insertion(s) in comparison to amino acid sequence as shown in SEQ ID NO: 16) may bind to the PD-L1 and/or PD-L2 ligand with the same binding as the natural full length PD-1 protein does. Alternatively, in the context of the present invention, the PD-1 polypeptide which comprises the extracellular domain and the transmembrane domain of PD-1 (as e.g. shown in SEQ ID NO: 16 or a variant thereof having up to 1, 2, 3, 4, 5, 6, 7, 8, 9, or 10 substitution(s), deletion(s) or insertion(s) in comparison to amino acid sequence as shown in SEQ ID NO: 16) may bind to PD-L1 and/or PD-L2 ligand with a binding affinity that is at least 1000, 100, 50, 40, 30, 20, 10, 5-fold higher (i.e. enhanced) or lower (i.e. reduced) compared to the natural full length PD-1 protein. As used herein, the term "KD" is intended to refer to the dissociation constant and is expressed as a molar concentration (M). KD values for protein-protein interactions between e.g. the PD-1 polypeptide described herein above and PD-L1 and/or PD-L2 can be determined using methods well established in the art. Methods for determining the binding affinity towards PD-L1 and/PD-L2 ligand are known in the art and described herein below in more detail and include, e.g., surface plasmon resonance (SPR), biacore measurement, flow cytometry or ELISA.

In the context of the present invention, the PD-1-CD28 fusion protein comprises the extracellular domain of PD-1 which is located at amino acids 1 to 169 of the mouse full length PD-1 protein as shown in SEQ ID NO: 2 (as encoded by the cDNA shown in SEQ ID NO: 1). Alternatively, in the context of the present invention the fusion protein comprises the extracellular domain of PD-1 which is located at amino acids 1 to 170 of the human full length PD-1 protein as shown in SEQ ID NO: 4 (as encoded by the cDNA shown in SEQ ID NO: 3). In the context of the present invention the PD-1-CD28 fusion protein comprises or consists of the extracellular domain of PD-1 as shown in SEQ ID NO: 8 (as encoded by the cDNA sequence shown in SEQ ID NO: 7) or more preferably as shown in SEQ ID NO: 18 (as encoded by the cDNA sequence shown in SEQ ID NO: 17). The extracellular domain of the PD-1 protein (which is comprised in the herein provided fusion protein) is characterized by the ability to bind the natural ligands of PD-1 (i.e. (human) PD-L1 (Uni Prot Entry: Q9NZQ7 (accession number with the entry version: 130 and version 1 of the sequence) or (human) PD-L2 (Unit Prot Entry: Q9BQ51 (accession number with the entry version: 115 and version 2 of the sequence) with the same (i.e. equal), enhanced or reduced (i.e. diminished) affinity as compared to the natural PD-1 protein. The affinity of a fusion protein to PD-L1 and/or PD-L2 can be assayed as described herein below. The amino acid sequences of human full length PD-L1 and human full length PD-L2 are shown herein as SEQ ID NO: 34 (PD-L1 as encoded by the cDNA sequence shown in SEQ ID NO: 33) or SEQ ID NO: 36 (PD-L2 as encoded by the cDNA sequence shown in SEQ ID NO: 35). A reduced (i.e. diminished), same (i.e. equal) or preferably enhanced affinity to PD-L1 or PD-L2 can be achieved by point mutations in the extracellular domain of the herein provide fusion protein. For example, changing the alanine at the position corresponding to amino acid position 132 of SEQ ID NO: 18 by a leucine enhances PD-1 affinity (i.e. binding) to PD-L1 and PD-L2 By enhancing the affinity of the PD-1 polypeptide (which is comprised in the herein provided fusion protein) to PD-L1 and PD-L2, the activity of the herein provided fusion protein in cells is enhanced in terms of cytokine secretion, proliferation and lysis.

Binding affinity of the herein provided fusion protein to PD-L1 or PD-L2 can be assessed by methods well known by those skilled in the art including but not limited to flow cytometry, ELISA, immunoprecipitation, Western blot, confocal or conventional microscopy (Terawaki et al., International Immunology, 19(7) (2007), 881-890; Cheng et al., 3 Biol Chem. 288(17) (2013), 11771-11785; Ghiotto et al., Int Immunol. 22(8) (2010), 651-660.). In particular, binding of the said fusion protein to PD-L1 or PD-L2 leads to clustering of T cells around the target cell which could be a tumor or another immune cell and activation of those cells by means of the fusion protein. The fusion protein itself clusters to the contact point with the target cell. This can be measured and/or visualized, e.g., by confocal or conventional microscopy. Binding of the fusion protein (i.e. of the PD-1 polypeptide which is comprised in the fusion protein) to either PD-L1 or PD-L2 is central for any subsequent signaling via the CD28 signaling motifs of the fusion protein and the effects resulting thereof. Mutations in the fusion protein resulting in enhanced affinity for the ligands PD-L1 and/or PD-L2 can enhance the functionality of the fusion protein. Methods for measuring affinity of one protein to another are well known to those skilled in the art and include surface plasmon resonance (SPR), biacore measurement, flow cytometry or ELISA.

As described above, the herein provided PD-1-CD28 fusion protein comprises the transmembrane domain of PD-1 which is located at amino acids 170 to 191 of the mouse full length PD-1 protein as shown in SEQ ID NO: 2 (as encoded by the cDNA shown in SEQ ID NO: 1). The transmembrane domain of PD-1 is located at amino acids 171 to 191 of the human full length PD-1 protein (as shown in SEQ ID NO: 4 (as encoded by the cDNA shown in SEQ ID NO: 3)). The transmembrane domain of PD-1 is an important component of the fusion protein of the present invention and allows for signal transduction to the intracellular domains of CD28 upon engagement of the PD-1-receptor (i.e. the PD-1 polypeptide of the fusion protein). In the context of the present invention the transmembrane domain which is comprised in PD-1-CD28 fusion proteins may comprise or consist of the amino acid sequence as shown in SEQ ID NO: 10 (murine/mouse as encoded by cDNA sequence shown in SEQ ID NO: 9) or SEQ ID NO: 20 (human as encoded by the cDNA sequence shown in SEQ ID NO: 19). However, the transmembrane domain which is comprised in fusion protein of the present invention (SEQ ID NO: 10 or SEQ ID NO: 20) may comprise or consist of an amino acid sequence which includes up to 1, 2, 3, 4, 5, 6, 7, 8, 9 or 10, preferably, 1 to 8, more preferably 1 to 6, even more preferably 1 to 4, even more preferably 1 to 2, or even more preferably 1 substitution(s), deletion(s) or insertion(s) in comparison to amino acid sequence as shown in SEQ ID NO: 10 (murine/mouse) or 20 (human). If in the herein provided fusion protein the transmembrane domain comprises none, 1, 2, 3, 4, 5, 6, 7, 8, 9 or 10 substitution(s), deletion(s) or insertion(s) in comparison to the amino acid sequence as shown in SEQ ID NO: 10 (murine/mouse) or 20 (human), then said fusion protein is characterized by showing the same or preferably an enhanced signal transduction activity. Signal transduction activity can be measured by flow cytometry, Western blot or ELISA based assays detecting phosphorylated proteins such as V-akt murine thymoma oncogene homologue 1 (AKT). Signal transduction activity can also be detected by downstream functional effects such as cytokine release, proliferation or lytic activity of cells, such as T cells (as described e.g. herein in the appended Examples and in Krutzik et al., Methods Mol Biol. 699 (2011), 179-202; Ekkens et al., Infect Immun. 75(5) (2007), 2291-2296; Ge et al., Proc Natl Acad Sci USA. 99(5) (2002), 2983-2988; Düwell et al., Cell Death Differ. 21(12) (2014), 1825-1837, Erratum in: Cell Death Differ. 21(12) (2014), 161). Accordingly, the transmembrane domain of PD-1 is an important component of the PD-1-CD28 fusion protein of the present invention and provides signal transduction to the intracellular domains of CD28 upon engagement of the PD-1-receptor domain (i.e. the PD-1 polypeptide of the fusion protein) which can be measured by, e.g, the cytokine production, proliferation or lytic activity of cells such as T cells. Accordingly, in the context of the present invention the transmembrane of PD-1 has the amino acid sequence shown in SEQ ID NO: 20 (as encoded by the cDNA shown in SEQ ID NO: 19).

The intracellular domain of the PD-1-CD28 fusion protein of the present invention is derived from the (human) CD28 gene (Uni Prot Entry No: P10747 (accession number with the entry version: 164 and version 1 of the sequence) and provides CD28 activity, defined as cytokine production, proliferation and lytic activity of the transduced cell described herein, like a transduced T cell. CD28 activity can be measured by release of cytokines by ELISA or flow cytometry of cytokines such as interferon-gamma (IFN-γ) or interleukin 2 (IL-2) (as described herein below in the appended Examples), proliferation of T cells measured e.g. by ki67-measurement, cell quantification by flow cytometry (as described below in the appended Examples), or lytic activity as assessed by real time impedance measurement of the target cell (by using e.g. an ICELLligence instrument as described below in the appended Examples in section 3.1 and e.g. in Thakur et al., Biosens Bioelectron. 35(1) (2012), 503-506; Krutzik et al., Methods Mol Biol. 699 (2011), 179-202; Ekkens et al., Infect Immun. 75(5) (2007), 2291-2296; Ge et al., Proc Natl Acad Sci USA. 99(5) (2002), 2983-2988; Diiwell et al., Cell Death Differ. 21(12) (2014), 1825-1837, Erratum in: Cell Death Differ. 21(12) (2014), 161). The signaling domains PYAP (AA 208 to 211 of SEQ ID NO: 28 (as encoded by cDNA sequence shown in SEQ ID NO: 27)) and YMNM (AA 191 to 194 of SEQ ID NO: 28) are beneficial for the function of the CD28 polypeptide and the functional effects enumerated above. The amino acid sequence of the YMNM domain is shown in SEQ ID NO: 29; the amino acid sequence of the PYAP domain is shown in SEQ ID NO: 30. Accordingly, in the fusion protein of the present invention, the CD28 polypeptide preferably comprises a sequence derived from intracellular domain of a CD28 polypeptide having the sequences YMNM (SEQ ID NO: 29) and/or PYAP (SEQ ID NO: 30). In the context of the present invention an intracellular domain of a CD28 polypeptide having the sequences YMNM (SEQ ID NO: 29) and/or PYAP (SEQ ID NO: 30) characterized by a CD28 activity, defined as cytokine production, proliferation and lytic activity of a transduced cell described herein, like e.g. a transduced T cell. Accordingly, in the context of the present invention the intracellular domain of the PD-1-CD28 fusion protein of the present invention has the amino acid sequence of SEQ ID NO: 22 (human) (as encoded by the cDNA sequence shown in SEQ ID NO: 21) or SEQ ID NO: 12 (mouse/murine) (as encoded by the cDNA sequence shown in SEQ ID NO: 11). However, in the fusion protein of the present invention, one or both of these domains may be mutated to FMNM (SEQ ID NO: 31) and/or AYAA (SEQ ID NO: 32), respectively. Either of these mutations reduces the ability of the fusion protein to release cytokines without affecting its ability to proliferate and can advantageously be used to prolong the viability and thus the therapeutic potential of the transduced cells. Or, in other words, such a non-functional mutation preferably enhances the persistence of the cells which are transduced with the herein provided fusion protein in vivo. These signaling motifs may, however, be present at any site within the intracellular domain of the herein provided fusion protein.

Accordingly, in the context of the present invention the PD-1-CD28 fusion protein may comprise the amino acids 170 to 218, preferably the amino acids 178 to 218 of the amino acid sequence of CD28 as shown in SEQ ID NO: 26 (mouse full length CD28 as encoded by cDNA sequence shown in SEQ ID NO: 25). In the context of the present invention the intracellular CD28 polypeptide may be of any length provided that the intracellular domain of the fusion protein of the present invention comprises the sequences YMNM (SEQ ID NO: 29) and/or PYAP (SEQ ID NO: 30). Accordingly, in the context of the present invention the intracellular domain of the CD28 of the PD-1-CD28 fusion protein may comprise a sequence derived from the intracellular domain of CD28 polypeptide having the sequences YMNM (SEQ ID NO: 29) and/or PYAP (SEQ ID NO: 30). For example, the CD28 polypeptide which is comprised in the fusion protein of the present invention may comprise or consist of the amino acid sequence as shown in SEQ ID NO: 12 (as encoded by the cDNA sequence shown in SEQ ID NO: 11). As mentioned, the fusion protein preferably comprises polypeptides of human origin. Thus, more preferably, the herein provided fusion protein comprises the amino acids 170-220, even more preferably the amino acids 180 to 220 of the amino acid sequence of CD28 as shown in SEQ ID NO: 28 (human full length CD28 as encoded by cDNA sequence shown in SEQ ID NO: 27). For example, the CD28 polypeptide which is comprised in the fusion protein of the present invention may comprise or consist of the amino acid sequence as shown in SEQ ID NO: 22 (as encoded by the cDNA sequence shown in SEQ ID NO: 21). In the context of the present invention the intracellular CD28 polypeptide may be of any length provided that the intracellular domain of the fusion protein of the present invention comprises the sequences YMNM (SEQ ID NO: 29) and/or PYAP (SEQ ID NO: 30). Accordingly, in the context of the present invention the intracellular domain of the CD28 of the PD-1-CD28 fusion protein may comprise a sequence derived from the intracellular domain of CD28 polypeptide having the sequences YMNM (SEQ ID NO: 29) and/or PYAP (SEQ ID NO: 30). For example, the CD28 polypeptide which is comprised in the fusion protein of the present invention may comprise or consist of the amino acid sequence as shown in SEQ ID NO: 12 (murine/mouse) or 22 (human). In the context of the present, the CD28 polypeptide of the PD-1-CD28 fusion protein has the amino acid sequence of SEQ ID NO: 22. In the context of the present, the fusion protein comprises an intracellular domain of a CD28 polypeptide having the sequences YMNM (SEQ ID NO: 29) and/or the PYAP (SEQ ID NO: 30). Accordingly, in the context of the present, the CD28 polypeptide has the amino acid sequence of SEQ ID NO: 22 (human).

Further, the herein provided PD-1-CD28 fusion protein may comprise or consist of an amino acid sequence as shown in SEQ ID NO: 14 (murine/mouse PTM (mPTM)- fusion protein as encoded by the cDNA sequence shown in SEQ ID NO: 13). Most preferably, the herein provided fusion protein comprises or consists of an amino acid sequence as shown in SEQ ID NO: 24 (human PTM (hPTM) fusion protein as encoded by the cDNA sequence shown in SEQ ID NO: 23). Accordingly, the present invention relates to a PD-1-CD28 fusion protein which has the amino acid sequence of SEQ ID NO: 24.

Further, the present invention relates to a fusion of protein which consists of SEQ ID NO: 24, wherein said fusion protein has
(a) a PD-1 polypeptide comprising a sequence which has up to 1, 2, 3, 4, 5, 6, 7, 8, 9 or 10, preferably 1 to 8, more preferably 1 to 6, even more preferably 1 to 5, even more preferably 1 or 2, or even more preferably 1 substitution(s), deletion(s) or insertion(s) in comparison to amino acid sequence as shown in SEQ ID NO: 18 and which is characterized by having a PD-L1 or PD-L2 binding activity;
(b) a transmembrane domain of PD-1 which has the amino acid sequence of SEQ ID NO: 20; and
(c) a CD28 polypeptide that comprises a sequence derived from the intracellular domain of a CD28 polypeptide having the sequences YMNM (SEQ ID NO: 29) and/or PYAP (SEQ ID NO: 30).

As described above, the binding PD-L1 and/or PD-L2 binding activity is defined as the ability to bind the PD-L1 and/or PD-L2 ligand either with the same, enhanced or reduced affinity as compared to the natural full length PD-1 protein (e.g. a protein having the amino acid sequence as shown in SEQ ID NO: 4 (as encoded by the cDNA sequence shown in SEQ ID NO: 3). Accordingly, in the context of the present invention, the PD-1 polypeptide which comprises the extracellular domain of PD-1 may bind to the PD-L1 and/or PD-L2 ligand with the same binding as the natural full length PD-1 protein does. Alternatively, in the context of the present invention, the PD-1 polypeptide which comprises the extracellular domain may bind to PD-L1 and/or PD-L2 ligand with a binding affinity that is at least 1000, 100, 50, 40, 30, 20, 10, 5-fold higher (i.e. enhanced) or lower (i.e. reduced) compared to the natural full length PD-1 protein. Further, methods for the determination of the PD-L1 and/or PD-L2 binding activity are well known to the skilled person and described herein above.

In the context of the present invention, the term "PD-1" relates to the programmed cell death protein 1, also known as PD-1 and CD279 (cluster of differentiation 279). PD-1 is a protein that in humans is encoded by the PDCD1 gene. Moreover, PD-1 is a cell surface receptor that belongs to the immunoglobulin superfamily and is expressed on T cells and pro-B cells. PD-1 is known to bind to two ligands, PD-L1 and PD-L2. PD-1 and its ligands play an important role in down regulating the immune system by preventing the activation of T cells, which in turn reduces autoimmunity and promotes self-tolerance. The inhibitory effect of PD-1 is accomplished through a dual mechanism of promoting apoptosis (programmed cell death) in antigen specific T cells in lymph nodes while simultaneously reducing apoptosis in regulatory T cells (suppressor T cells). The protein sequences of the human and mouse PD-1 are shown herein in SEQ ID NO: 4 (as encoded by the cDNA sequence shown in SEQ ID NO: 3) or SEQ ID NO: 2 (as encoded by the cDNA sequence shown in SEQ ID NO: 1). The nucleic acid sequences of the human and mouse PD-1 are shown in SEQ ID NOs: 3 (human) and 1 (murine/mouse), respectively.

In the context of the present invention, the term "CD28" refers to the receptor "cluster of differentiation 28". CD28 is one of the proteins expressed on T cells that provide costimulatory signals required for T cell activation and survival. T cell stimulation through CD28 in addition to the T cell receptor (TCR) can provide a potent signal for the production of various interleukins (e.g. IL-6). CD28 is the receptor for CD80 (B7.1) and CD86 (B7.2) proteins. The amino acid sequences of the human and mouse CD28 protein are shown herein as SEQ ID NO: 28 (as encoded by the cDNA sequence shown in SEQ ID NO: 27) or SEQ ID NO: 26 (as encoded by the cDNA sequence shown in SEQ ID NO: 25). The nucleic acid sequences of the human and mouse CD28 are shown in SEQ ID NOs: 27 (human) and 25 (murine/mouse), respectively.

In the context of the present invention, the term "operably linked" refers to functional linkage between at least two protein sequences, i.e. between the herein described PD-1 polypeptide comprising the extracellular domain and the transmembrane domain of PD-1 and the intracellular domain of CD28. In the context of the present invention, the PD-1 polypeptide and the CD28 polypeptide as comprised in the fusion proteins of the present invention may be covalently linked. The covalent linking of a PD-1 polypeptide which comprises the extracellular domain and the transmembrane domain of PD-1 with an intracellular domain of a CD28 polypeptide results in a fusion protein in which said PD-1 polypeptide is connected via its C-terminus to the N-terminus of the CD28 polypeptide. A covalent bond is a chemical bonding that is characterized by the sharing of pairs of electrons between atoms, as, inter alia, obtained by the herein exemplified cross-binding via chemical compounds. However, also the recombinant production of constructs as disclosed herein, i.e. PD-1 polypeptide comprising the extracellular domain and the transmembrane domain of PD-1 and a covalently bound intracellular domain of a CD28 polypeptide is envisaged. In the context of the present invention, "operably linked" refers to a functional linkage between at least two polypeptides which means that both polypeptides retain their functionalities.

Moreover, the herein provided fusion protein may comprise a linker (or "spacer"). A linker is usually a peptide having a length of up to 20 amino acids. Accordingly, in the context of the present invention the linker may have a length of 1, 2, 3, 4, 5, 6, 7, 8, 9, 10, 11, 12, 13, 14, 15, 16, 17, 18, 19 or 20 amino acids. For example, the herein provided fusion protein may comprise a linker between the PD-1 polypeptide and the CD28 polypeptide. Such linkers have that advantage that they can make it more likely that the different polypeptides of the fusion protein (i.e. the PD-1 polypeptide and the CD28 polypeptide) fold independently and behave as expected. Thus, in the context of the present invention, the PD-1 polypeptide and the CD28 polypeptide may be comprised in a single-chain multi-functional polypeptide. A single-chain PD-1-CD28 fusion construct e.g. may consist of (a) polypeptide(s) comprising (a) PD-1 derived domain(s) and (a) intracellular domain of a CD28 polypeptide. Said domains are connected by a polypeptide linker, wherein said linker is disposed between said PD-1-derived domain(s) and said intracellular CD28 polypeptide domain.

In the context of the present invention, the term "N-teliiinus" may be used interchangeably with the amino terminus of a polypeptide, the NH2-terminus, the N-terminal end or amine-terminus. The term means the natural start of a protein or polypeptide.

In the context of the present invention, the term "C-terminus" may be used interchangeably with the carboxy terminus of a polypeptide, the carboxyl-terminus, the carboxy-terminus, the C-terminal tail, the C-terminal end or COOH-terminus. The term means the natural end of a protein or polypeptide.

Herein the term "extracellular domain", in particular in the context of the extracellular domain of PD-1, refers to the part of the receptor (i.e. of PD-1) that sticks out of the membrane on the outside of the cell. The activity of the extracellular domain is to bind to a specific ligand (e.g. PD-L1 or PD-L2). In the context of the present invention the extracellular domain of the PD-1-CD28 fusion protein has the amino acid/polypeptide sequence of SEQ ID NO: 18 or a polypeptide sequence which has up to 1, 2, 3, 4, 5, 6, 7, 8, 9 or 10 substitution(s), deletion(s) or insertion(s) in comparison to SEQ ID NO: 18 and which is characterized by having PD-L1 and/or PD-L2 binding activity as described herein above. Herein the term "transmembrane domain", in particular in the context of transmembrane domain of PD-1, refers to the part of the receptor (i.e. PD-1) which is naturally located within the membrane of the cell (e.g. the T cell). In the context of the present invention the transmembrane domain of PD-1 has the amino acid sequence of SEQ ID NO: 20 or an amino acid sequence which has up to 1, 2, 3, 4, 5, 6, 7, 8, 9 or 10 substitution(s), deletion(s) or insertion(s) in comparison to SEQ ID NO: 20 and which is characterized by showing the same or preferably an enhanced signal transduction activity as described herein above. Herein the term "intracellular domain", in particular in the context of intracellular domain of CD28, refers to the cytoplasmic domain of the receptor (i.e. CD28). In the context of the present invention the intracellular domain refers to an amino acid sequence which is derived from the intracellular domain of a CD28 polypeptide having the sequences YMNM (SEQ ID NO: 29) and/or PYAP (SEQ ID NO: 30), like the amino acid sequence shown in SEQ ID NO: 22. The intracellular domain interacts with the interior of the cell.

The production of the fusion proteins of the present invention is commonly known in the art. For example, the fusion protein as described herein may be created through genetic engineering of a fusion gene. This typically involves removing the stop codon from a cDNA sequence coding for the first polypeptide (i.e. the PD-1 polypeptide), then appending the cDNA sequence of the second polypeptide (i.e. the CD28 polypeptide) in frame through ligation or overlap extension PCR. That DNA sequence can then be expressed by a cell as a single protein. For example, the fusion protein of the present invention can be generated by overlap PCR and recombinant expression cloning into a retroviral vector (e.g. the pMP71 vector) as described in the illustrative appended examples.

Also encompassed by the present invention are (a) nucleic acid molecule(s) encoding the fusion proteins of the invention.

The term "nucleic acid molecule" relates to the sequence of bases comprising purine- and pyrimidine bases which are comprised by polynucleotides, whereby said bases represent the primary structure of a nucleic acid molecule. Herein, the term "nucleic acid molecule" includes DNA, cDNA, genomic DNA, RNA, synthetic forms of DNA and mixed polymers comprising two or more of these molecules. In addition, the term "nucleic acid molecule" includes both, sense and antisense strands. Moreover, the herein described "nucleic acid molecule" may contain non-natural or derivatized nucleotide bases, as will be readily appreciated by those skilled in the art. Exemplary nucleic acid molecules encoding the human and mouse fusion protein of the present invention are shown in SEQ ID NO: 23 (human) or SEQ ID NO: 13 (mouse).

The nucleic acid molecules of the invention may be under the control of regulatory sequences. For example, promoters, transcriptional enhancers and/or sequences which allow for induced expression of the fusion protein of the invention may be employed. In the context of the present invention, the nucleic acid molecules are expressed under the control of constitutive or inducible promoter. Suitable promoters are e.g. the CMV promoter (Qin et al., PLoS One 5(5) (2010), e10611), the UBC promoter (Qin et al., PLoS One 5(5) (2010), e10611), PGK (Qin et al., PLoS One 5(5) (2010), e10611), the EF1A promoter (Qin et al., PLoS One 5(5) (2010), e10611), the CAGG promoter (Qin et al., PLoS One 5(5) (2010), e10611), the SV40 promoter (Qin et al., PLoS One 5(5) (2010), e10611), the COPIA promoter (Qin et al., PLoS One 5(5) (2010), e10611), the ACT5C promoter (Qin et al., PLoS One 5(5) (2010), e10611), the TRE promoter (Qin et al., PLoS One. 5(5) (2010), e10611), the Oct3/4 promoter (Chang et al., Molecular Therapy 9 (2004), S367-S367 (doi: 10.1016/j.ymthe.2004.06.904)), or the Nanog promoter (Wu et al., Cell Res. 15(5) (2005), 317-24).

The term "regulatory sequence" refers to DNA sequences, which are necessary to effect the expression of coding sequences to which they are ligated. The nature of such control sequences differs depending upon the host organism. In prokaryotes, control sequences generally include promoter, ribosomal binding site, and terminators. In eukaryotes generally control sequences include promoters, terminators and, in some instances, enhancers, transactivators or transcription factors. The term "control sequence" is intended to include, at a minimum, all components the presence of which are necessary for expression, and may also include additional advantageous components.

Furthermore, it is envisaged for further purposes that nucleic acid molecules may contain, for example, thioester bonds and/or nucleotide analogues. Said modifications may be useful for the stabilization of the nucleic acid molecule against endo- and/or exonucleases in the cell. Said nucleic acid molecules may be transcribed by an appropriate vector containing a chimeric gene which allows for the transcription of said nucleic acid molecule in the cell. In this respect, it is also to be understood that such polynucleotide can be used for "gene targeting" or "gene therapeutic" approaches. In another embodiment said nucleic acid molecules are labeled. Methods for the detection of nucleic acids are well known in the art, e.g., Southern and Northern blotting, PCR or primer extension. This embodiment may be useful for screening methods for verifying successful introduction of the nucleic acid molecules described above during gene therapy approaches. Said nucleic acid molecule(s) may be a recombinantly produced chimeric nucleic acid molecule comprising any of the aforementioned nucleic acid molecules either alone or in combination. In the context of the present invention, the nucleic acid molecule is part of a vector.

The present invention therefore also relates to vectors comprising the nucleic acid molecule described in the present invention. Herein the term "vector" relates to a circular or linear nucleic acid molecule which can autonomously replicate in a host cell (i.e. in a transduced cell) into which it has been introduced. The "vector" as used herein particularly refers to a plasmid, a cosmid, a virus, a bacteriophage and other vectors commonly used in genetic engineering. In a preferred embodiment, the vector of the invention is suitable for the transformation of cells, preferably of T cells.

Accordingly, in one aspect of the invention, the vector as provided herein is an expression vector. Expression vectors have been widely described in the literature. In particular, the herein provided vector preferably comprises a recombinant polynucleotide (i.e. a nucleic acid molecule encoding the fusion protein of the present invention) as well as expression control sequences operably linked to the nucleotide sequence to be expressed. The vector as provided herein preferably further comprises a promoter. The herein described vector may also comprise a selection marker gene and a replication-origin ensuring replication in the host (i.e. the transduced cell). Moreover, the herein provided vector may also comprise a termination signal for transcription. Between the promoter and the termination signal there is preferably at least one restriction site or a polylinker which enables the insertion of a nucleic acid molecule (e.g. a nucleic acid molecule encoding the fusion protein of the invention) desired to be expressed. The skilled person knows how such insertion can be put into practice. Examples of vectors suitable to comprise a nucleic acid molecule of the present invention to form the vector of the present invention are known in the art. For example, in context of the invention suitable vectors include cosmids, plasmids (e.g., naked or contained in liposomes) and viruses (e.g., lentiviruses, retroviruses, adenoviruses, and adeno-associated viruses) that incorporate the nucleic acid molecule of the invention (i.e. the nucleic acid molecule encoding the fusion protein of the present invention). Preferably, the vector of the present invention is a viral vector. More preferably, the vector of the present invention is a lentiviral vector, and even more preferably, the vector of the present invention is a retroviral vector (e.g. the pMP71 vector). Accordingly, in the context of the present invention, the vector is a lentiviral vector or a retroviral vector. The vector of the present invention allows for constitutive or conditional expression of the nucleic acid molecule encoding the PD-1-CD28 fusion protein of the present invention. In this context, suitable retoviral vectors for the expression of the fusion protein of the present invention are known in the art such as SAMEN CMV/SRa (Clay et al., J. Immunol. 163 (1999), 507-513), LZRS-id3-IHRES (Heemskerk et al., J. Exp. Med. 186 (1997), 1597-1602), FeLV (Neil et al., Nature 308 (1984), 814-820), SAX (Kantoff et al., Proc. Natl. Acad. Sci. USA 83 (1986), 6563-6567), pDOL (Desiderio, J. Exp. Med. 167 (1988), 372-388), N2 (Kasid et al., Proc. Natl. Acad. Sci. USA 87 (1990), 473-477), LNL6 (Tiberghien et al., Blood 84 (1994), 1333-1341), pZipNEO (Chen et al., J. Immunol. 153 (1994), 3630-3638), LASN (Mullen et al., Hum. Gene Ther. 7 (1996), 1123-1129), pG1XsNa (Taylor et al., J. Exp. Med. 184 (1996), 2031-2036), LCNX (Sun et al., Hum. Gene Ther. 8 (1997), 1041-1048), SFG (Gallardo et al., Blood 90 (1997), LXSN (Sun et al., Hum. Gene Ther. 8 (1997), 1041-1048), SFG (Gallardo et al., Blood 90 (1997), 952-957), HMB-Hb-Hu (Vieillard et al., Proc. Natl. Acad. Sci. USA 94 (1997), 11595-11600), pMV7 (Cochlovius et al., Cancer Immunol. Immunother. 46 (1998), 61-66), pSTITCH (Weitjens et al., Gene Ther 5 (1998), 1195-1203), pLZR (Yang et al., Hum. Gene Ther. 10 (1999), 123-132), pBAG (Wu et al., Hum. Gene Ther. 10 (1999), 977-982), rKat.43.267bn (Gilham et al., J. Immunother. 25 (2002), 139-151), pLGSN (Engels et al., Hum. Gene Ther. 14 (2003), 1155-1168), pMP71 (Engels et al., Hum. Gene Ther. 14 (2003), 1155-1168), pGCSAM (Morgan et al., J. Immunol. 171 (2003), 3287-3295), pMSGV (Zhao et al., J. Immunol. 174 (2005), 4415-4423), or pMX (de Witte et al., J. Immunol. 181 (2008), 5128-5136). Further, in the context of the present invention suitable lentiviral vectors for the expression of the fusion protein of the present invention are, e.g. PL-SIN lentiviral vector (Hotta et al., Nat Methods. 6(5) (2009), 370-376), p156RRL-sinPPT-CMV-GFP-PRE/NheI (Campeau et al., PLoS One 4(8) (2009), e6529), pCMVR8.74 (Addgene Catalogoue No.:22036), FUGW (Lois et al., Science 295(5556) (2002), 868-872, pLVX-EF1 (Addgene Catalogue No.: 64368), pLVE (Brunger et al., Proc Natl Acad Sci USA 111(9) (2014), E798-806), pCDH1-MCS1-EF1 (Hu et al., Mol Cancer Res. 7(11) (2009), 1756-1770), pSLIK (Wang et al., Nat Cell Biol. 16(4) (2014), 345-356), pLJM1 (Solomon et al., Nat Genet. 45(12) (2013), 1428-30), pLX302 (Kang et al., Sci Signal. 6(287) (2013), rs13), pHR-IG (Xie et al., J Cereb Blood Flow Metab. 33(12) (2013), 1875-85), pRRLSIN (Addgene Catalogoue No.: 62053), pLS (Miyoshi et al., J Virol. 72(10) (1998), 8150-8157), pLL3.7 (Lazebnik et al., J Biol Chem. 283(7) (2008), 11078-82), FRIG (Raissi et al., Mol Cell Neurosci. 57 (2013), 23-32), pWPT (Ritz-Laser et al., Diabetologia. 46(6) (2003), 810-821), pBOB (Marr et al., J Mol Neurosci. 22(1-2) (2004), 5-11), or pLEX (Addgene Catalogue No.: 27976).

The invention also relates to transduced cells expressing a fusion protein encoded by a nucleic acid molecule encoding the fusion protein of the present invention. Accordingly, in the context of the present, the transduced cell may comprise a nucleic acid molecule encoding the fusion protein of the present invention or a vector of the present invention which expresses a fusion protein of the present invention.

In the context of the present invention, the term "transduced cell" relates to a genetically modified cell (i.e. a cell wherein a nucleic acid molecule has been introduced deliberately). The herein provided transduced cell may comprise the vector of the present invention. Preferably, the herein provided transduced cell comprises the nucleic acid molecule (encoding the fusion protein) of the present invention and/or the vector of the present invention. The transduced cell of the invention may be a cell which transiently or stably expresses the foreign DNA (i.e. the nucleic acid molecule which has been introduced into the cell). In particular, the nucleic acid molecule encoding the fusion protein of the present invention can be stably integrated into the genome of the cell by using a retroviral or lentiviral transduction. By using mRNA transfection, the nucleic acid molecule encoding the fusion protein of the present invention may be expressed transiently. Preferably, the herein provided transduced cell has been genetically modified by introducing a nucleic acid molecule in the cell via a viral vector (e.g. a retroviral vector or a lentiviral vector). The expression can be constitutive or constitutional, depending on the system used. The PD-1-CD28 fusion protein is expressed on the surface of the herein provided transduced cell. The extracellular proportion of the PD-1 polypeptide of the fusion protein can be detected on the cell surface, while the intracellular (both transmembrane and e.g. a part of the intracellular domain of the PD-1 polypeptide) are bound to the membrane but are not detectable on cell surface. The detection of the extracellular domain of the PD-1 polypeptide can be carried out by using an antibody which specifically binds to this extracellular domain of the PD-1 polypeptide. Examples for such antibodies are well known in the art and include clone EH12.2H7 (commercially available from BioLegend, catalogue no.: 329911), clone J116 (commercially available from eBioscience, catalogue no.: 16-9989-80), J105 (commercially available from eBioscience, catalogue no.: 8012-2799) or MiH4 (commercially available from eBioscience, catalogue no.: 14-9969). The extracellular domain can be detected using these antibodies by flow cytometry or microscopy. The transduced cell of the present invention may be, e.g., a CD4+-T cell, a CD8+-T cell, a γδ T cell, a natural killer (NK) T cell, a natural killer (NK) cell, a tumor-infiltrating lymphocyte (TIL) cell, a myeloid cell, or a mesenchymal stem cell. Preferably, the herein provided transduced cell is a T cell (e.g. an autologous T cell), more preferably, the transduced cell is a CD8+ T cell. Accordingly, in the context of the present invention, the transduced cell is a CD8+ T cell. Further, in the context of the present invention, the transduced cell is an autologous T cell. Accordingly, in the context of the present invention, the transduced cell is preferably an autologous CD8+ T cell. In addition to the use of autologous cells (e.g. T cells) isolated from the subject, the present invention also comprehends the use of allogeneic cells. Accordingly, in the context of the present invention the transduced cell may also be an allogeneic cell, such as an allogeneic CD8+ T cell. Alternately or additionally, the invention provides a transduced CD4+ T cell, which may be an autologous CD4+ T cell or an allogeneic CD4+ T cell. Alternately or additionally, the invention provides populations of transduced CD4+ T cells and/or CD8+ T cells (including but not limited to populations comprising transduced CD4+ T cells, populations comprising transduced CD8+ T cells, and populations comprising both transduced CD4+ T cells and transduced CD8+ T cells), wherein the transduced cells may be autologous and/or allogenic (e.g., the population may comprise only autologous cells, only allogenic cells, or combinations of both autologous and allogeneic cells). The populations of T cells of the invention as described herein may comprise both transduced and non-transduced T cells.

The use of allogeneic cells is based on the fact that cells, preferably T cells can recognize a specific antigen epitope presented by foreign antigen-presenting cells (APC), provided that the APC express the MHC molecule, class I or class II, to which the specific responding cell population, i.e. T cell population is restricted, along with the antigen epitope recognized by the T cells. Thus, the term allogeneic refers to cells coming from an unrelated donor individual/subject which is human leukocyte antigen (HLA) compatible to the individual/subject which will be treated by e.g. the herein described PD-1-CD28 fusion protein expressing transduced cell. Autologous cells refer to cells which are isolated/obtained as described herein above from the subject to be treated with the transduced cell described herein.

As described above, the transduced cell of the present invention is transduced with a nucleic acid molecule expressing the herein provided fusion protein. In the case of cells bearing natural anti-tumoral specificity such as tumor-infiltrating lymphocyte cells (TIL, Dudley et al., J Clin Oncol. 31(17) (2013), 2152-2159 (doi: 10.1200/JCO.2012.46.6441)) or antigen-specific cells sorted from the peripheral blood of patients for their tumor-specificity by flow cytometry (Hunsucker et al., Cancer Immunol Res. 3(3) (2015), 228-235 (doi: 10.1158/2326-6066.CIR-14-0001)), the cells described herein would only be transduced with the fusion protein of the present invention. However, the transduced cell of the invention may be co-transduced with further nucleic acid molecules; e.g. with a nucleic acid molecule encoding a T cell receptor or a chimeric antigen receptor.

In accordance with this invention, the term "T cell receptor" is commonly known in the art. In particular, herein the term "T cell receptor" refers to any T cell receptor, provided that the following three criteria are fulfilled: (i) tumor specificity, (ii) recognition of (most) tumor cells, which means that an antigen or target should be expressed in (most) tumor cells and (iii) that the TCR matches to the HLA-type of the subject to be treated. In this context, suitable T cell receptors which fulfill the above mentioned three criteria are known in the art such as receptors recognizing WT1 (Wilms tumor specific antigen 1; for sequence information(s) see, e.g., Sugiyama, Japanese Journal of Clinical Oncology 40 (2010), 377-87), MAGE (for sequence see, e.g., WO-A1 2007/032255 and PCT/US2011/57272), SSX (U.S. Provisional Application No. 61/388,983), NY-ESO-1 (for sequence information(s) see, e.g., PCT/GB2005/001924) and/or HER2neu (for sequence information(s) see WO-A1 2011/0280894).

The term "chimeric antigen receptor" or "chimeric receptor" is known in the art and refers to a receptor constituted of an extracellular portion of a single chain antibody domain fused by a spacer sequence to the signal domains of CD3z and CD28. Again, this chimeric antigen receptor should provide tumor specify and allow for the recognition of most tumor cells. Suitable chimeric receptors include: anti-EGFRv3-CAR (for sequence see WO-A1 2012/138475), anti-CD22-CAR (see WO-A1 2013/059593), anti-BCMA-CAR (see WO-A1 2013/154760), anti-CD19-CAR (see WO-A1 2012/079000 or US-A1 2014/0271635), anti-CD123-CAR (see US-A1 2014/0271582), anti-CD30-CAR (see WO-A1 2015/028444) or anti-Mesothelin-CAR (see WO-A1 2013/142034).

The present invention also relates to a method for the production of a transduced cell expressing a fusion protein of the invention, comprising the steps of transducing a cell with a vector of the present invention, culturing the transduced cell under conditions allowing the expressing of the fusion protein in or on said transduced cell and recovering said transduced cell.

In the context of the present invention, the transduced cell of the present invention is preferably produced by the following process: cells (e.g., T cells) are isolated/obtained from a subject (preferably a human patient). Methods for isolating/obtaining cells (e.g. T cells) from patients or from donors are well known in the art and in the context of the present the cells (e.g. T cells) from patients or from donors may be isolated by blood draw or removal of bone marrow. After isolating/obtaining cells as a sample of the patient, the cells (e.g. T cells) are separated from the other ingredients of the sample. Several methods for separating cells (e.g. T cells) from the sample are known and include, without being limiting, e.g. leukapheresis for obtaining cells from the peripheral blood sample from a patient or from a donor, isolating/obtaining cells by using a FACSort apparatus, picking living of dead cells from fresh biopsy specimens harboring living cells by hand or by using a micromanipulator (see, e.g., Dudley, Immunother. 26 (2003), 332-342; Robbins, Clin. Oncol. 29 (2011), 917-924 or Leisegang, J. Mol. Med. 86 (2008), 573-58). The methods and processes disclosed in this paragraph and otherwise disclosed herein are preferably performed with respect to CD8+ T cells, but are also applicable to other T cell types such as CD4+ T cells.

Herein the term "fresh patient biopsy" refers to tissue (preferably tumor tissue) removed from a subject by surgical or any other known means as well as tumor cell lines or (isolated) cells from a tumor tissue/tumor cell. The isolated/obtained cells T cells (e.g. CD8+ T cells) are subsequently cultivated and expanded, e.g., by using an anti-CD3 antibody, by using anti-CD3 and anti-CD28 monoclonal antibodies and/or by using an anti-CD3 antibody, an anti-CD28 antibody and interleukin-2 (IL-2) (see, e.g., Dudley, Immunother. 26 (2003), 332-342 or Dudley, Clin. Oncol. 26 (2008), 5233-5239).

In a subsequent step the cells (e.g. T cells) are artificially/genetically modified/transduced by methods known in the art (see, e.g., Lemoine, J Gene Med 6 (2004), 374-386). Methods for transducing cells (e.g. T cells) are known in the art and include, without being limited, in a case where nucleic acid or a recombinant nucleic acid is transduced, for example, an electroporation method, calcium phosphate method, cationic lipid method or liposome method. The nucleic acid to be transduced can be conventionally and highly efficiently transduced by using a commercially available transfection reagent, for example, Lipofectamine (manufactured by Invitrogen, catalogue no.: 11668027). In a case where a vector is used, the vector can be transduced in the same manner as the above-mentioned nucleic acid as long as the vector is a plasmid vector (i.e. a vector which is not a viral vector In the context of the present invention, the methods for transducing cells (e.g. T cells) include retroviral or lentiviral T cell transduction as well as mRNA transfection. "mRNA transfection" refers to a method well known to those skilled in the art to transiently express a protein of interest, like in the present case the PD-1-CD28 fusion protein of the present invention, in a cell to be transduced. In brief cells may be electroporated with the mRNA coding for the fusion protein of the present by using an electroporation system (such as e.g. Gene Pulser, Bio-Rad) and thereafter cultured by standard cell (e.g. T cell) culture protocol as described above (see Zhao et al., Mol Ther. 13(1) (2006), 151-159.) Preferably, the transduced cell of the invention is a T cell (most preferably a CD8+ T cell) and is generated by lentiviral, or most preferably retroviral T cell transduction.

In this context, suitable retroviral vectors for transducing cells (e.g. T cells) are known in the art such as SAMEN CMV/SRa (Clay et al., J. Immunol. 163 (1999), 507-513), LZRS-id3-IHRES (Heemskerk et al., J. Exp. Med. 186 (1997), 1597-1602), FeLV (Neil et al., Nature 308 (1984), 814-820), SAX (Kantoff et al., Proc. Natl. Acad. Sci. USA 83 (1986), 6563-6567), pDOL (Desiderio, J. Exp. Med. 167 (1988), 372-388), N2 (Kasid et al., Proc. Natl. Acad. Sci. USA 87 (1990), 473-477), LNL6 (Tiberghien et al., Blood 84 (1994), 1333-1341), pZipNEO (Chen et al., J. Immunol. 153 (1994), 3630-3638), LASN (Mullen et al., Hum. Gene Ther. 7 (1996), 1123-1129), pG1XsNa (Taylor et al., J. Exp. Med. 184 (1996), 2031-2036), LCNX (Sun et al., Hum. Gene Ther. 8 (1997), 1041-1048), SFG (Gallardo et al., Blood 90 (1997), LXSN (Sun et al., Hum. Gene Ther. 8 (1997), 1041-1048), SFG (Gallardo et al., Blood 90 (1997), 952-957), HMB-Hb-Hu (Vieillard et al., Proc. Natl. Acad. Sci. USA 94 (1997), 11595-11600), pMV7 (Cochlovius et al., Cancer Immunol. Immunother. 46 (1998), 61-66), pSTITCH (Weitjens et al., Gene Ther 5 (1998), 1195-1203), pLZR (Yang et al., Hum. Gene Ther. 10 (1999), 123-132), pBAG (Wu et al., Hum. Gene Ther. 10 (1999), 977-982), rKat.43.267bn (Gilham et al., J Immunother. 25 (2002), 139-151), pLGSN (Engels et al., Hum. Gene Ther. 14 (2003), 1155-1168), pMP71 (Engels et al., Hum. Gene Ther. 14 (2003), 1155-1168), pGCSAM (Morgan et al., J. Immunol. 171 (2003), 3287-3295), pMSGV (Zhao et al., J. Immunol. 174 (2005), 4415-4423), or pMX (de Witte et al., J. Immunol. 181 (2008), 5128-5136). In the context of the present invention, suitable lentiviral vector for transducing cells (e.g. T cells) are, e.g. PL-SIN lentiviral vector (Hotta et al., Nat Methods. 6(5) (2009), 370-376), p156RRL-sinPPT-CMV-GFP-PRE/NheI (Campeau et al., PLoS One 4(8) (2009), e6529), pCMVR8.74 (Addgene Catalogoue No.:22036), FUGW (Lois et al., Science 295(5556) (2002), 868-872, pLVX-EF1 (Addgene Catalogue No.: 64368), pLVE (Brunger et al., Proc Natl Acad Sci USA 111(9) (2014), E798-806), pCDH1-MCS1-EF1 (Hu et al., Mol Cancer Res. 7(11) (2009), 1756-1770), pSLIK (Wang et al., Nat Cell Biol. 16(4) (2014), 345-356), pLJM1 (Solomon et al., Nat Genet. 45(12) (2013), 1428-30), pLX302 (Kang et al., Sci Signal. 6(287) (2013), rs13), pHR-IG (Xie et al., J Cereb Blood Flow Metab. 33(12) (2013), 1875-85), pRRLSIN (Addgene Catalogoue No.: 62053), pLS (Miyoshi et al., J Virol. 72(10) (1998), 8150-8157), pLL3.7 (Lazebnik et al., J Biol Chem. 283(7) (2008), 11078-82), FRIG (Raissi et al., Mol Cell Neurosci. 57 (2013), 23-32), pWPT (Ritz-Laser et al., Diabetologia. 46(6) (2003), 810-821), pBOB (Man et al., J Mol Neurosci. 22(1-2) (2004), 5-11), or pLEX (Addgene Catalogue No.: 27976).

The transduced cell/cells of the present invention is/are preferably grown under controlled conditions, outside of their natural environment. In particular, the term "culturing" means that cells (e.g. the transduced cell(s) of the invention) which are derived from multi-cellular eukaryotes (preferably from a human patient) are grown in vitro. Culturing cells is a laboratory technique of keeping cells alive which are separated from their original tissue source. Herein, the transduced cell of the present invention is cultured under conditions allowing the expression of the fusion protein of the present invention in or on said transduced cells. Conditions which allow the expression or a transgene (i.e. of the fusion protein of the present invention) are commonly known in the art and include, e.g., agonistic anti-CD3- and anti-CD28 antibodies and the addition of cytokines such as interleukin 2 (IL-2), interleukin 7 (IL-7), interleukin 12 (IL-12) and/or interleukin 15 (IL-15). After expression of the fusion protein of the present invention in the cultured transduced cell, the transduced cell is recovered (i.e. re-extracted) from the culture (i.e. from the culture medium).

Also encompassed by the invention is a transduced cell expressing a fusion protein encoded by a nucleic acid molecule of the invention obtainable by the method of the present invention.

Furthermore, the invention provides a pharmaceutical composition/medicament comprising a transduced cell expressing a fusion protein of the present invention or a transduced cell as obtained by/produced by the method disclosed above. In the context of the present invention, said composition is a pharmaceutical composition further comprising, optionally, suitable formulations of carrier, stabilizers and/or excipients.

In accordance with the present invention, the term "medicament" is used interchangeably with the term "pharmaceutical composition" and relates to a composition for administration to a patient, preferably a human patient. In the context of the present invention that medicament/pharmaceutical composition is to be administered to a patient from which the transduced cells were isolated/obtained. In the context of the present invention, the patient refers to a human patient. Furthermore, in the context of the present invention that patient suffers from a disease characterized by expressing a ligand for PD-1 (i.e. PD-L1 and/or PD-L2). In the context of the present invention diseases which are characterized by expressing a ligand for PD-1 (i.e. PD-L1 and/or PD-L2) are known in the art and include e.g. lung cancer (Dong et al., Nat Med. 8(8) (2002), 793-800), ovarian cancer (Dong et al., Nat Med. 8(8) (2002), 793-800), melanoma (Dong et al., Nat Med. 8(8) (2002), 793-800), colon cancer (Dong et al., Nat Med. 8(8) (2002), 793-800), gastric cancer (Chen et al., World J Gastroenterol. 9(6) (2003), 1370-1373), renal cell carcinoma (Thompson et al., 104(10) (2005), 2084-91), esophageal carcinoma (Ohigashi et al., 11(8) (2005), 2947-2953), glioma (Wintterle et al., Cancer Res. 63(21) (2003), 7462-7467), urothelial cancer (Nakanishi et al., Cancer Immunol Immunother. 56(8) (2007), 1173-1182), retinoblastoma (Usui et al., Invest Ophthalmol Vis Sci. 47(10) (2006), 4607-4613), breast cancer (Ghebeh et al., Neoplasia 8(3) (2006), 190-198), Non-Hodgkin lymphoma (Xerri et al., Hum Pathol. 39(7) (2008), 1050-1058), pancreatic carcinoma (Geng et al., J Cancer Res Clin Oncol. 134(9) (2008), 1021-1027), Hodgkin's lymphoma (Yamamoto et al., Blood 111(6) (2008), 3220-3224), myeloma (Liu et al., Blood 110(1) (2007), 296-304), hepatocellular carcinoma (Gao et al., Clin Cancer Res. 15(3) (2009), 971-979), leukemia (Kozako et al., Leukemia 23(2) (2009), 375-382), cervical carcinoma (Karim et al., Clin Cancer Res. 15(20) (2009), 6341-6347), cholangiocarcinoma (Ye et al., J Surg Oncol. 100(6) (2009), 500-504), oral cancer (Malaspina et al., Cancer Immunol Immunother. 60(7) (2011), 965-974), head and neck cancer (Badoual et al., Cancer Res. 73(1) (2013), 128-138), or mesothelioma (Mansfield et al., J Thorac Oncol. 9(7) (2014), 1036-1040).

In the context of the present invention the pharmaceutical composition which comprises a transduced cell of the present invention or a transduced cell produced by the method of the present invention is to be administered in combination intervening treatment protocols. Examples of such intervening treatment protocols include but are not limited to, administration of pain medications, administration of chemotherapeutics, surgical handling of the disease or a symptom thereof. Accordingly the treatment regimens as disclosed herein encompass the administration of the transduced cell expressing a fusion protein as described herein together with none, one, or more than one treatment protocol suitable for the treatment or prevention of a disease, or a symptom thereof, as described herein or as known in the art.

Accordingly, in the context of the present invention transduced cell expressing the fusion protein of the present invention can be used for the treatment of a proliferative disease, preferably cancer. More preferably, the herein provided transduced cell expressing the fusion protein of the present invention is used for the treatment of a disease (preferably a cancer), wherein the tumor cells express a ligand for PD-1 (i.e. PD-L1 and/or PD-L2). Cancer types which are preferably treated with the herein provided transduced cell expressing the fusion protein of the present invention are described herein above. Thus, the transduced cell expressing a fusion protein of the present invention encoded by a nucleic acid molecule described herein can be used in a method of treating any disease where tumor cells express a ligand for PD-1 (i.e. PD-L1 and/or PD-L2). The treatment method preferably involves cell collection by a method described above like isolating/collection of the cells by blood draw or removal of bone marrow. Subsequently, the isolated cells are modified virally or by mRNA electroporation with the fusion receptor (and optionally co-transduced with further nucleic acid molecules, e.g. with a nucleic acid molecule encoding a T cell receptor or a chimeric receptor). After cell expansion, as outlined above, cells are transferred intravenously back to the patient. Moreover, the present invention provides a method for the treatment of diseases comprising the steps of isolating cells (e.g. T cells, preferably CD8+ T cells) from a subject, transducing said isolated cells with a nucleic acid encoding the PD-1-CD28 fusion protein as described herein above, co-transducing said isolated cells with further nucleic acid molecules, e.g. with a nucleic acid molecule encoding a T cell receptor or a chimeric receptor as described above, expanding the transduced cells, and administering the transduced cells back to said subject. This treatment method described herein may be repeated e.g. one or two times per week.

The terms "treatment", "treating" and the like are used herein to generally mean obtaining a desired pharmacological and/or physiological effect. The effect may be prophylactic in tennis of completely or partially preventing a disease or symptom thereof and/or may be therapeutic in terms of partially or completely curing a disease and/or adverse effect attributed to the disease. The term "treatment" as used herein covers any treatment of a disease in a subject and includes: (a) preventing and/or ameliorating a proliferative disease (preferably cancer) from occurring in a subject which may be predisposed to the disease; (b) inhibiting the disease, i.e. arresting its development, like the inhibition cancer progression; or (c) relieving the disease, i.e. causing regression of the disease, like the repression of cancer. Preferably, the term "treatment" as used herein relates to medical intervention of an already manifested disorder, like the treatment of a diagnosed cancer.

For the purposes of the present invention the "subject" (or "patient") may be a vertebrate. In context of the present invention, the term "subject" includes both humans and other animals, particularly mammals, and other organisms. Thus, the herein provided methods are applicable to both human therapy and veterinary applications. Accordingly, said subject may be an animal such as a mouse, rat, hamster, rabbit, guinea pig, ferret, cat, dog, chicken, sheep, bovine species, horse, camel, or primate. Preferably, the subject is a mammal. Most preferably the subject is a human being.

As described above, the present invention relates to a "pharmaceutical composition" comprising the herein provided transduced cell expressing the fusion protein of the present invention (encoded by the nucleic acid molecule of the present invention). Said pharmaceutical composition may further comprise a pharmaceutically acceptable carrier, excipient and/or diluent. Examples of suitable pharmaceutical carriers are well known in the art and include phosphate buffered saline solutions, water, emulsions, such as oil/water emulsions, various types of wetting agents, sterile solutions etc. The carrier may be a solution that is isotonic with the blood of the recipient. Compositions comprising such carriers can be formulated by well known conventional methods. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. For example, the pharmaceutical composition of the invention may be administered to the subject at a dose of $10^4$ to $10^{10}$ cells/kg body weight, preferably $10^5$ to $10^6$ cells/kg body weight. In the context of the present invention the pharmaceutical composition may be administered in such a way that an upscaling of the cells to be administered is performed by starting with a subject dose of about $10^5$ to $10^6$ cells/kg body weight and then going up to dose of $10^{10}$ cells/kg body weight. The pharmaceutical composition of the invention may be administered intravenously (i.e. by intravenous infusion) but also intraperitoneally, intrapleurally, intrathecally, subcutaneously or intranodally. Intravenous carriers include fluid and nutrient replenishers, electrolyte replenishers (such as those based on Ringer's dextrose), and the like preservatives and other additives may also be present in the pharmaceutical composition of the present invention, such as, e.g., antimicrobials, anti-oxidants, chelating agents, inert gases and the like.

The pharmaceutical composition of the present invention may be used in co-therapy in conjunction with, e.g., molecules capable of providing an activation signal for immune effector cells, for cell proliferation or for cell stimulation. Said molecule may be, e.g., a further primary activation signal for T-cells (e.g. a further costimulatory molecule: molecules of B7 family, Ox40L, 4.1 BBL, CD40L, anti-CTLA-4, anti-PD-1), or a further cytokine interleukin (e.g., IL-2).

In context of the present invention, the components of the pharmaceutical composition to be used for therapeutic administration are preferably sterile. Sterility may readily be accomplished by, e.g., filtration through sterile filtration membranes (e.g., 0.2 micron membranes). The pharmaceutical composition of the present invention may be prepared by contacting the components of the pharmaceutical composition uniformly with liquid carriers. After its production, the pharmaceutical composition of the invention may be placed into a container having a sterile access port, for example, an intravenous solution bag or vial having a stopper pierceable by a hypodermic injection needle.

The invention also relates to a method for the treatment of diseases which are characterized by expressing a ligand for PD-1 (i.e. PD-L1 and/or PD-L2) such as, e.g., lung cancer, ovarian cancer, melanoma, colon cancer, gastric cancer, renal cell carcinoma, esophageal carcinoma, glioma, urothelial cancer, retinoblastoma, breast cancer, Non-Hodgkin lymphoma, pancreatic carcinoma, Hodgkin's lymphoma, myeloma, hepatocellular carcinoma, leukemia, cervical carcinoma, cholangiocarcinoma, oral cancer, head and neck cancer, or mesothelioma comprising the administration of a transduced cell as described herein to a subject. In the context of the present invention, said subject is a human (as explained above). In the context of the present invention, a method for the treatment of a disease is described that comprises the steps of isolating cells (e.g. T cells, preferably CD8+ T cells) from a subject, transducing said isolated cells with a nucleic acid encoding the PD-1-CD28 fusion protein as described herein above, and administering the transduced cells to said subject. In the context of the present invention, said transduced cells are administered to said subject by intravenous infusion. Moreover, the present invention provides a method for the treatment of diseases comprising the steps of isolating cells (e.g. T cells, preferably CD8+ T cells) from a subject, transducing said isolated cells with a nucleic acid encoding the PD-1-CD28 fusion protein as described herein above, co-transducing said isolated cells with further nucleic acid molecules, e.g. with a nucleic acid molecule encoding a T cell receptor or a chimeric receptor as described above, expanding the transduced cells, and administering the transduced cells back to said subject.

The above mentioned expanding step of the transduced cells may be performed in the presence of (stimulating) cytokines such as interleukin-2 (IL-2) and/or interleukin-15 (IL-15). In the context of the present invention, the expanding step may also be performed in the presence of interleukin-12 (IL-12), interleukin-7 (IL-7) and/or interleukin-21 (IL-21). In accordance with the present invention, the expanding step of the transduced cells may also be performed in the presence of anti-CD3 and/or anti-CD28 antibodies.

The PD-1-CD28 fusion proteins of the invention may also be combined with other engineered polypeptides as disclosed herein or as known in the art. Such combinations include the co-expression the PD-1-CD28 fusions proteins of the invention and engineered polypeptides in the same cell population and/or within the same cell. Accordingly, combination in the context of the PD1-CD28 fusion protein with another engineered polypeptide may refer to a cell population that, as a whole, expresses both one or more PD1-CD28 fusion proteins of the invention and one or more engineered polypeptides, wherein the individual cells within the population have been engineered according to standard methods known in the art or as described herein to express (a) one or more of a PD1-CD28 fusion protein of the invention or one or more engineered polypeptide; or (b) one or more of a PD1-CD28 fusion protein of the invention and one or more engineered polypeptide.

It is preferred that the combination of one or more PD1-CD28 fusion protein of the invention and one or more engineered polypeptide is co-expression within the same cell, such that the cell concurrently expresses both the one or more PD1-CD28 fusion protein of the invention and the one or more engineered polypeptide and/or such that expression of both the one or more PD1-CD28 fusion protein of the invention and the one or more engineered polypeptide can be detected within the same cell.

Engineered polypeptides that can be co-expressed with one or more PD1-CD28 fusion proteins of the invention include
  chimeric antigen receptors such as described in Milone et al., Mol. Ther. 17(2009), 1453-1464; Carpenito et al., Proc. Natl. Acad. Sci. U.S.A. 106(2009), 3360-3365; Wang et al., Hum. Gene Ther. 18(2007), 712-725; Pule et al., Mol. Ther. 12(2005), 933-941; and Wang et al., Cancer Immunol. Res. 3(2015), 815-826;
  Alpha/beta TCR engineered T cells such as provided in Rapoport et al., Nature Medicine, 21(2015), 914-921;
  Natural TCRs expressed on TILs such as provided in Rosenberg et al., Clin. Cancer Res. 17(2011), 4550-4557;
  Anti-CD3 T cell engagers expressed as soluble polypeptide or presented as transmembrane protein on the cell surface; and
  T-cell Receptor (TCR) fusion proteins (TFP) that comprise a TCR subunit and a human or humanized antibody domain. For example, as known in the art, the TCR subunit may comprise a TCR extracellular domain, a TCR transmembrane domain, and/or a TCR intracellular domain (all references recited in the above paragraph incorporated by reference herein in their entireties).

Where the PD1-CD28 fusion protein and the engineered polypeptide are to be co-expressed in the same cell, the PD-1-CD28 fusion protein of the invention and the second polypeptide can be encoded by different nucleic acids that are both introduced into the same cell. Thus, the invention provides a composition comprising a nucleic acid encoding one or more of a PD1-CD28 fusion protein as described herein (e.g., SEQ ID NO:14 or SEQ ID NO:24, preferably SEQ ID NO:24) and a nucleic acid encoding one or more engineered (second polypeptide as comprised herein). The invention also provides a composition comprising a first and second vector, the first vector comprising a nucleic acid encoding one or more of a PD1-CD28 fusion protein as described herein (e.g., SEQ ID NO:14 or SEQ ID NO:24, preferably SEQ ID NO:24) and the second vector comprising a nucleic acid encoding one or more engineered (second polypeptide as comprised herein). The first and second vectors can be the same or different. For example, as known in the art, the first and second vectors (comprising nucleic acids encoding one or more PD1-CD28 fusion protein of the invention (e.g., SEQ ID NO:14 or SEQ ID NO:24, preferably SEQ ID NO:24) and the one or more engineered (second) polypeptide, respectively) can be the same vector (e.g., the same expression vector) but for the insert encoding the PD1-CD28 fusion protein or the engineered (second) polypeptide. Alternatively, the first and second vectors may be different vectors, e.g., comprising different expression promoters. Thus, the expression of the encoded polypeptides from the first and second vectors can be driven by the same or different promoters. Accordingly, the invention provides a composition comprising (a) a first nucleic acid comprising a first promoter operably linked to a nucleic acid sequence encoding a PD1-CD28 fusion protein of the invention, and/or a first vector comprising the first nucleic acid; and (b) a second nucleic acid comprising a second promoter operably linked to a second nucleic acid sequence encoding an engineered (second) polypeptide, wherein the first and second vectors, and/or first and second promoters, are the same or different.

Alternatively, where the PD1-CD28 fusion protein and the engineered polypeptide are to be co-expressed in the same cell, the PD-1-CD28 fusion protein of the invention and the second polypeptide can be encoded by the same nucleic acid, i.e., a single nucleic acid comprising a sequence that encodes a fusion protein of the invention and a sequence that encodes the second polypeptide. Thus, the invention provides a single nucleic acid comprising a PD1-CD28 fusion protein of the invention and/or an engineered polypeptide as described above. A single nucleic acid comprising both the gene encoding the PD1-CD28 fusion protein of the invention and the gene encoding the co-expressed polypeptide may be used according to standard methods known in the art or described herein for replication/duplication of the nucleic acid and/or components thereof (e.g., replication of the nucleic acid sequences encoding the PD1-CD28 and/or engineered polypeptide), may be used to modify the nucleic acid and/or components thereof, or may be used to express the encoded proteins separately or concurrently. Accordingly, the invention provides a nucleic acid comprising a gene encoding a PD-1-CD28 fusion protein of the invention (e.g., SEQ ID NO:14 or SEQ ID NO:24, preferably SEQ ID NO:24) and a gene encoding an engineered polypeptide (e.g., a chimeric antigen receptor, an alpha/beta T cell receptor, a natural T cell receptor, an anti-CD3 T cell engagers expressed as soluble polypeptide or presented as transmembrane protein on the cell surface, and/or a T-cell Receptor (TCR) fusion protein (TFP) (e.g. that comprise a TCR subunit and a human or humanized antibody domain) as described above). The invention also provides a vector comprising a nucleic acid comprising a gene encoding a PD-1-CD28 fusion protein of the invention (e.g., SEQ ID NO:14 or SEQ ID NO:24, preferably SEQ ID NO:24), a gene encoding an engineered polypeptide (e.g., a chimeric antigen receptor, an alpha/beta T cell receptor, a natural T cell receptor, an anti-CD3 T cell engagers expressed as soluble polypeptide or presented as transmembrane protein on the cell surface, and/or a T-cell Receptor (TCR) fusion protein (TFP) (e.g. that comprise a TCR subunit and a human or humanized antibody domain) as described above) and/or comprising both a gene encoding a PD-1-CD28 fusion protein of the invention and a gene encoding an engineered (second) polypeptide as described herein. The invention also provides a host cell comprising one or more nucleic acids and/or vectors as described in this paragraph.

Where the one or more PD1-CD28 fusion protein of the invention (e.g., SEQ ID NO:14 or SEQ ID NO:24, preferably SEQ ID NO:24) and the one or more engineered (second) polypeptide are to be co-expressed in the same cell from a single nucleic acid, the expression of the PD-1-CD28 fusion protein and the second polypeptide can be driven independently by identical or different promoters. Promoters can be arranged in a bidirectional fashion in divergent configurations coordinating the regulation of two or more transgenes (bidirectional promoter vectors as known in the art). Promoters can also be arranged in a unidirectional orientation (dual promoter vectors) independently coordinating the regulation of two or more transgenes as known in the art. Accordingly, the invention provides a nucleic acid comprising a first promoter operably linked to a sequence encoding a PD1-CD28 fusion protein of the invention and a second promoter operably linked to a second polypeptide, wherein the first and second promoters are the same or different. Alternatively, the PD-1-CD28 fusion protein and second polypeptide that is co-expressed can be under the control of a single (i.e., the same) promoter. The different proteins may be engineered to be expressed under the control of the same promoter using any method known in the art or disclosed herein. For example, as is well known in the art, the gene encoding the first protein (e.g., a PD1-CD28 fusion protein of the invention (e.g., SEQ ID NO:14 or SEQ ID NO:24, preferably SEQ ID NO:24)) may be ligated to a sequence encoding a 2A peptide or 2A-like sequences (e.g., Szymczak et al., Nature Biotechnol. 22(2004), 589-594; Provost et al, Genesis 45(2007), 625-629; Diao and White, Genetics 190(2012), 1139-1144, each of which is incorporated by reference herein in its entirety) followed by the second polypeptide. Alternatively, the fusion protein of the invention and second polypeptide coding sequences can be linked by an IRES (internal ribosomal entry site).

The nucleic acids as provided herein (including vectors comprising such nucleic acids) can be introduced into target cells by any method known in the art. Such methods include, but are not limited to, cationic lipid method or liposome method, electroporation or calcium phosphate method. As used herein the cells into which the nucleic acids and/or vectors are introduced are also referenced as "transduced cells".

The co-expression of the PD1-CD28 fusion protein and the second polypeptide can be independently constitutive or constitutional, depending on the system used. The PD-1-CD28 fusion protein and the second polypeptide can be expressed on the surface of the herein provided transduced cell or may be otherwise detectable within or on the cell according to standard methods known in the art. The transduced cell for co-expression of a PD1-CD28 of the present invention and a second polypeptide may be, e.g., a CD4+-T cell, a CD8+-T cell, a γδ T cell, a natural killer (NK) T cell, a natural killer (NK) cell, a tumor-infiltrating lymphocyte (TIL) cell, a myeloid cell, or a mesenchymal stem cell. Preferably, the herein provided transduced cell for co-expression is a T cell (e.g. an autologous T cell), more preferably, the transduced cell is a CD8+ T cell or a CD4+ T cell. Accordingly, the transduced cell can be a CD8+ T cell that co-expresses both a PD1-CD28 fusion protein of the invention (e.g., SEQ ID NO:14 or SEQ ID NO:24, preferably SEQ ID NO:24) and a second polypeptide (e.g., a chimeric antigen receptor, an alpha/beta T cell receptor, a natural T cell receptor, an anti-CD3 T cell engagers expressed as soluble polypeptide or presented as transmembrane protein on the cell surface, and/or a T-cell Receptor (TCR) fusion protein (TFP) (e.g. that comprise a TCR subunit and a human or humanized antibody domain) as described above). Further, the transduced cell for co-expression can be an autologous T cell or an allogenic T cell as described herein. Alternately or additionally, the transduced cell can be a CD4+ T cell that co-expresses both a PD1-CD28 fusion protein of the invention (e.g., SEQ ID NO:14 or SEQ ID NO:24, preferably SEQ ID NO:24) and a second polypeptide (e.g., a chimeric antigen receptor, an alpha/beta T cell receptor, a natural T cell receptor, an anti-CD3 T cell engagers expressed as soluble polypeptide or presented as transmembrane protein on the cell surface, and/or a T-cell Receptor (TCR) fusion protein (TFP) (e.g. that comprise a TCR subunit and a human or humanized antibody domain) as described above). The transduced CD4+ T cell can be an autologous CD4+ T cell or an allogeneic CD4+ T cell. Alternately or additionally, the invention provides populations of transduced CD4+ T cells and/or CD8+ T cells (including but not limited to populations comprising transduced CD4+ T cells, populations comprising transduced CD8+ T cells, and populations comprising both transduced CD4+ T cells and transduced CD8+ T cells), wherein each of the transduced cells expresses a PD1-CD28 fusion protein of the invention, an engineered (second) polypeptide as described above, or expresses both a PD1-CD28 fusion protein of the invention and an engineered (second) polypeptide as described above. The population of co-expressing transduced CD4+ and/or CD8+ T cells may be autologous and/or allogenic (e.g., the population may comprise only autologous cells, only allogenic cells, or combinations of both autologous and allogenic cells). The co-expressing populations of T cells of the invention as described herein may comprise both transduced and non-transduced T cells, such that the population as a whole expresses or a representative sample of the population expresses both a PD1-CD28 fusion protein of the invention and an engineered (second) polypeptide as described above.

As described herein, the present invention relates to a kit comprising the nucleic acid molecule of the invention, the vector of the invention and/or the fusion protein of the invention. Thus, the herein provided treatment methods may be realized by using this kit. Advantageously, the kit of the present invention further comprises optionally (a) reaction buffer(s), storage solutions (i.e. preservatives), wash solutions and/or remaining reagents or materials required for the conduction of the assays as described herein. Furthermore, parts of the kit of the invention can be packaged individually in vials or bottles or in combination in containers or multi-container units. In addition, the kit may contain instructions for use. The manufacture of the kit of the present invention follows preferably standard procedures which are known to the person skilled in the art. As mentioned above, the kit provided herein is useful for treating a subject (preferably a human patient) which has a disease which is characterized by expressing a ligand for PD-1 (i.e. PD-L1 and/or PD-L2) such as, e.g., lung cancer, ovarian cancer, melanoma, colon cancer, gastric cancer, renal cell carcinoma, esophageal carcinoma, glioma, urothelial cancer, retinoblastoma, breast cancer, Non-Hodgkin lymphoma, pancreatic carcinoma, Hodgkin's lymphoma, myeloma, hepatocellular carcinoma, leukemia, cervical carcinoma, cholangiocarcinoma, oral cancer, head and neck cancer, or mesothelioma.

THE FIGURES SHOW

Figure 1:
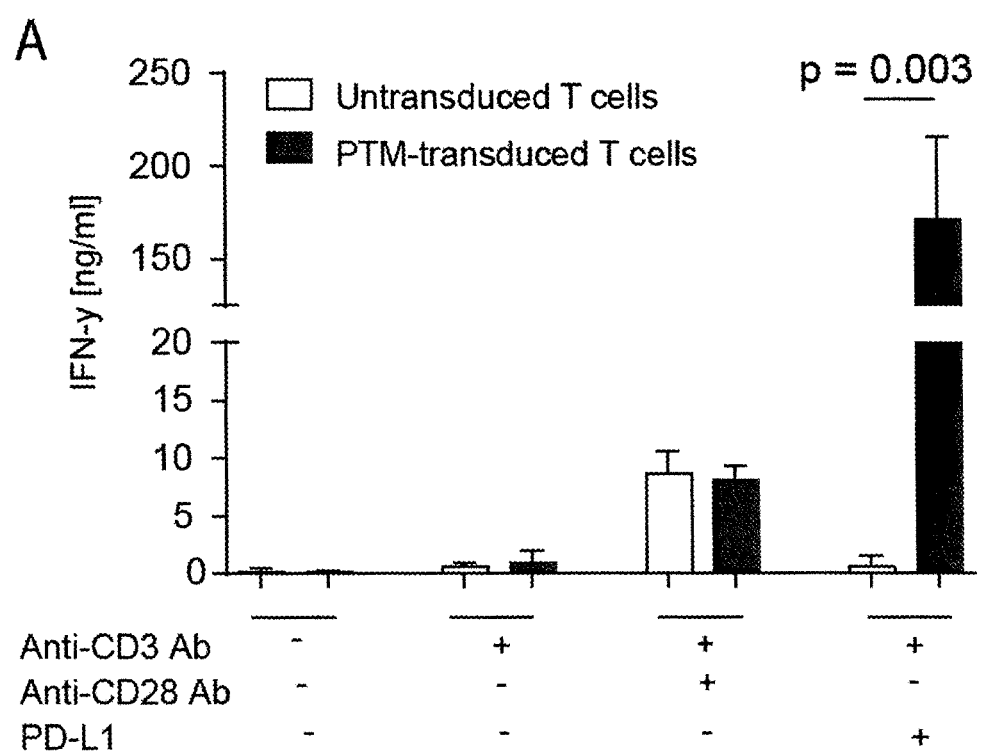
Figure 1:
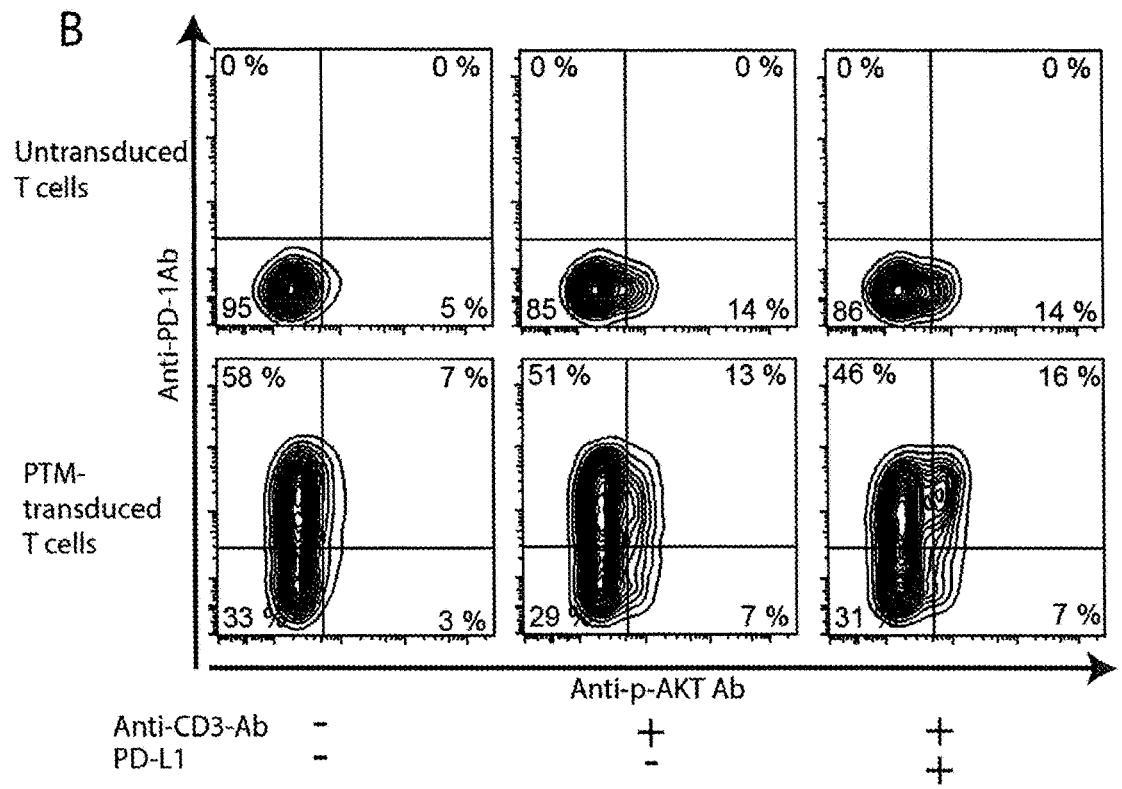
Figure 1:
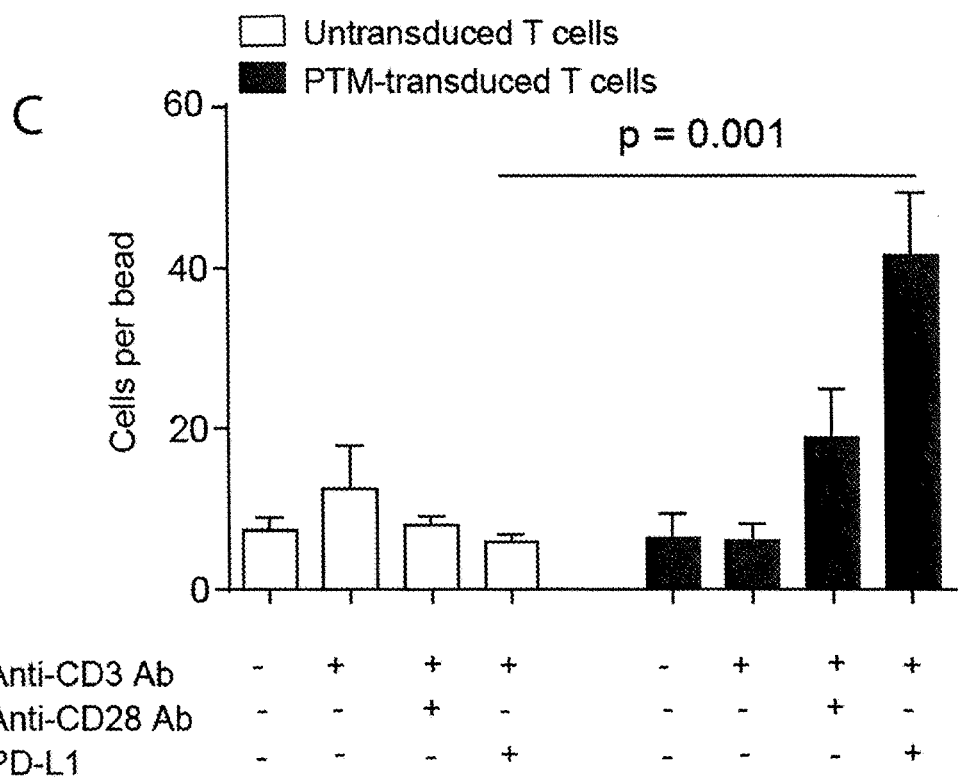
Figure 1:
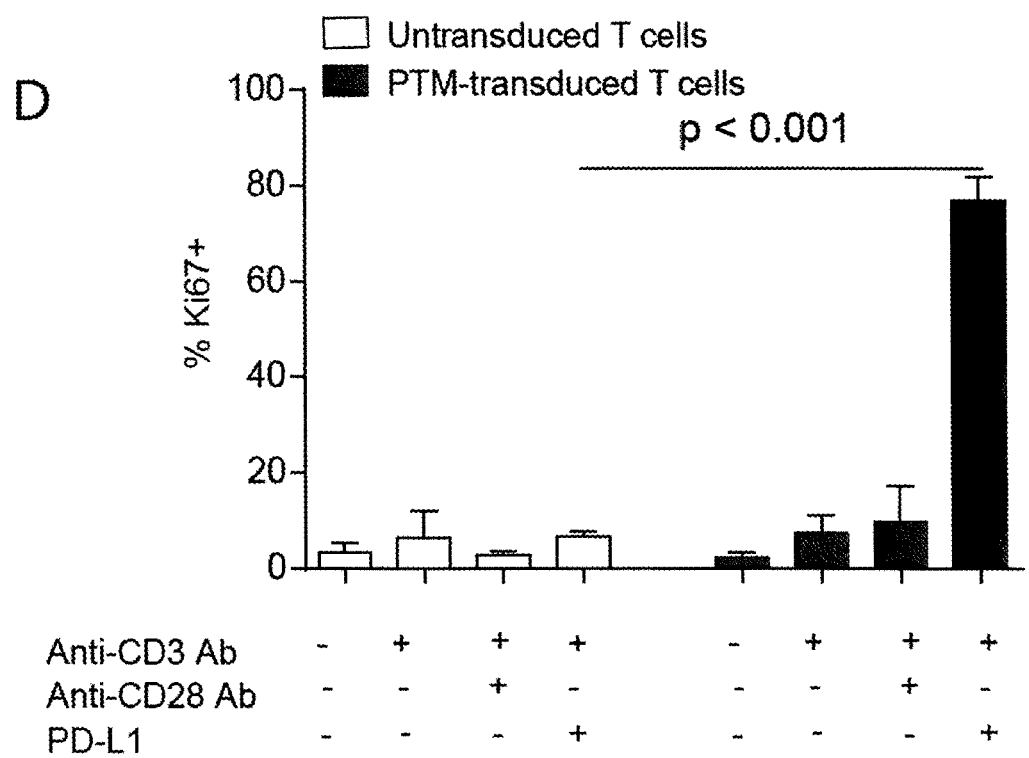
Figure 1:
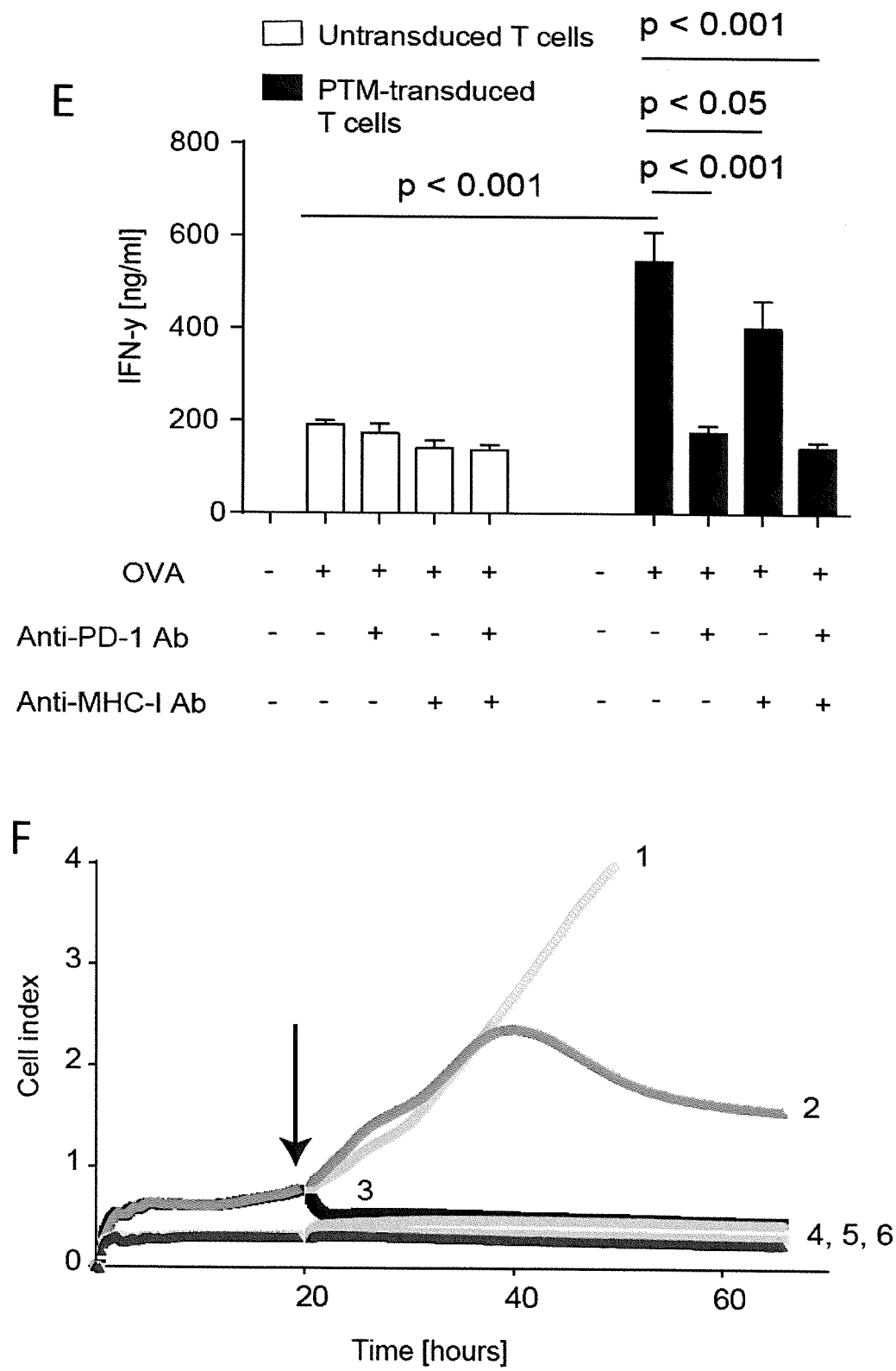

FIG. 1: In vitro characterization of the PD-1-CD28 fusion protein (PD-1 transmembrane domain, PTM fusion protein (SEQ ID NOs: 13 (nucleic acid (cDNA)) and 14 (protein))

(A) PTM fusion protein (as depicted in SEQ ID NOs: 13 (nucleic acid (cDNA)); 14 (protein))-transduced or untransduced primary murine/mouse T cells were either stimulated with anti-CD3 antibody, anti-CD3 plus anti-CD28 antibodies or with anti-CD3 antibody plus recombinant PD-L1 (SEQ ID NOs: 37 (nucleic acid (cDNA)); 38 (protein)) and resulting IFN-γ release was measured by ELISA. (B) PTM fusion protein-transduced or untransduced primary murine T cells were either left unstimulated or stimulated with anti-CD3 antibody or with anti-CD3 antibody plus recombinant PD-L1 and phosphorylation of AKT was measured by flow cytometry. (C) PTM-fusion protein-transduced or untransduced primary murine T cells were either stimulated with anti-CD3 antibody, anti-CD3 plus anti-CD28 antibodies or with anti-CD3 antibody plus recombinant PD-L1 (SEQ ID NOs: 37 (nucleic acid); 38 (protein)) and cell numbers were normalized to standardized counting beads. (D) PTM-fusion protein (SEQ ID NOs: 13 (nucleic acid (cDNA)); 14 (protein)) or untransduced primary murine T cells were either stimulated with anti-CD3 antibody, anti-CD3 plus anti-CD28 antibodies or with anti-CD3 antibody plus recombinant PD-L1 (SEQ ID NOs: (SEQ ID NOs: 37 (nucleic acid (cDNA)); 38 (protein)) for 24 h and stained intracellularly for the mitosis marker ki67. (E) PTM-fusion protein (SEQ ID NOs: 13 (nucleic acid); 14 (protein)) or untransduced OT-1 T cells were cocultured with Panc02-OVA-PD-L1 in the presence or absence of anti-PD-1 antibody or anti-mouse H2kb SIINFEKL antibody and resulting IFN-γ production was measured by ELISA. (F) PTM-fusion protein (SEQ ID NOs: 13 (nucleic acid (cDNA)); 14 (protein)) or untransduced OT-1 T cells were prestimulated with anti-CD3 antibody and with recombinant PD-L1. In the meantime, Panc02-OVA-PD-L1 cells were seeded and grown prior to the addition of prestimulated T cells (arrow). The conditions are as follows Panc02-OVA-PD-L1 only (1), Panc02-OVA-PD-L1+prestimulated untransduced T cells (2), Panc02-OVA-PD-L1+prestimulated PTM-fusion protein transduced T cells (3), PTM-fusion protein (4) and untransduced T cells (5) and medium (6). Panc02-OVA cell viability was measured by impedance-based measurement. Experiments A to E are representative of at least three independent experiments each performed in triplicates. Experiment F is representative of three independent experiments performed in duplicates for technical reasons. Bars represent SD and p-values from Student's t-test are shown. All tests are two-sided.

FIG. 2: Functional comparison of different PD-1-CD28 fusion proteins (A) Schematic overview of the structure of the different PD-1-CD28 fusion proteins: PTM (SEQ ID NOs: 13 (nucleic acid (cDNA)); 14 (protein)): PD-1 extracellular domain (PD-1-ex) and transmembrane domain (PD-1-trans) (as depicted in SEQ ID NOs: 5 (nucleic acid); 6 (protein)) fused to the CD28 intracellular domain (CD28-intra; SEQ ID NOs: 11 (nucleic acid (cDNA)); 12 (protein)). CTM (SEQ ID NOs: 43 (nucleic acid (cDNA)); 44 (protein)): PD-1 extracellular domain (SEQ ID NOs: 39 (nucleic acid (cDNA)); 40 (protein)) fused to CD28 transmembrane (CD28-trans) and intracellular domain (SEQ ID NOs: 41 (nucleic acid); 42 (protein)); and CEX (SEQ ID NOs: 49 (nucleic acid (cDNA)); 50 (protein)): PD-1 extracellular domain (SEQ ID NOs: 45 (nucleic acid (cDNA)); 46 (protein)) fused to CD28 extracellular segment (CD28-ex) and CD28 transmembrane and intracellular domain (SEQ ID NOs: 47 (nucleic acid (cDNA)); 48 (protein)). (B) PTM- (SEQ ID NOs: 49, 50), CTM- (SEQ ID NOs: 43, 44), CEX (SEQ ID NOs: 49, 50)- or untransduced primary murine T cells were stimulated with anti-CD3 antibody, anti-CD3 plus anti-CD28 antibodies or anti-CD3 antibody plus recombinant PD-L1 (SEQ ID NOs: 37 (nucleic acid); 38 (protein)) and IFN-γ production was measured by ELISA. (C) PTM-, CTM-, CEX-fusion protein-transduced or untransduced primary murine T cells were stimulated with anti-CD3 antibody, anti-CD3 plus anti-CD28 antibodies or anti-CD3 antibody plus recombinant PD-L1 37 (nucleic acid); 38 (protein)) and resulting cell numbers were normalized to counting beads. (D) PTM-, CTM-, CEX-fusion protein-transduced or untransduced T cells were incubated with recombinant PD-L1 37 (nucleic acid); 38 (protein)) and PD-L1 binding was measured by flow cytometry. (E) Representative costaining for CD8 and PD-1 expression of PTM-, CTM-, CEX- or untransduced T cells. All experiments are representative of at least three independent experiments each performed in triplicates. Bars represent SD and p-values from Student's t-test are shown. All tests are two-sided.

FIG. 3: Functional comparison of different mutated PTM fusion proteins in their putative signaling domains.

(A) Schematic overview of the different PTM-fusion protein mutants: PTM (YMNM-PYAP, wild type (SEQ ID NOs: 13 (nucleic acid (cDNA)); 14 (protein)), PTM-FMNM (tyrosine-mutated, Y to F (SEQ ID NOs: 51 (nucleic acid (cDNA)); 52 (protein)), PTM-AYAA (proline-mutated, P to A (SEQ ID NOs: 53 (nucleic acid (cDNA)); 54 (protein)) and PTM-FMNM-AYAA (proline- and tyrosine-mutated (SEQ ID NOs: 55 (nucleic acid (cDNA)); 56 (protein)). (B) PTM (SEQ ID NOs: 13, 14), PTM-tyrosine-mutated (PTM-FMNM; SEQ ID NOs: 51, 52)), PTM-proline-mutated (PTM-AYAA; SEQ ID NOs: 53, 54)) and PTM-tyrosine- and proline-mutated (PTM-FMNM-AYAA; SEQ ID NOs: 55, 56) or untransduced T cells were stimulated with anti-CD3 antibody or with anti-CD3 antibody plus recombinant PD-L1 (SEQ ID NOs: 37 (nucleic acid (cDNA)); 38 (protein)) and IFN-γ production was measured by ELISA. (C) Untransduced, PTM-, PTM-FMNM-, PTM-AYAA- or PTM-FMNM-AYAA-transduced T cells were stimulated with anti-CD3 antibody or anti-CD3 antibody plus recombinant PD-L1 and the amount of viable cells was quantified by normalization to counting beads. (D) Untransduced, PTM (SEQ ID NOs: 13 (nucleic acid); 14 (protein))-, PTM-FMNM (SEQ ID NOs: 51 (nucleic acid (cDNA)); 52 (protein))-, PTM-AYAA (SEQ ID NOs: 53 (nucleic acid (cDNA)); 54 (protein))- or PTM-FMNM-AYAA (SEQ ID NOs: 55 (nucleic acid (cDNA)); 56 (protein))-transduced T cells were stimulated with anti-CD3 antibody plus recombinant PD-L1 (SEQ ID NOs: 37 (nucleic acid (cDNA)); 38 (protein)) and cytokine release was analyzed semiquantitatively using a murine cytokine array. The array screens for expression for a broad panel of 40 cytokines. P-values below 0.05 are marked with * in FIG. 3D. Experiments B and C are representative of at least three independent experiments performed in triplicates. Experiment C was performed three times in duplicates for technical reasons. Bars represent SD and p-values from Student's t-test are shown. All tests are two-sided.

Figure 4:
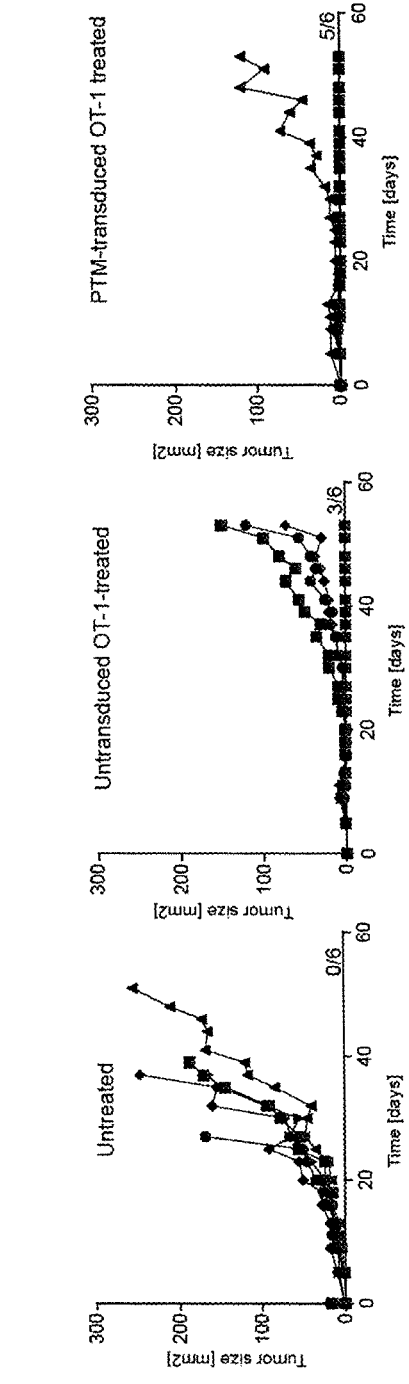
Figure 4:
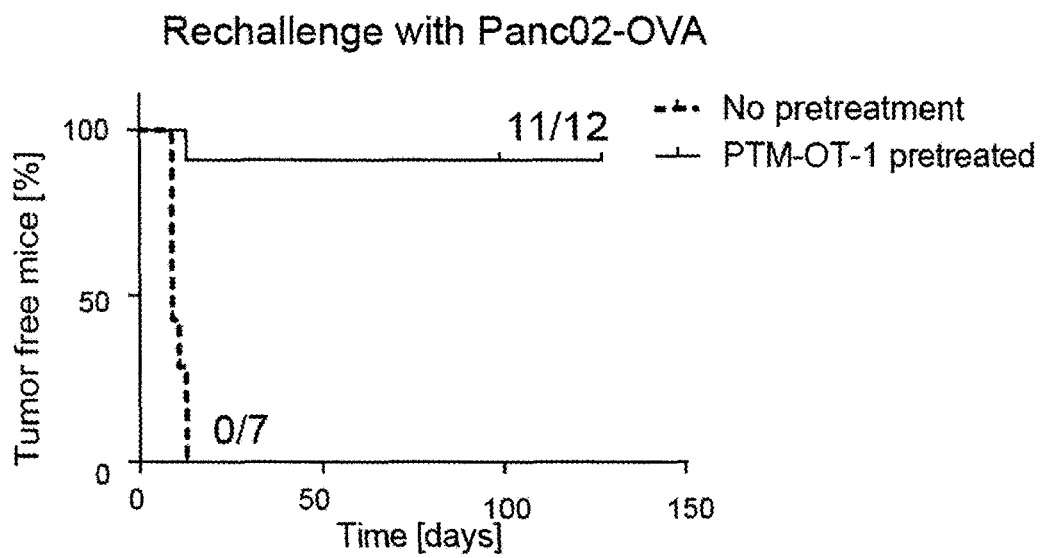
Figure 4:
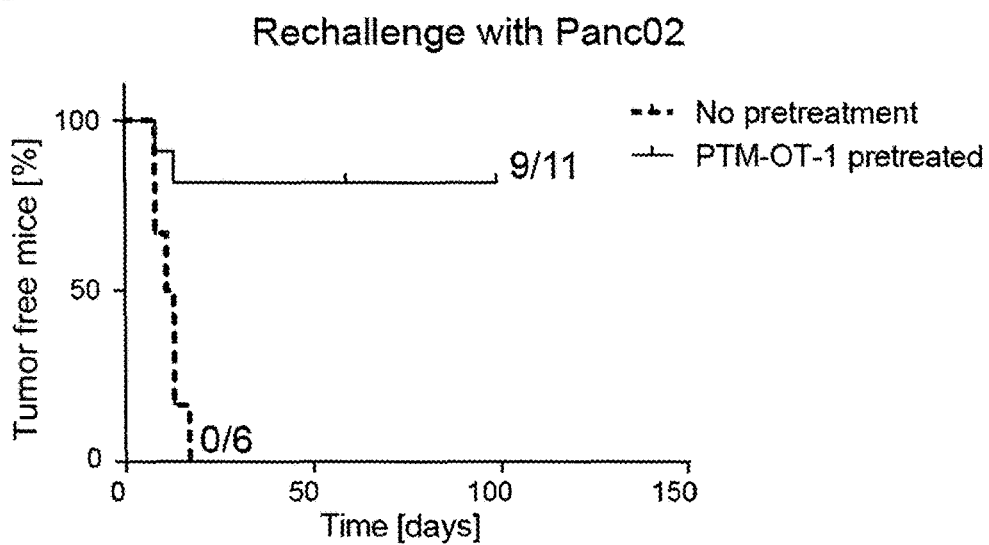
Figure 4:
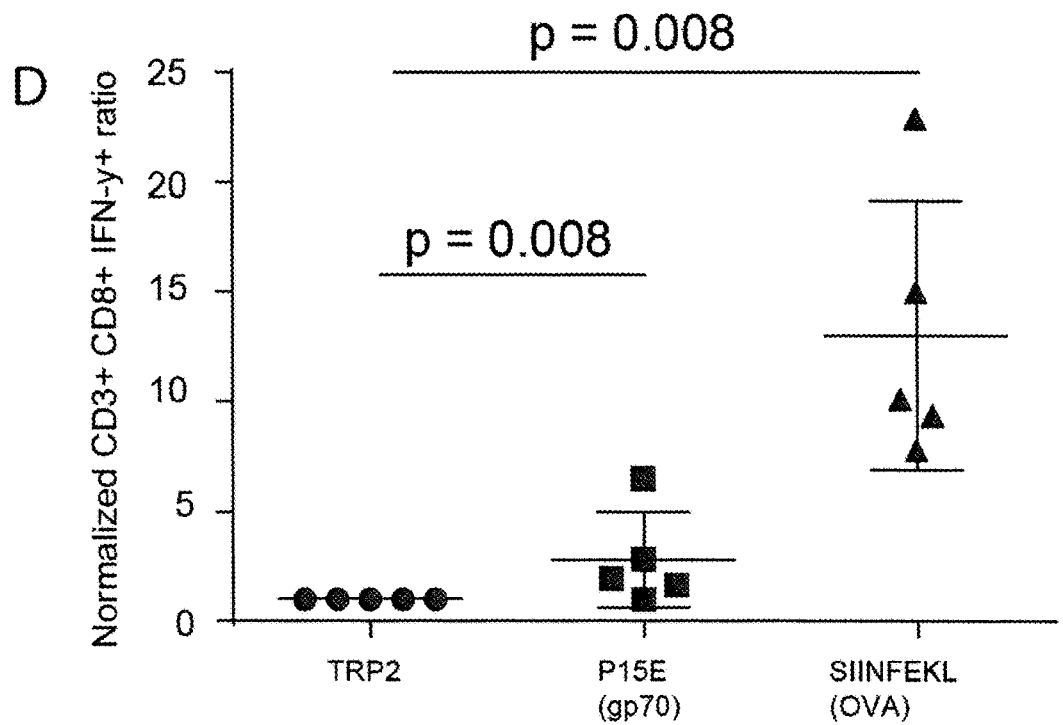
Figure 4:
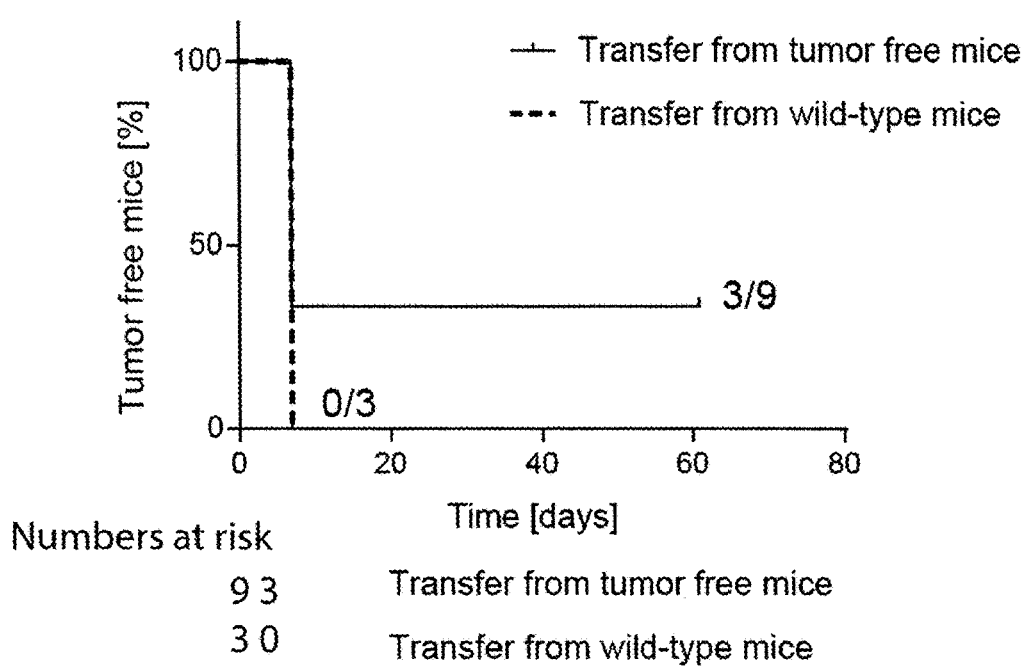

FIG. 4: Therapeutic efficacy of PTM fusion protein-transduced OT-1 T cells in vivo and induction of immunological memory (A) 18 mice were injected subcutaneously with Panc02-OVA cells. Once the tumors were established, 6 mice each were randomized either to no treatment, to adoptive transfer of untransduced OT-1 T cells or to adoptive transfer of PTM-protein-transduced OT-1 T cells. Tumor size was measured in a blinded fashion every other day. The experiment is representative of three independent experiments with 6 mice per group. (B) Surviving mice (n=12) from two independent experiments were rechallenged with Panc02-OVA cells at the same time as tumor-naïve wild type mice (n=7). (C) Surviving mice after first rechallenge (n=11, from experiment depicted in panel B) and tumor-naïve wild type mice (n=6) were rechallenged with a sublethal dose of Panc02 cells. (D) Lymph nodes from surviving mice from Panc02-rechallenge (experiment depicted in panel C) were stimulated in organ culture in vitro with either control peptide TRP2, P15E peptide or SIINFEKL (SEQ ID NO: 65, referring to the amino acids (AA) 258-265 of the chicken ovalbumin (Uni Prot Entry: P01012 (version 147 of the entry and version 2 of the sequence))) peptide. The number of IFN-γ-producing CD8+-T cells was analyzed by flow cytometry and was normalized to the number of IFN-γ-producing CD8+-T cells after TRP2 stimulation for each mice. (E) Splenocytes from mice having cleared Panc02-OVA tumors after transfer of PTM-fusion protein transduced OT-1 T cells or from wild-type mice were adoptively transferred on wild type mice. These mice were challenged with Panc02-OVA cells. Transfer of splenocytes from tumor-free mice prevented tumor outgrowth in 3 of 9 mice. Survival analysis was performed using the log-rank test. For comparison of experimental conditions of individual mice, the Mann-Whitney test was used. All tests are two-sided.

Figure 5:
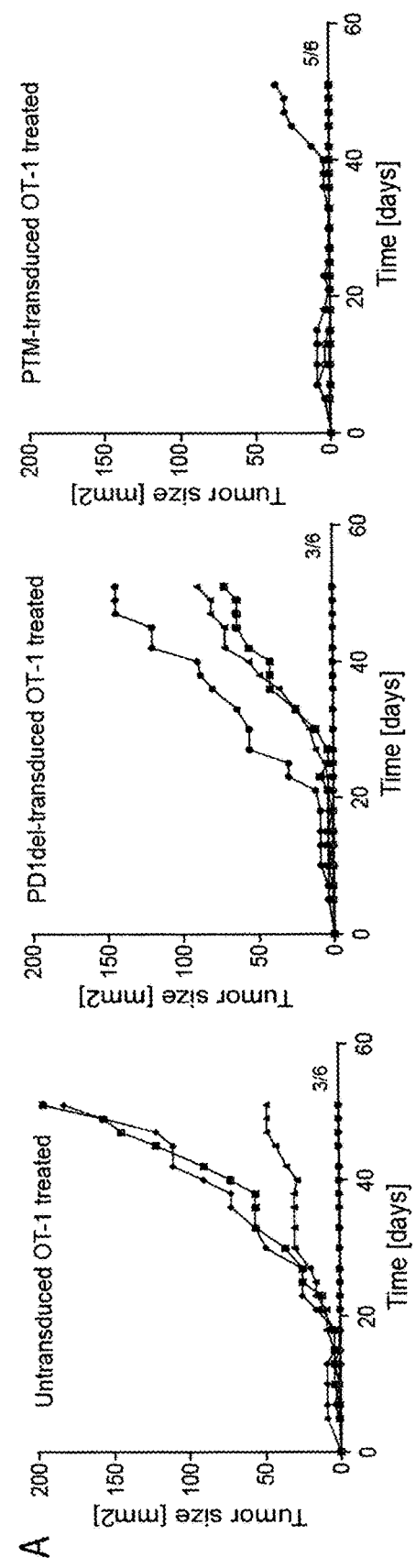
Figure 5:
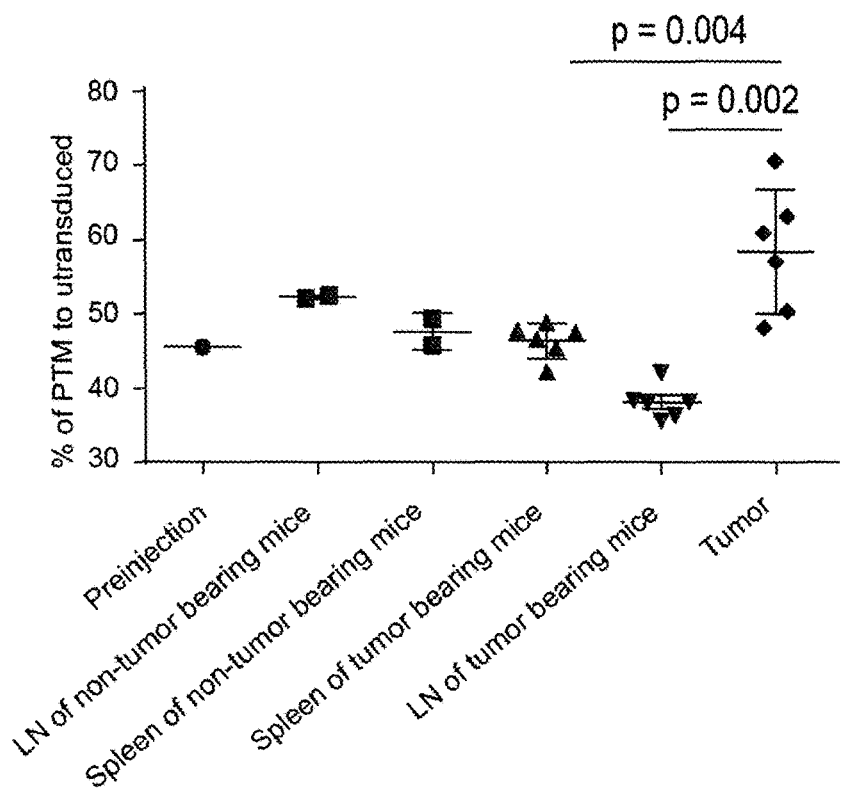
Figure 5:
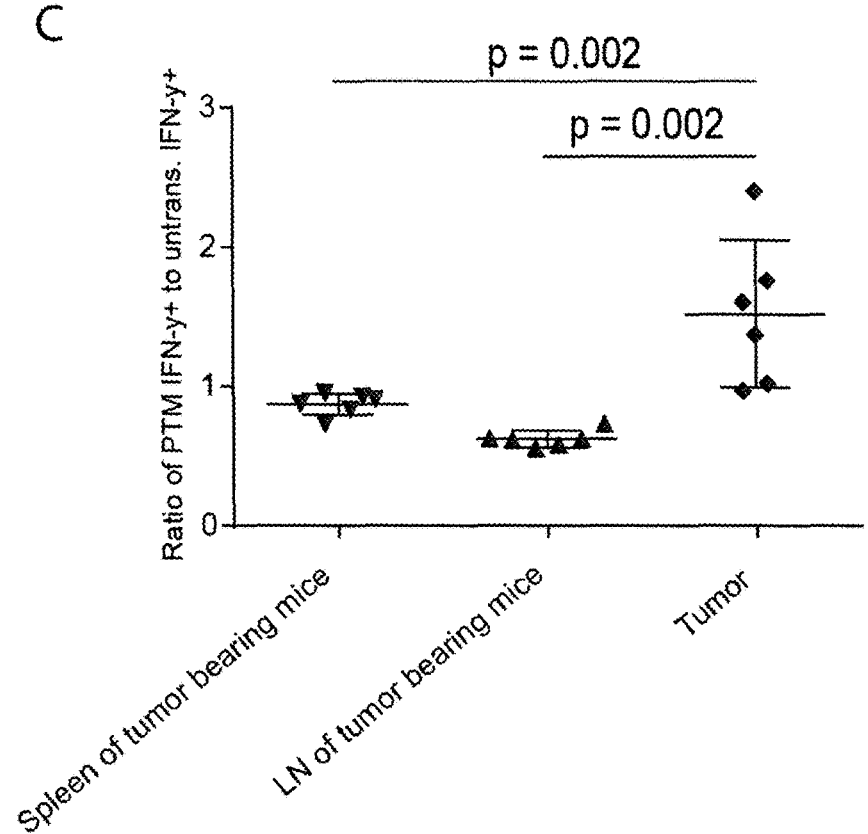
Figure 5:
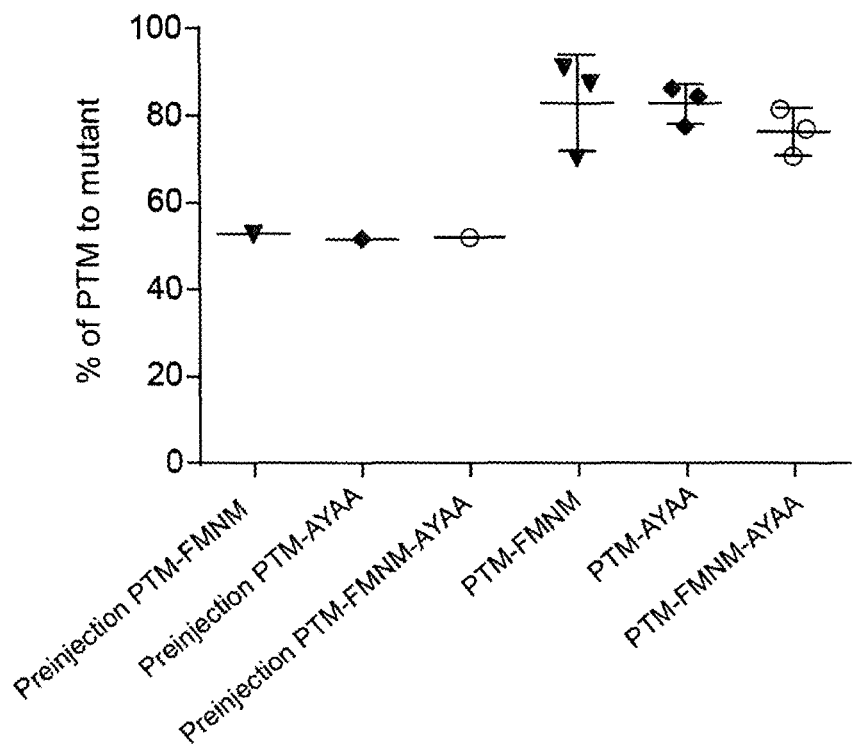

FIG. 5: In vivo mode of action of PTM fusion protein-transduced OT-1 T cells (A) 18 mice were subcutaneously injected with Panc02-OVA cells. Once the tumors were established, the mice were randomized to adoptive transfer of either untransduced OT-1 T cells or of T cells transduced with a deleted PD-1 receptor (SEQ ID NOs: 57 (nucleic acid (cDNA)); 58 (protein)) or with unmodified PTM fusion protein (SEQ ID NOs: 13 (nucleic acid (cDNA)); 14 (protein)). Tumor size was measured every other day in a blinded fashion. The experiment is representative of three independent experiments with 6 mice per group. (B) T cells from CD45.1-OT-1 mice were transduced with PTM-fusion protein and T cells from CD90.1-OT-1 mice were left untransduced. T cells were co-injected in equal amounts in wild type mice (n=2) or in mice bearing Panc02-OVA tumors (n=6). Four days later, T cells were analyzed in the different compartments and the ratio of PTM-fusion protein (SEQ ID NOs: 13 (nucleic acid); 14 (protein)) transduced to untransduced OT-1-T cells was compared. The experiment is representative of three independent experiments with 6 mice per tumor-bearing group. (C) Untransduced CD90.1-OT-1-T cells and PTM-fusion protein (SEQ ID NOs: 13 (nucleic acid); 14 (protein)) transduced CD45.1-OT-1 T cells were isolated from tumor, spleen and lymph nodes obtained in experiment (B) and were analyzed for IFN-γ expression by flow cytometry. The experiment is representative of three independent experiments with 6 mice per tumor-bearing group. (D) CD45.1 OT-1 T cells were transduced with PTM-fusion protein, CD90.1 OT-1-T cells were transduced with either of the mutant fusion proteins PTM-FMNM (SEQ ID NOs: 52 (protein), 51 (cDNA)), PTM-AYAA (SEQ ID NOs: 54 (protein), 53 (cDNA)) or PTM-FMNM-AYAA (SEQ ID NOs: 56 (protein), 55 (cDNA)) and were mixed in equal amounts with PTM-transduced CD45.1 OT-1 T cells prior to transfer to Panc02-OVA-tumor bearing mice (n=3 per group). Four days after transfer, the ratio of PTM-receptor transduced T cells to mutant fusion protein-transduced T cells was analyzed by flow cytometry. The experiment is representative of three independent experiments with 3 mice per tumor-bearing group. (E) PTM-fusion protein transduced or untransduced OT-1 T cells were adoptively transferred in Panc02-OVA tumor bearing mice (n=17, respectively). One week later the number of tumor infiltrating MDSC (CD45$^+$, CD11b$^+$, Ly6$^+$, Gr-1 intermediate$^+$) was analyzed. Data represent results of pooled mice from three independent experiments. Bars represent SD. Survival analysis was performed using the log-rank test. For comparison of experimental conditions of individual mice, the Mann-Whitney test was used. All tests are two-sided.

Figure 6:
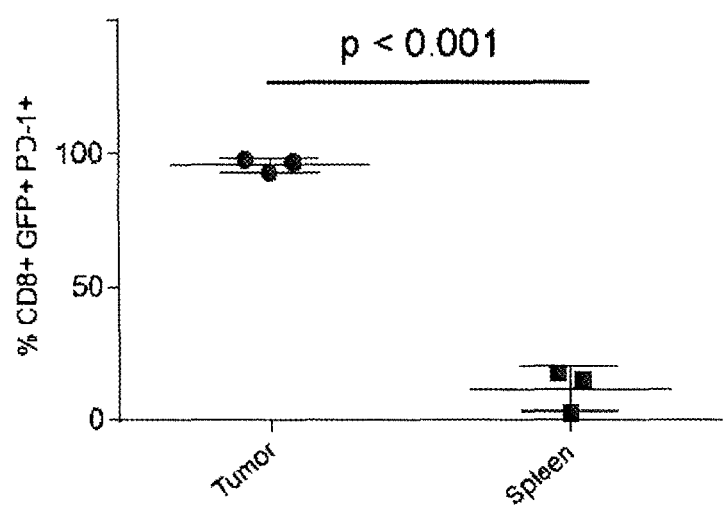
Figure 6:
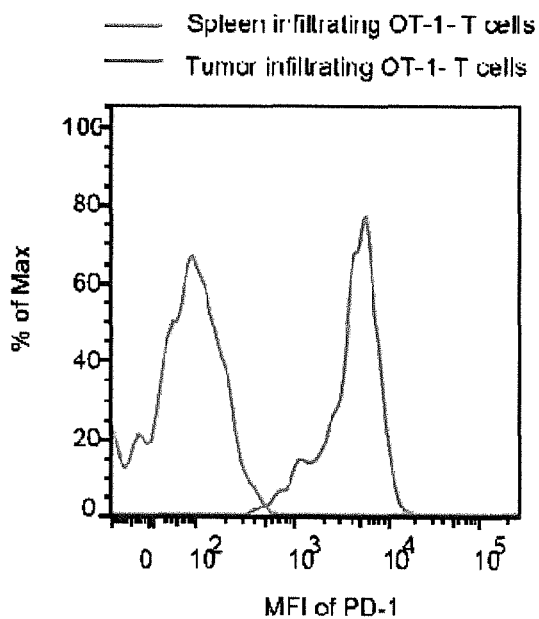
Figure 6:
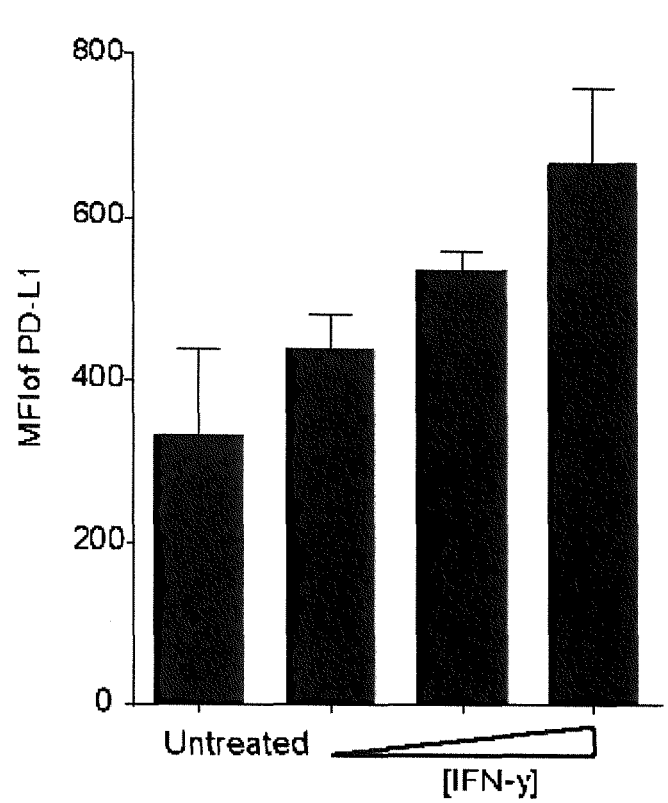
Figure 6:
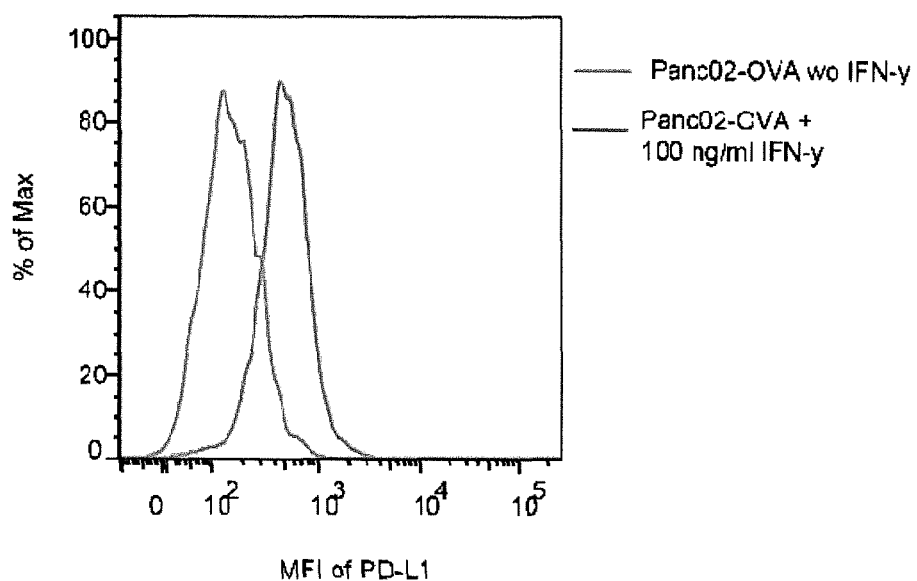
Figure 6:
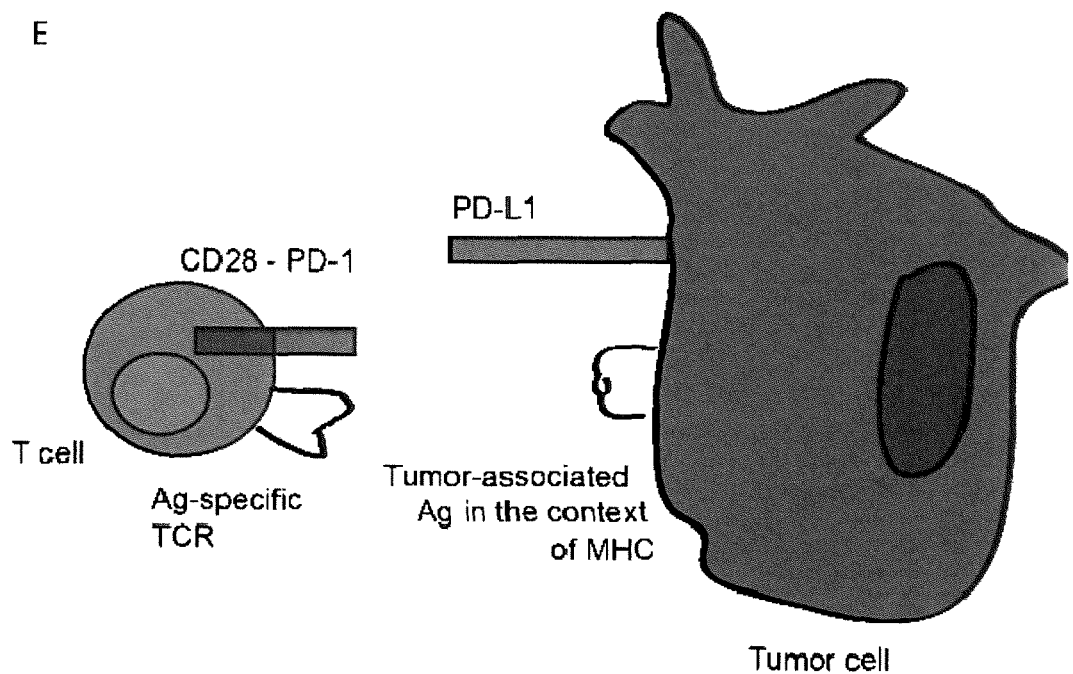
Figure 6:
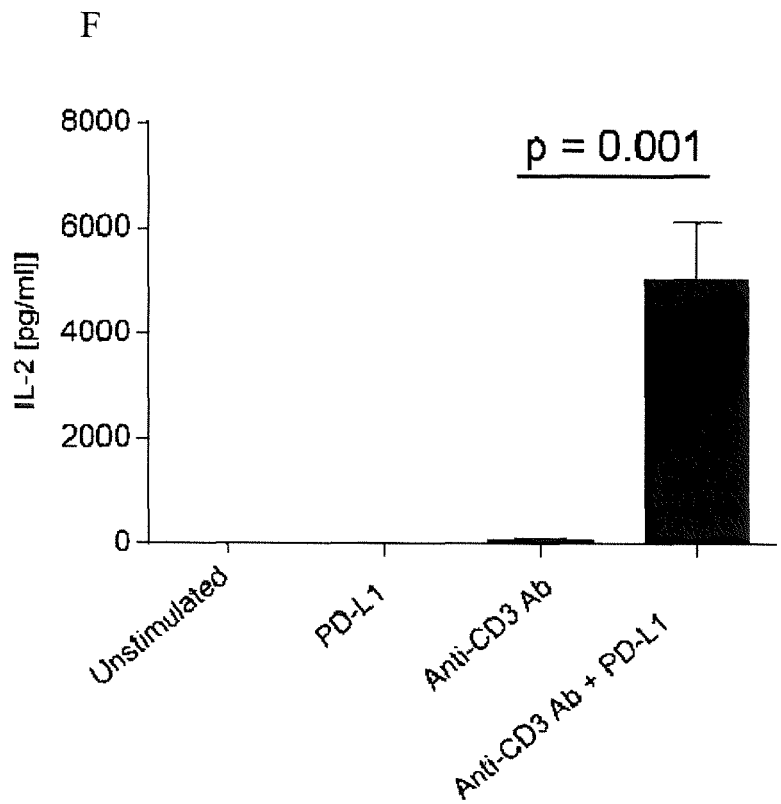

FIG. 6: Rationale for the use of a PD1-CD28-fusion protein (PTM; SEQ ID NOs: 13 (cDNA), 14 (protein): PD1-upregulation by intratumoral T cells and PD-L1 expression on the tumor cell (A) GFP-transduced OT-1 T cells were adoptively transferred into Panc02-OVA tumor bearing mice. One week later, infiltration of the tumor as well as the spleen by GFP+ OT-1 T cells and PD-1 expression of infiltrating T cells was analyzed by flow cytometry. Almost all tumor infiltrating OT-1 T cells were positive for PD-1 in contrast to OT-1 T cells in the spleen. (B) Exemplary histograms of PD-1 expression on tumor-infiltrating OT-1-T cells (dark grey) and spleen infiltrating OT-1-T cells (light grey). (C) Panc02-OVA cells were stimulated in vitro with IFN-γ (2, 20 and 100 ng/ml) and expression of PD-L1 was analyzed by flow cytometry 48 h later. IFN-γ upregulated PD-L1 expression dose dependently. (D) Exemplary histograms of PD-L1 expression on Panc02-OVA tumor cells after stimulation with 100 ng/ml IFN-γ (dark grey) and without stimulation (light grey). (E) Schematic overview of the mechanism of action: the fusion protein of the PD-1 extracellular and transmembrane domain with the CD28 intracellular domain protects antigen-specific T cells from PD-1-PD-L1-mediated anergy and to turn the inhibitory signal into a costimulation. (F) PTM fusion protein (SEQ ID NOs: 13 (nucleic acid (cDNA)); 14 (protein))-transduced T cells were stimulated either with anti-CD3 antibody, recombinant PD-L1 (SEQ ID NOs: 37 (cDNA), 38 (protein)) or both. IL-2 induction was analyzed 48 h later by ELISA. Combined stimulation with both compounds lead to a strong induction of IL-2.

Figure 7:
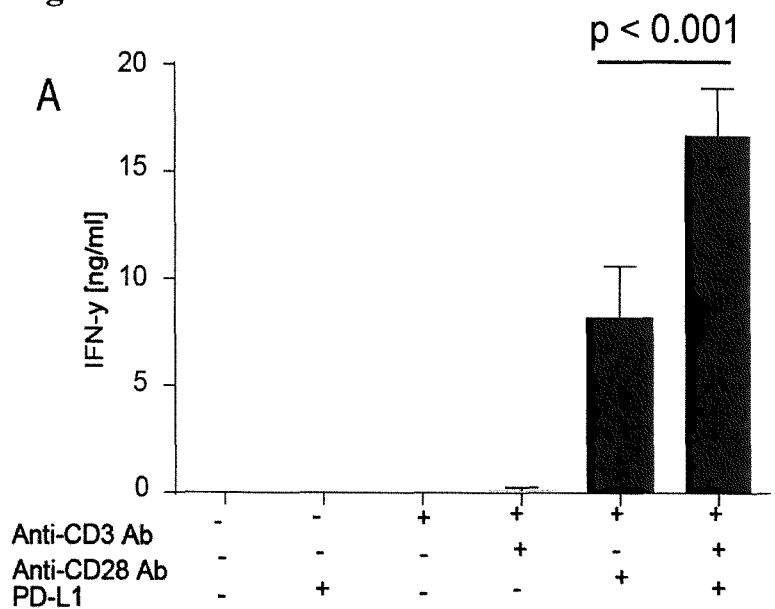
Figure 7:
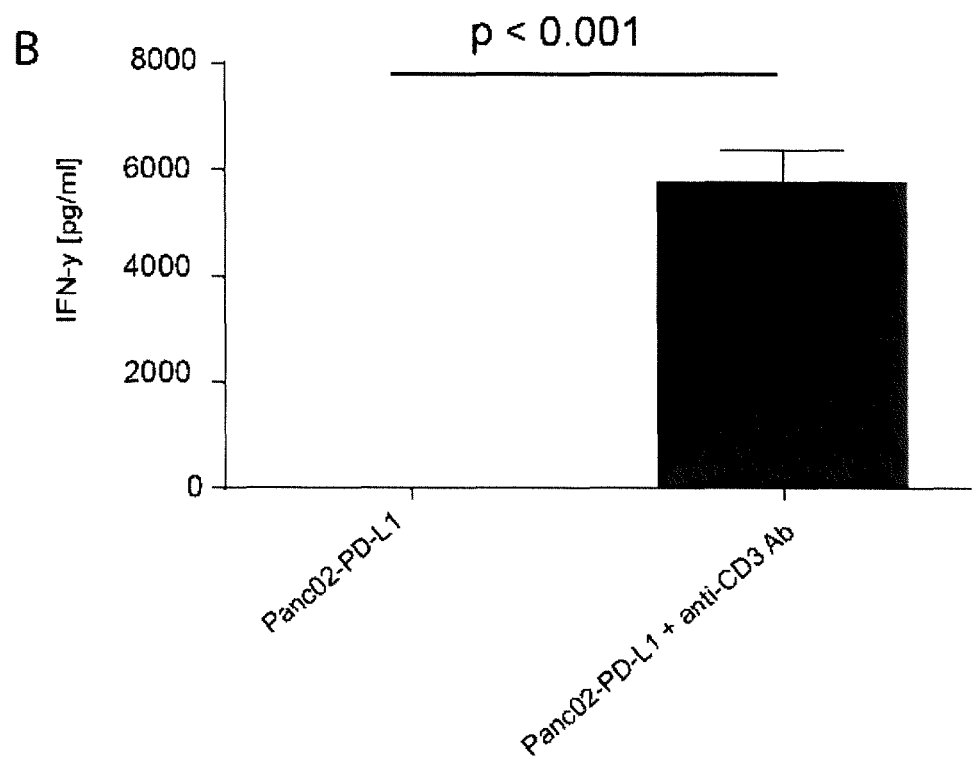
Figure 7:
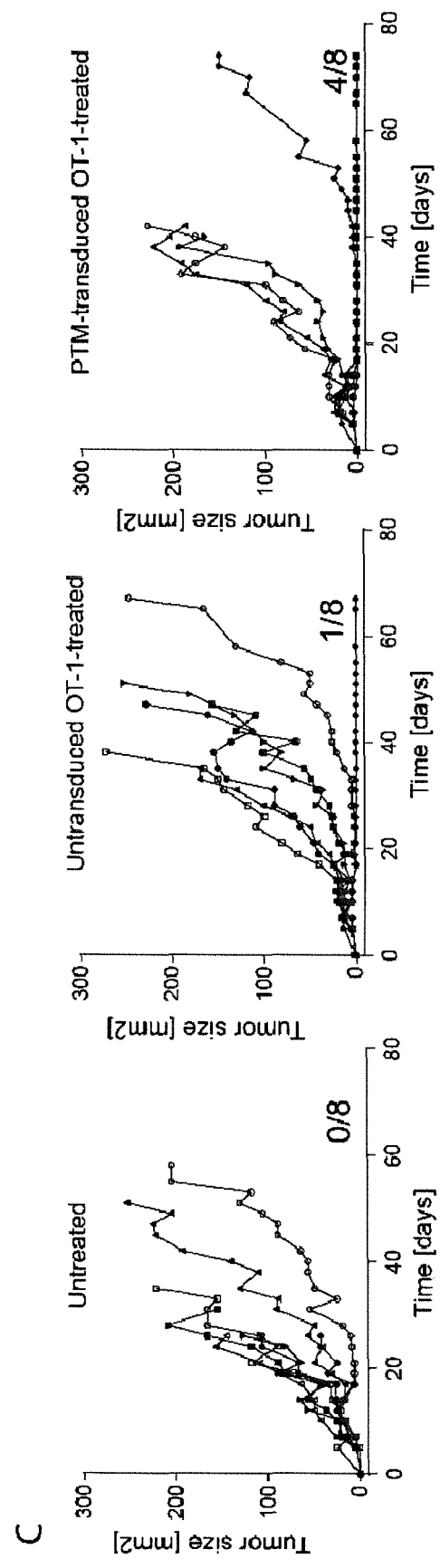
Figure 7:
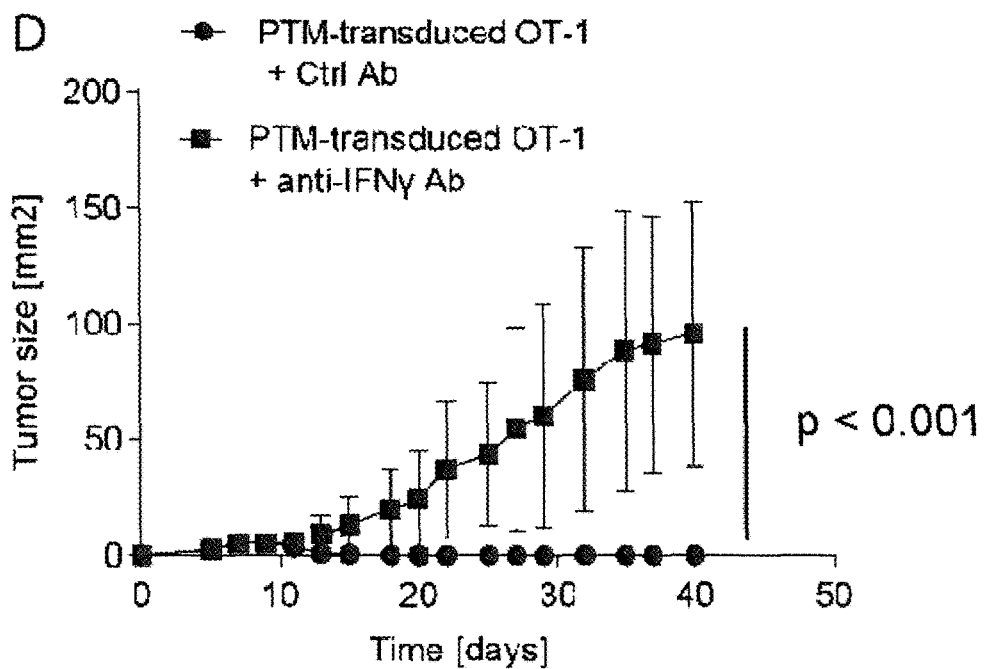
Figure 7:
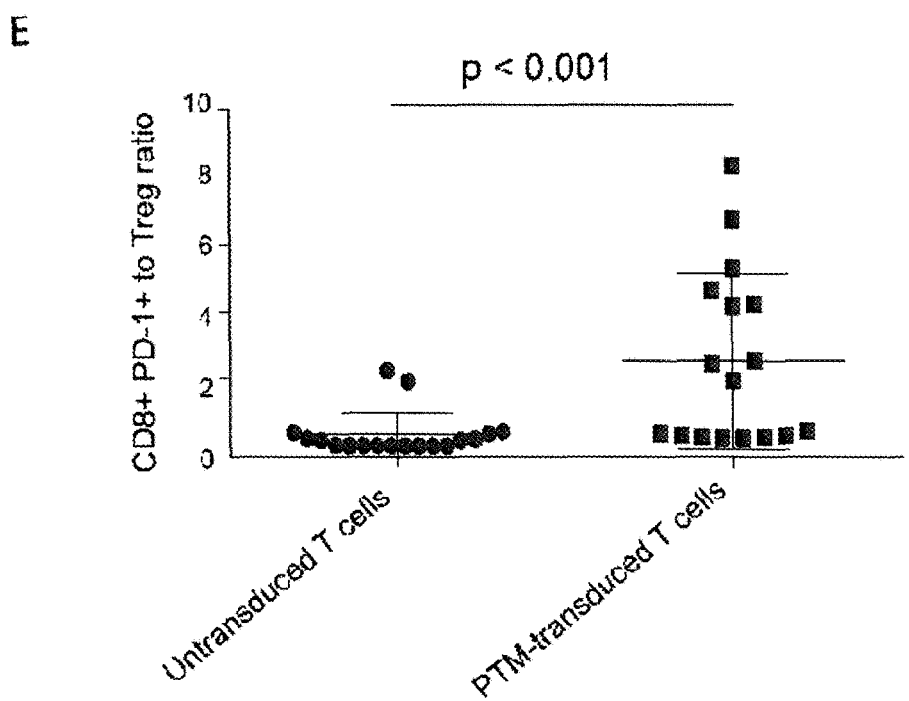

FIG. 7: Therapeutic efficacy of PD1-CD28 fusion protein (PTM; SEQ ID NOs: 13 (cDNA), 14 (protein))-transduced T cells in the Panc02-OVA model overexpressing PD-L1 and dependency of the treatment effect upon IFN-γ

(A) PTM fusion protein (SEQ ID NOs: 13 (nucleic acid); 14 (protein))-transduced T cells were stimulated either with anti-CD3 antibody, anti-CD28 antibody, recombinant PD-L1 (SEQ ID NOs: 37 (nucleic acid); 38 (protein)), anti-CD3 antibody and recombinant PD-L1 or all three stimuli. IFN-γ induction was analyzed 48 h later by ELISA. Combined stimulation with all compounds lead to a strong induction of IFN-γ. (B) PTM fusion protein (SEQ ID NOs: 13 (cDNA), 14 (protein))-transduced OT-1 T cells were cocultured with Panc02-PD-L1 in the presence or absence of anti-CD3 antibody (1 μg/ml) for 48 h and IFN-γ was quantified in the supernatant. (C) 24 mice were subcutaneously injected with Panc02-OVA-PD-L1 cells. Once the tumors were established, mice (n=8 per group) were randomized to either remain untreated or be treated twice with untransduced OT-1 T cells or PTM fusion protein (SEQ ID NOs: 13 (cDNA), 14 (protein))-transduced OT-1 T cells. Tumor size was measured every other day in a blinded fashion. PTM fusion protein-transduced OT-1 T cells significantly increased the number of tumor free mice compared to the two control groups. (D) 10 mice were subcutaneously injected with Panc02-OVA cells. Once the tumors were established, mice (n=5 per group) were randomized to be treated with PTM fusion protein-transduced OT-1 T cells together with 200 μg IFN-γ neutralizing antibody or isotype control. Antibodies were applied i.p. every three days for four doses from time point of randomization. Tumor size was measured every other day in a blinded fashion. IFN-γ neutralizing antibodies abrogated the therapeutic impact of PTM-transduced OT-1 T cells. (E) PTM fusion protein-transduced or untransduced OT-1 T cells were adoptively transferred into Panc02-OVA-tumor bearing mice (n=17, respectively). One week later the number of tumor infiltrating regulatory T cells and the number of PD-1-CD8 T cells were quantified in the tumor. Mice treated with PTM fusion protein-transduced T cells had a higher PD-1-CD8 T cell to Treg ratio than mice treated with untransduced T cells. Bars represent SEM.

FIG. 8: Functional analysis of human PD-1-CD28-fusion protein (hPTM; SEQ ID NOs: 23 (nucleic acid), 24 (protein))

hPTM (SEQ ID NOs: 23 (nucleic acid); 24 (protein))- or untransduced primary human T cells were stimulated with anti-CD3 antibody, anti-CD3 plus anti-CD28 antibodies or anti-CD3 antibody plus recombinant PD-L1 (purchased from R&D, Catalogue no.: 156-B7-100) and IFN-γ production was measured by ELISA. Differences between stimulation groups were assessed by unpaired Student's t-test. Arrows display SEM and exact p-values are depicted in the Figure.

Figure 9:
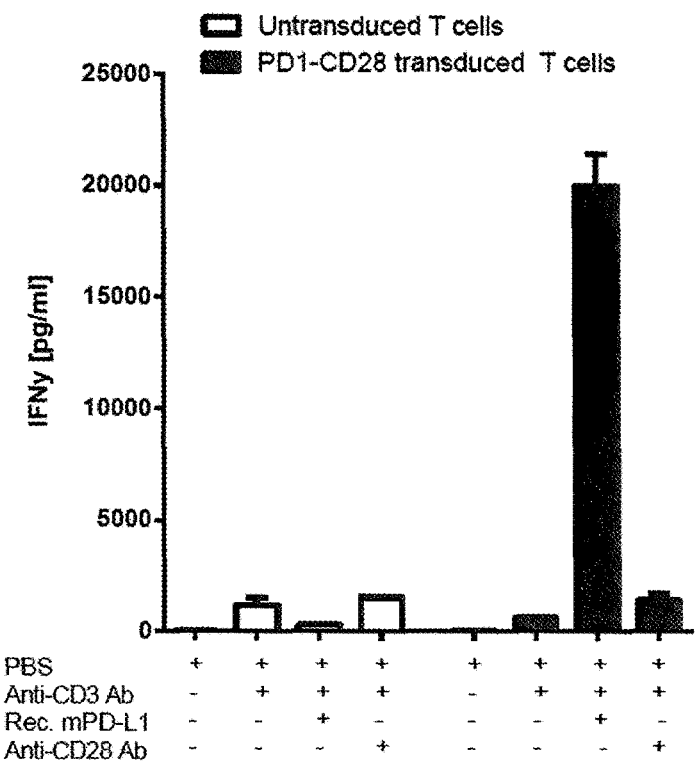
Figure 9:
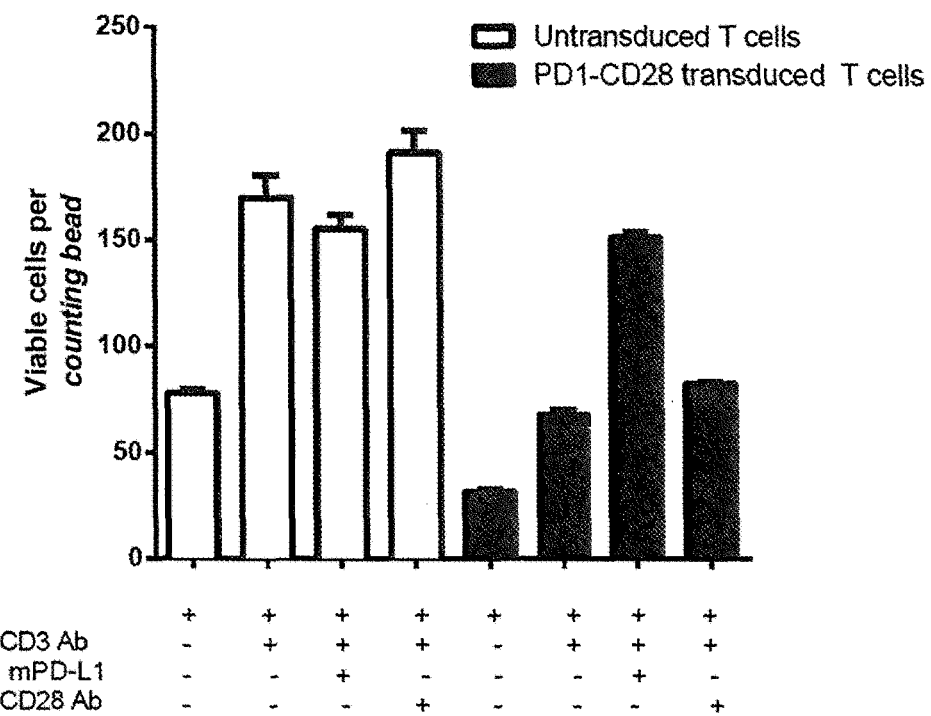
Figure 9:
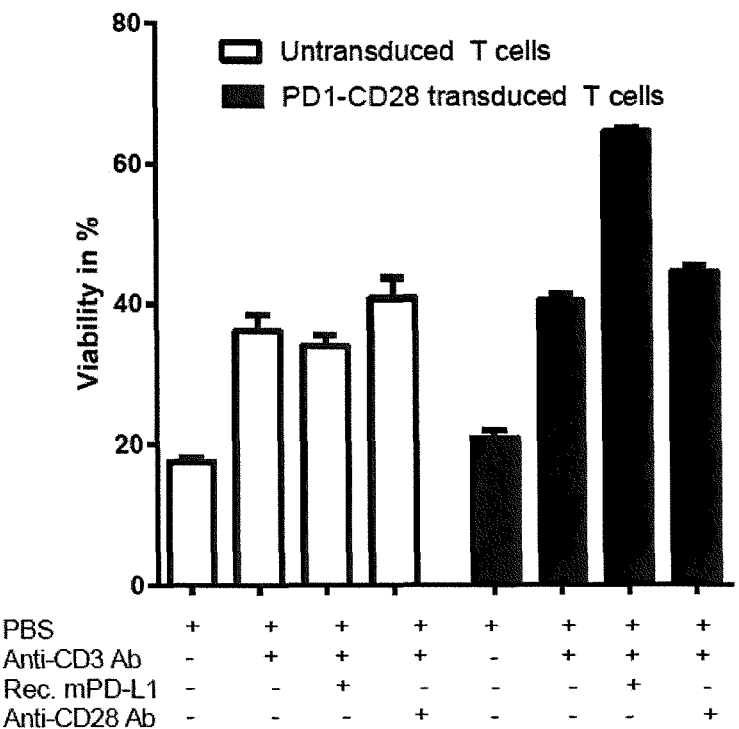
Figure 9:
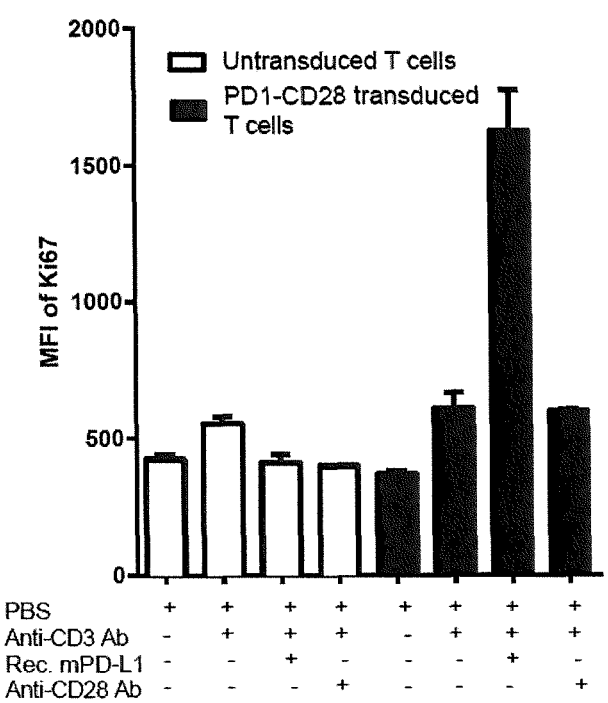
Figure 9:
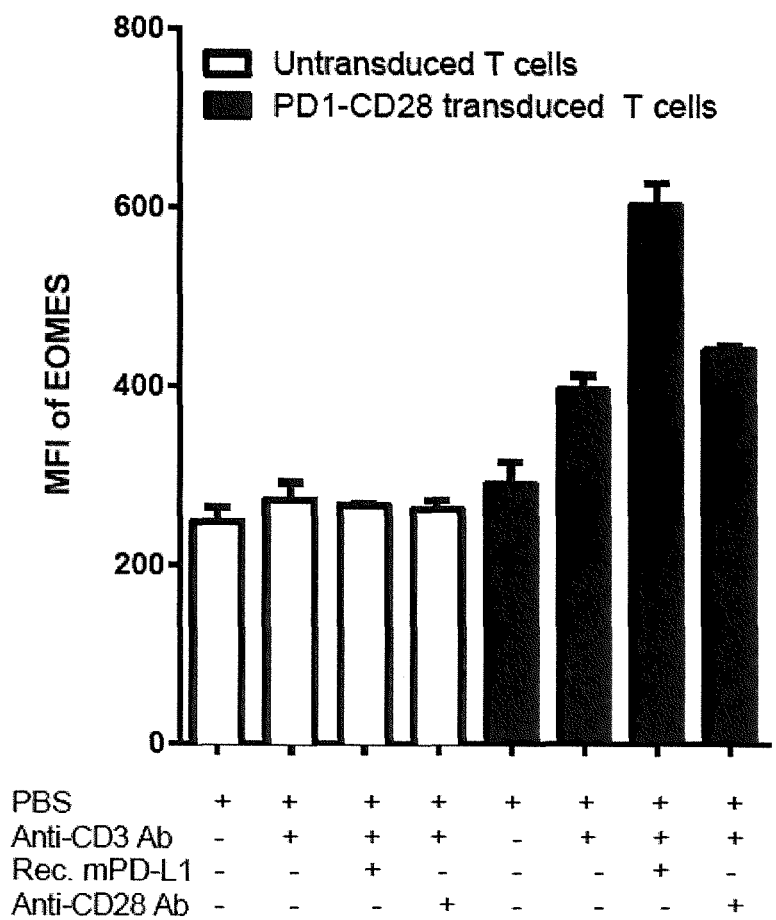

FIG. 9: In vitro characterization of the PD-1-CD28 fusion protein (PD-1 transmembrane domain, PTM fusion protein (SEQ ID NOs: 13 (nucleic acid (cDNA)) and 14 (protein)) transduced CD4+ T cells PTM fusion protein (as depicted in SEQ ID NOs: 13 (nucleic acid (cDNA)); 14 (protein))-transduced or untransduced primary murine/mouse CD4+ T cells were either stimulated with anti-CD3 antibody, anti-CD3 plus anti-CD28 antibodies or with anti-CD3 antibody plus recombinant PD-L1 (SEQ ID NOs: 37 (nucleic acid (cDNA)); 38 (protein)).
(A) IFN-γ release was measured by ELISA.
(B) Proliferation was determined by viable cells/bead. Cell numbers were normalized to standardized counting beads.
(C) Viability, Fixable Viability Dye (AmCyan, BioLegend) by flow cytometry.
(D) Intracellular staining of the mitosis marker ki67.
(E) Intracellular staining of the transcription/activation marker EOMES.

Experiments A to E are representative of at least two independent experiments each performed in triplicates. Bars represent SD. All tests are two-sided.

Figure 10:
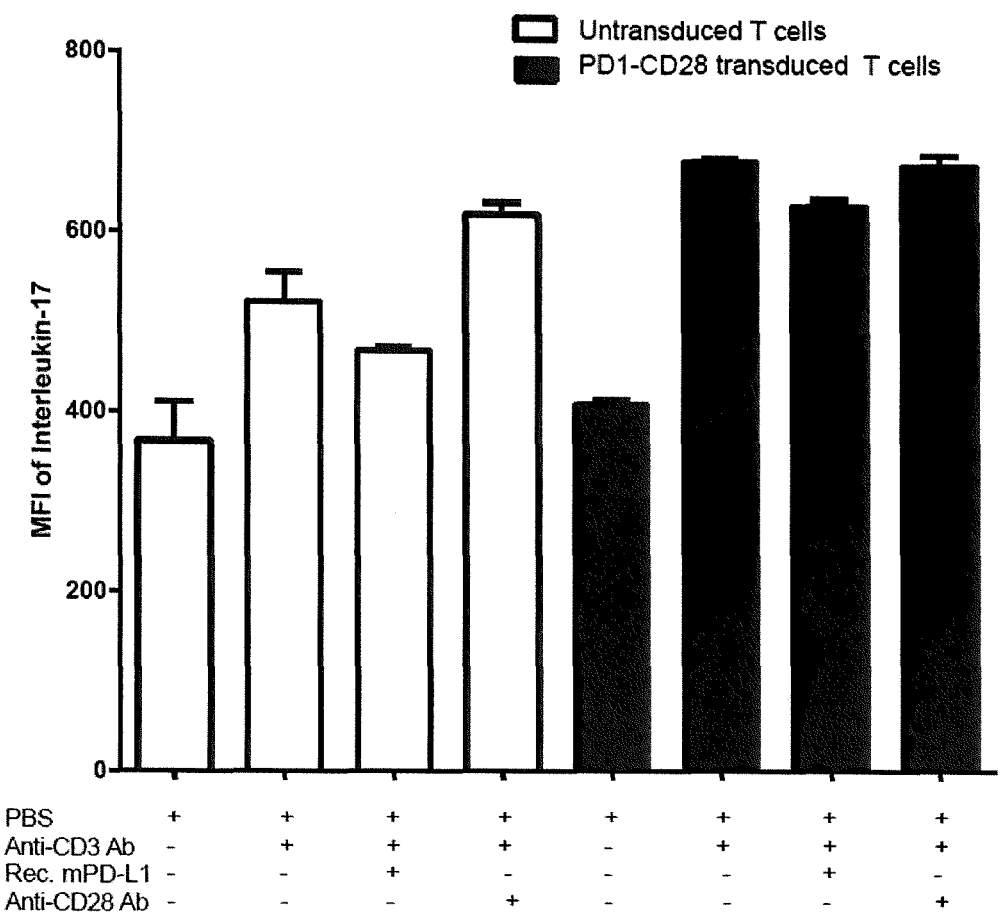
Figure 10:
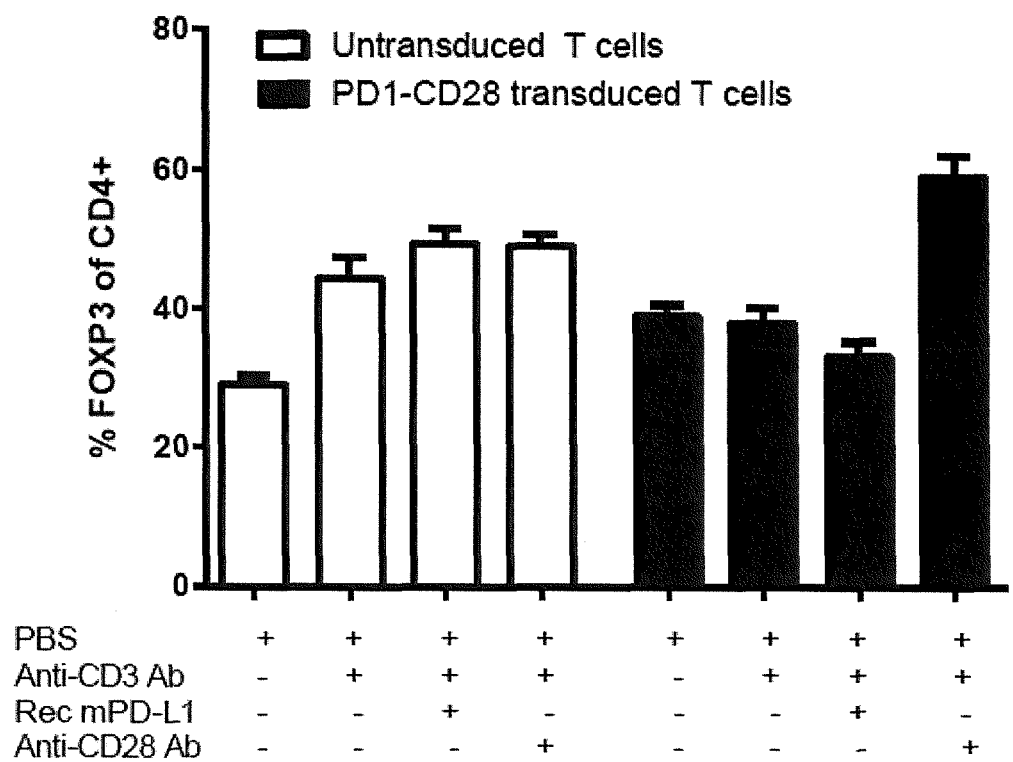

FIG. 10: In vitro phenotypic characterization of the PD-1-CD28 fusion protein (PD-1 transmembrane domain, PTM fusion protein (SEQ ID NOs: 13 (nucleic acid (cDNA)) and 14 (protein)) transduced CD4+ T cells PTM fusion protein (as depicted in SEQ ID NOs: 13 (nucleic acid (cDNA)); 14 (protein))-transduced or untransduced primary murine/mouse CD4+ T cells were either stimulated with anti-CD3 antibody, anti-CD3 plus anti-CD28 antibodies or with anti-CD3 antibody plus recombinant PD-L1 (SEQ ID NOs: 37 (nucleic acid (cDNA)); 38 (protein)).
(A) IL-17 expression was assessed by anti-IL17 staining (FITC, clone TC11-18H10.1, BioLegend) and measured by flow cytometry.
(B) FoxP3 expression was assessed by anti-FoxP3 staining (PE, clone 150D, BioLegend) and measured by flow cytometry.

Experiments A and B are representative of at least two independent experiments each performed in triplicate. Bars represent SD. All tests are two-sided.

Figure 11:
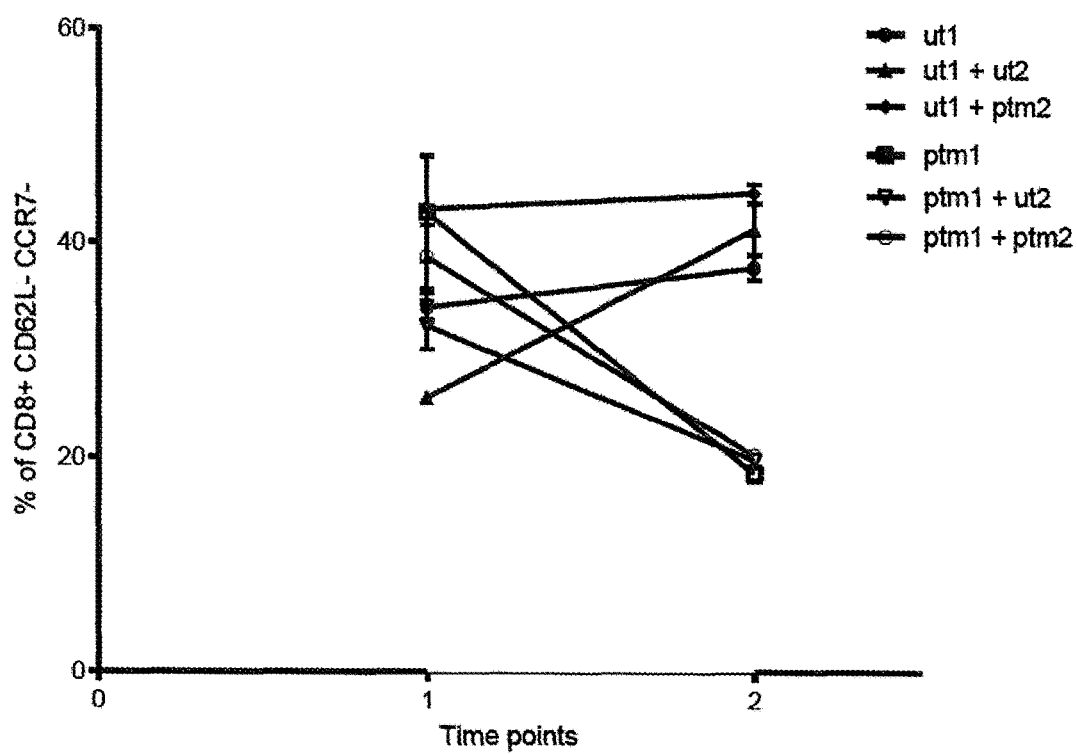
Figure 11:
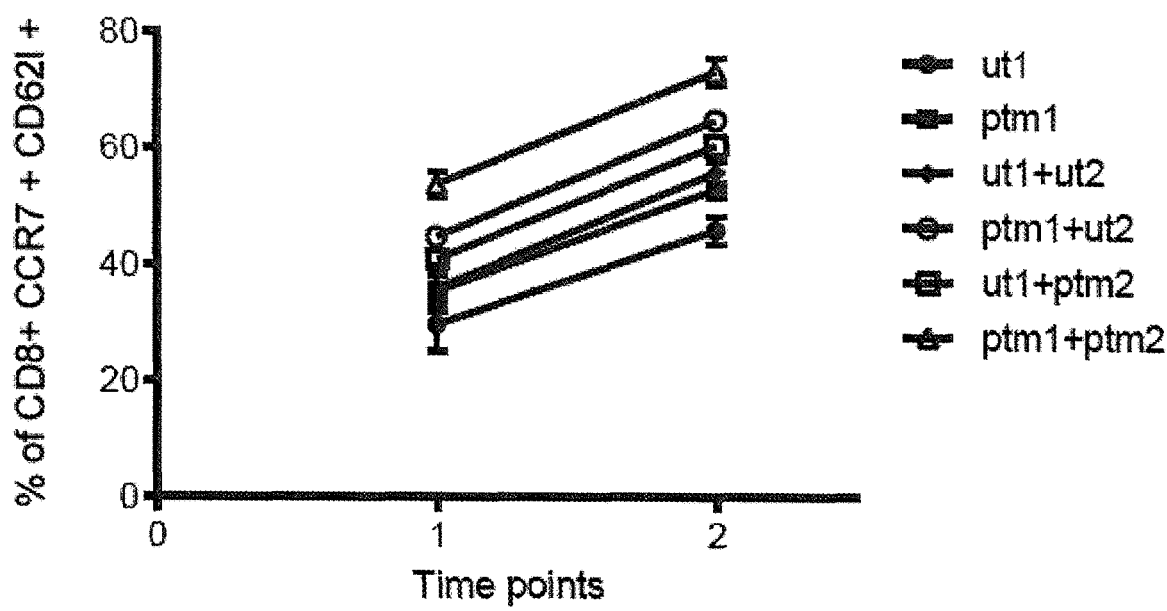
Figure 11:
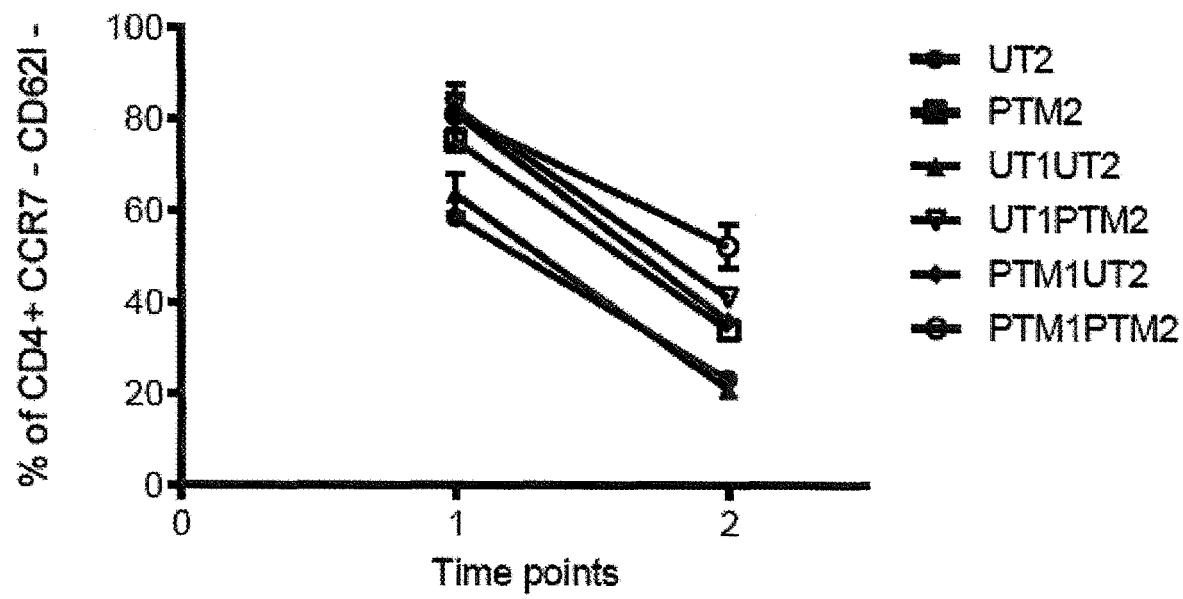
Figure 11:
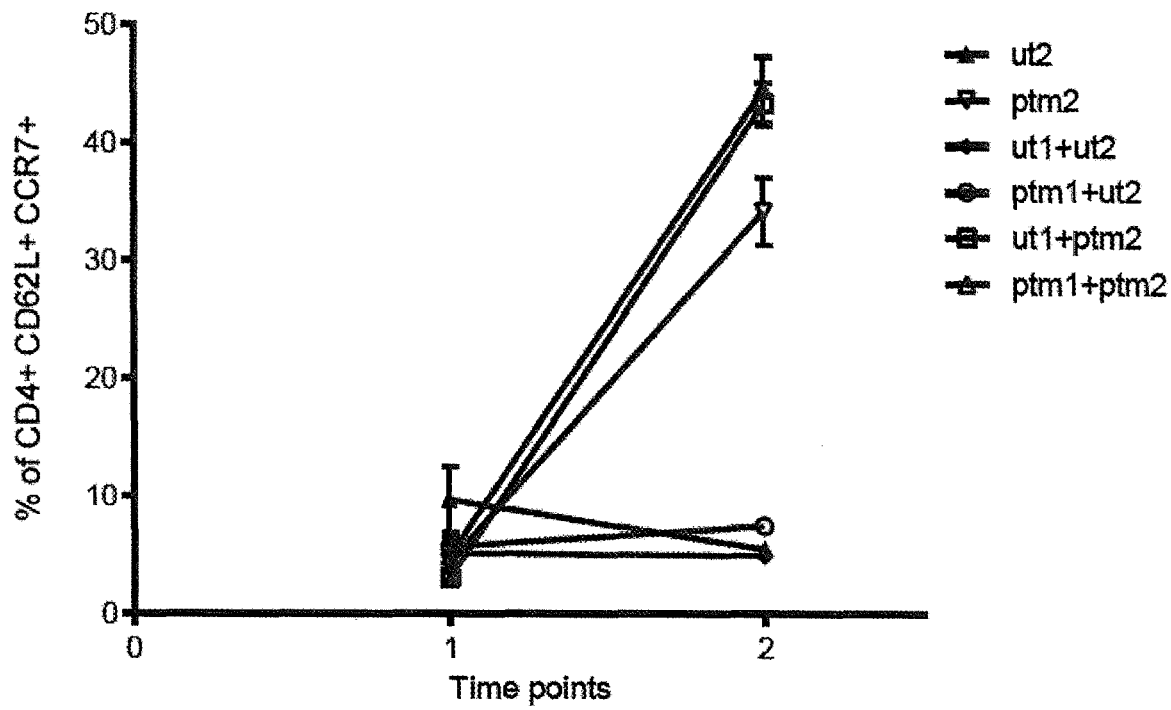
Figure 11:
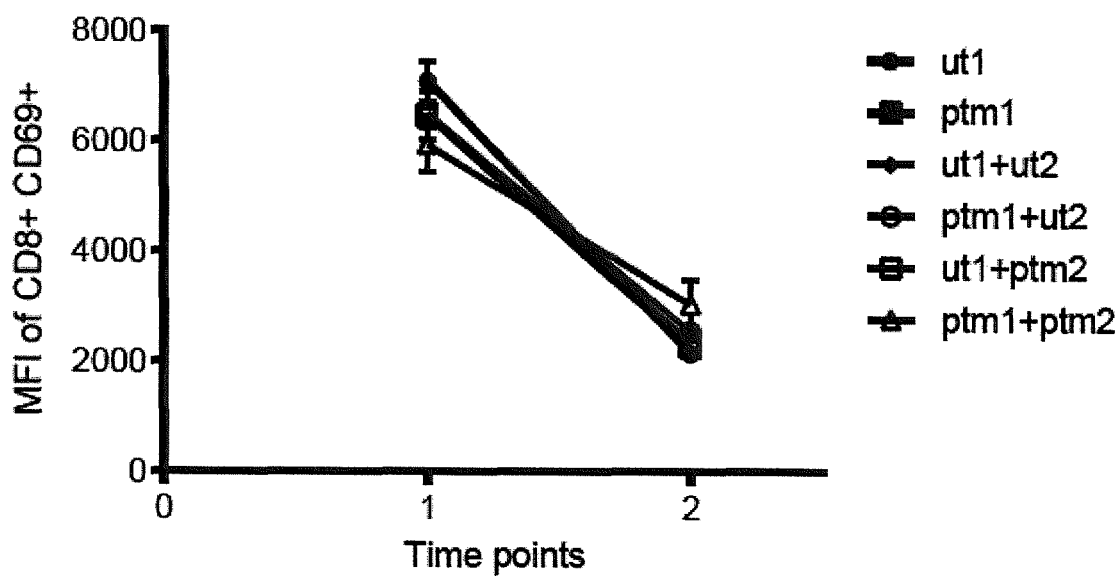
Figure 11:
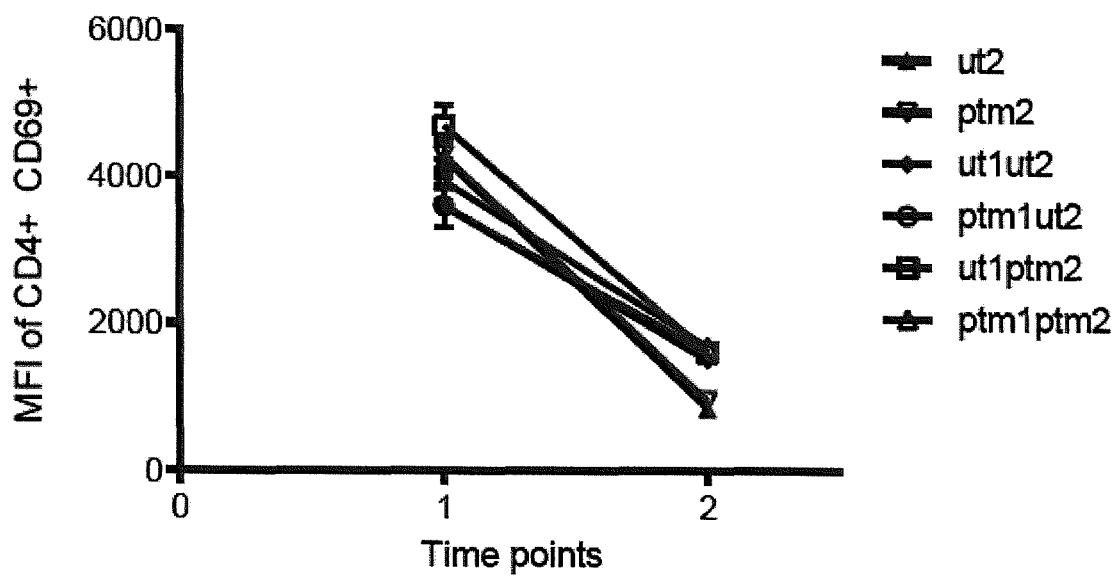
Figure 11:
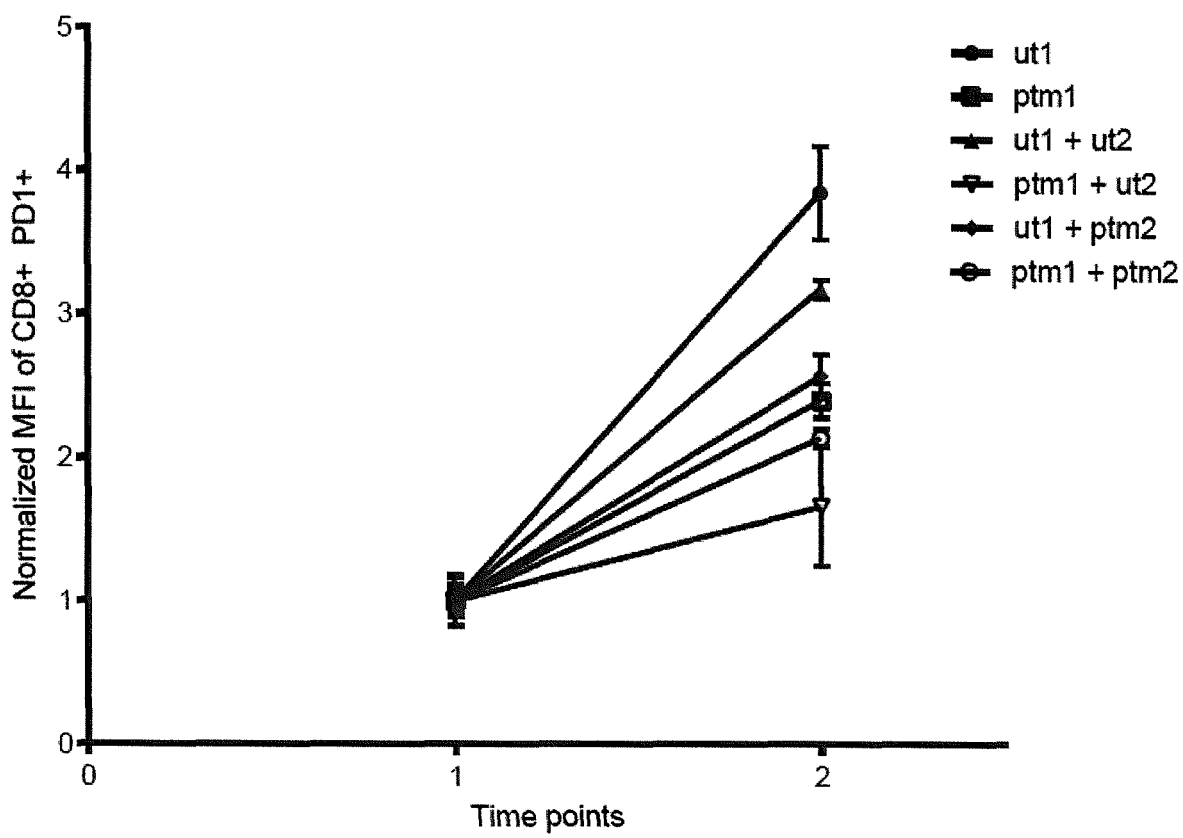

FIG. 11: In vitro phenotypic characterization of the PD-1-CD28 fusion protein (PD-1 transmembrane domain, PTM fusion protein (SEQ ID NOs: 13 (nucleic acid (cDNA)) and 14 (protein)) transduced T cells Antigen (OVA) specific, pre-stimulated PTM (as depicted in SEQ ID NOs: 13 (nucleic acid (cDNA)); 14 (protein))-transduced or untransduced primary murine T cells were co-cultured with PancOVA tumor cells. Timepoint 1 is after 36 h stimulation with agonistic anti-CD3e antibody and recombinant murine PD-L1. Timepoint 2 is after 12 h subsequent co-culture with PancOVA cells.
(A) Percentage of viable CD8+CD62L− CCR7− cells.
(B) Percentage of viable CD8+CD62L+ CCR7+ cells.
(C) Percentage of viable CD4+CD62L− CCR7− cells.
(D) Percentage of viable CD4+CD62L+ CCR7+ cells.
(E) Percentage of viable CD8+CD69+ cells.
(F) Percentage of viable CD4+CD69+ cells.
(G) Percentage of viable CD8+PD1+ cells.

In experiments A to G, all values were determined by flow cytometry and are representative of at least two independent experiments each performed in triplicate. Bars represent SD. All tests are two-sided.

Figure 12:
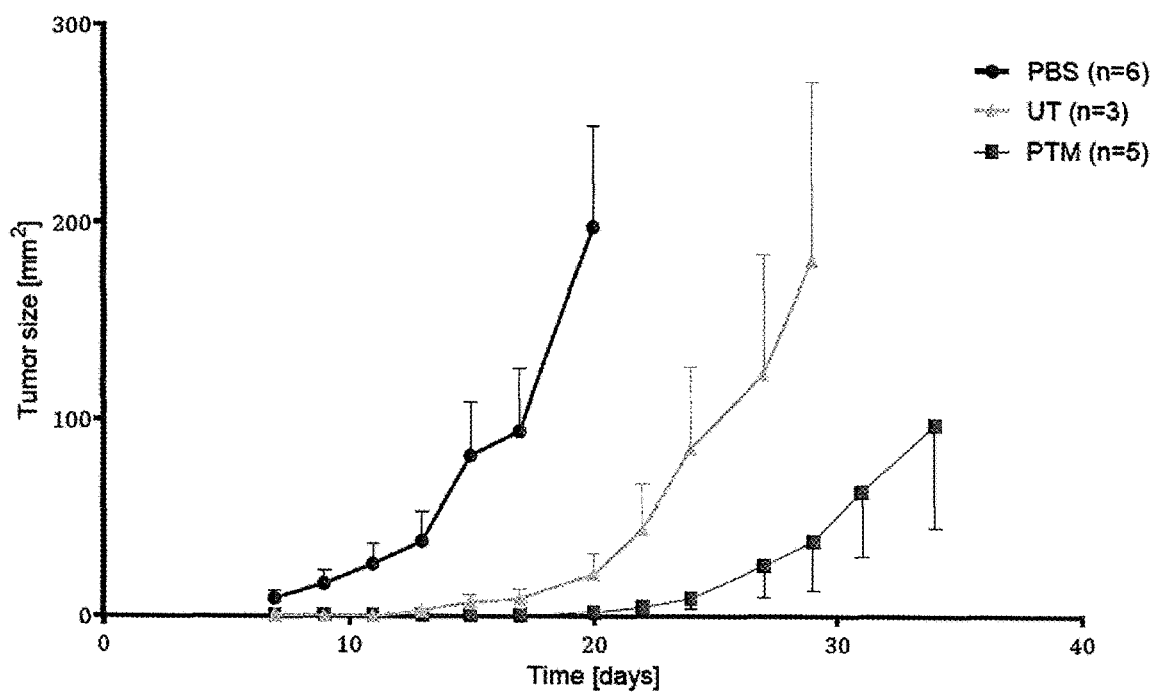
Figure 12:
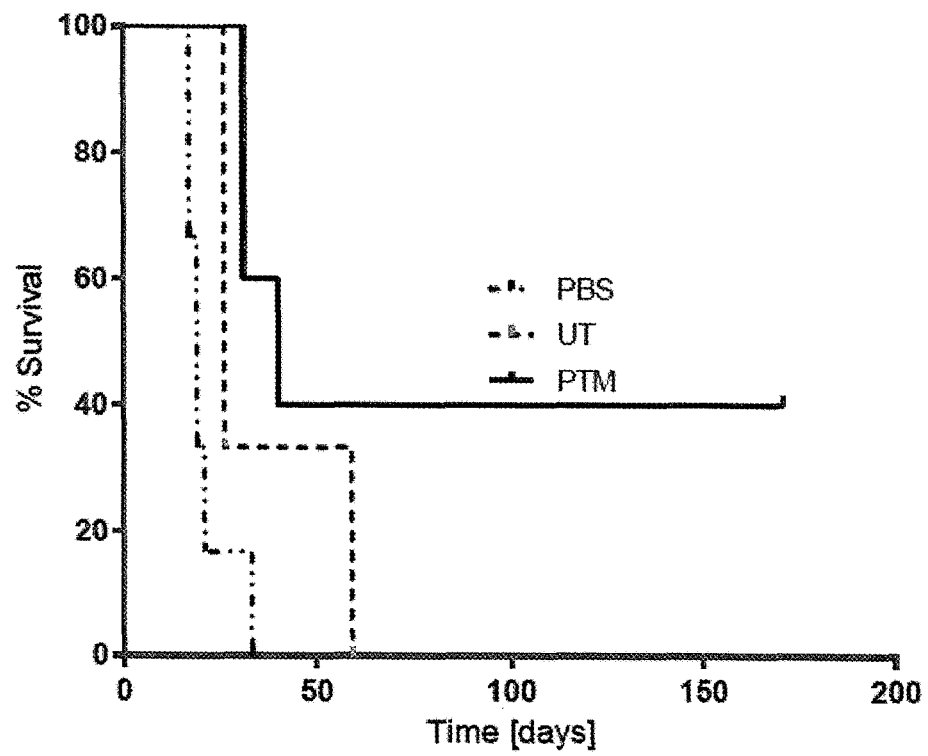

FIG. 12: Therapeutic efficacy of PTM fusion protein-transduced OT-1 T cells in vivo in EG7-PD-L1 tumor model 14 mice were injected subcutaneously with EG7-PD-L1 cells. Once the tumors were established, 6, 3 and 5 mice were randomized either to no treatment (PBS), to adoptive transfer of untransduced OT-1 T cells and to adoptive transfer of PTM-protein-transduced OT-1 T cells, respectively. The figures are representative of 3 independent experiments with 3 to 6 mice per group. Tumor size was measured in a blinded fashion every 2 to 3 days, (A). Survival curves from the experiment of FIG. 12A, (B). Surviving mice (n=2) were rechallenged with EG7-PD-L1 cells at the same time as tumor-naïve wild type mice (n=2), (C).

Survival analysis was performed using the log-rank test. For comparison, tumor growth two-way ANOVA with correction for multiple testing was used. All tests are two-sided.

The following Examples illustrate the invention

Illustratively, in the following Examples 1 to 3 and 5, the fusion protein was constructed with the murine sequences of the PD-1 polypeptide and the CD28 polypeptide. Example 4 relates to the functional analysis of a human PD-1-CD28 fusion protein (SEQ ID NOs: 23 (nucleic acid (cDNA)); 24 (protein)) comprising a PD-1 polypeptide which is operably linked/fused via its C-terminus to the N-terminus of an intracellular domain of a human CD28 polypeptide (SEQ ID NOs: 21 (nucleic acid (cDNA)); 22 (protein)), wherein the PD-1 polypeptide comprises the extracellular domain of PD-1 (SEQ ID NOs: 17 (cDNA), 18 (protein)) and the transmembrane domain of PD-1 (SEQ ID NOs: 19 (cDNA), 20 (protein)) as depicted in SEQ ID NO: 15 (nucleic acid) and 16 (protein). The PD-1-CD28 fusion protein as prepared in Example 4 has the amino acid sequence as shown in SEQ ID NO: 24 (encoded by a cDNA shown in SEQ ID NO: 23).

EXAMPLE 1: GENERATION OF THE PD-1-CD28 FUSION PROTEINS

Example 1.1 the Murine PD-1-CD28 Fusion Proteins PTM (SEQ ID NOs: 13 (Nucleic Acid (cDNA)) and 14 (Protein), CTM (SEQ ID NOs: 43 (Nucleic Acid (cDNA)) and 44 (Protein)), CEX (SEQ ID NOs: 49 (Nucleic Acid (cDNA)) and 50 (Protein)), PTM-FMNM (SEQ ID NOs: 51 (Nucleic Acid (cDNA)) and 52 (Protein)), PTM-AYAA (SEQ ID NOs: 53 (Nucleic Acid (cDNA)); 54 (Protein)) and PTM-FMNM-AYAA (SEQ ID NOs: 55 (Nucleic Acid (cDNA)); 56 (Protein))

The PD-1-CD28 fusion proteins were generated by overlap extension PCR and recombinant expression cloning into the retroviral pMP71 vector (Schambach et al., Mol Ther 2(5) (2000), 435-45; EP-B1 0 955 374). Amplification was done in three steps: first, PD-1-extracellular and transmembrane domain was amplified with a partial overlap for CD28 intracellular domain (5'-ATAGCGGCCG CGCCACCATG TGGGTCCGG-3' (SEQ ID NO: 59); 5'-CCTTCTACTA TTGCAGAAGA CAG-3' (SEQ ID NO: 60)). At the same time, CD28 intracellular was amplified with a partial overlap for PD-1-transmembrane domain (5'-CTGTCTTCTG CAATAGTAGA AGG-3' (SEQ ID NO: 61); 5'-TATGAAT-TCT CAGGGGCGGT ACGCTGCA-3' (SEQ ID NO: 62)). In the third reaction step, both products were used as amplification templates using the 5'-PD-1-primer (5'-ATAGCGGCCG CGCCACCATG TGGGTCCGG-3' (SEQ ID NO: 63) and the 3'-CD28 primer (5'-TATGAATTCT CAGGGGCGGT ACGCTGCA-3' (SEQ ID NO: 64)). After amplification, the insert was ligated into the pMP71 vector using EcoRI and NotI restriction enzyme cutting and DNA-ligation.

The resulting murine PD-1-transmembrane fusion protein (PTM; SEQ ID NOs: 13 (nucleic acid (cDNA)) and 14 (protein)) consists of murine PD-1 (mPD-1) (Uniprot Entry Q02242 (accession number with version number: 125 and version 1 of the sequence) amino acids (AA) 1-190; SEQ ID NOs: 5 (nucleic acid (cDNA)) and 6 (protein)) and murine CD28 (mCD28) (Uniprot Entry No.: P31041 (accession number with version number: 127 and version 2 of the sequence) AA 178-218; SEQ ID NOs: 11 (nucleic acid (cDNA)) and 12 (protein)).

The resulting murine CD28-transmembrane fusion protein (CTM (SEQ ID NOs: 43 (nucleic acid (cDNA)) and 44 (protein)) consists of murine PD-1 (AA 1-169; SEQ ID NOs: 39 (nucleic acid (cDNA)) and SEQ ID NO: 40 (protein)) and murine CD28 (AA 151-218 (SEQ ID NOs: 41 (nucleic acid (cDNA)) and 42 (protein)).

The resulting murine CD28 extra- and transmembrane fusion protein (CEX (SEQ ID NOs: 49 (nucleic acid (cDNA)) and SEQ ID NO: 50 (protein)) consists of murine PD-1 (AA 1-169 (SEQ ID NOs: 45 (nucleic acid (cDNA)) and SEQ ID NO: 46 (protein)) and murine CD28 (AA 115-218 (SEQ ID NOs: 47 (nucleic acid (cDNA)) and SEQ ID NO: 48 (protein)).

The murine PTM variants were generated from PTM fusion receptor (SEQ ID NOs: 13 (nucleic acid (cDNA)); 14 (protein)) by point mutations as follows: mutation of YMNM (AA 189-192; SEQ ID NO: 29) to FMNM (SEQ ID NO: 31) resulting in the construct PTM-FMNM (SEQ ID NOs: 51 (nucleic acid (cDNA)); 52 (protein)); mutation of PYAP (AA 206-209; SEQ ID NO: 30)) to AYAA (SEQ ID NO: 32) resulting in the construct PTM-AYAA (SEQ ID NOs: 53 (nucleic acid (cDNA)); 54 (protein)); and the double mutant PTM-FMNM-AYAA (SEQ ID NOs: 55 (nucleic acid (cDNA)); 56 (protein)). The variants of the murine PTM fusion protein were generated by site directed mutagenesis using the wild type construct using the Gene Art site directed mutagenesis kit (Life Technologies) to exchange either one (YMNM (SEQ ID NO: 29) to FMNM (SEQ ID NO: 31)) or two (PYAP (SEQ ID NO: 30) to AYAA (SEQ ID NO: 32)) base pairs.

Example 1.2 PD-1-Deletion Mutant (SEQ ID NOs: 57 (Nucleic Acid (cDNA)) and 58 (Protein))

The PD-1 deletion mutant has been previously described by Okazaki T et al., Proc Natl Acad Sci USA 98(24) (2001), 13866-13871. The PD-1 deletion mutant contains the sequences as depicted in SEQ ID NO: 57 (nucleic acid (cDNA)) and 58 (protein).

EXAMPLE 2: TRANSDUCTION OF T-CELLS AND CYTOTOXIC KILLING ASSAYS

2.1 Cell Lines

The murine pancreatic cancer cell line Panc02 and its ovalbumin-transfected counterpart Panc02-OVA have been previously described (Jacobs et al., Int J Cancer 128(4) (2011), 897-907). The Panc02-cell line was generated through injection of the carcinogen Methycholantren A into the pancreas of wild type C57Bl/6 mice to induce carcinogenesis. Panc02-OVA-PD-L1 and Panc02-PD-L1 were generated by transduction with pMXs-puro (Kitamura et al., Exp. Hematol. 31 (2003), 1007-1014) containing full length murine PD-L1 (SEQ ID NOs: 29 (nucleic acid (cDNA)) and 30 (protein)) and selection with puromycin with an end concentration of 10 µg/ml. The packaging cell line Plat-E has been previously described by Morita et al., Gene Ther 7 (2000), 1063-6). All cells were cultured in DMEM with 10% fetal bovine serum (FBS, Life Technologies, USA), 1% penicillin and streptomycin (PS) and 1% L-glutamine (all from PAA, Germany). 10 µg/ml puromycin and 1 µg/ml blasticidin (Sigma, Germany) were added to the Plat-E (Platinum-E) medium. Primary murine T cells (see section 2.5 below for the cultivation) were cultured in RPMI 1640 with 10% FBS, 1% PS and 1% L-glutamine, 1% sodium pyruvate, 1 mM HEPES and 50 µM β-mercaptoethanol were added to the T cell medium.

2.2 Animals

Mice transgenic for a T cell receptor specific for ovalbumin (OT-1) were obtained from the Jackson laboratory, USA (stock number 003831) and were bred in our animal facility under specific-pathogen free (SPF) conditions. OT-1 mice were crossed to CD45.1 congenic marker mice (obtained from the Jackson laboratory, stock number 002014) and to CD90.1 congeneic marker mice (Stock number: 000406) to generate CD45.1-OT-1 and CD90.1-OT-1 mice, respectively. Wild type C57Bl/6 mice were purchased from Janvier, France. Tumors were induced by subcutaneous injection of $2\times10^6$ tumor cells and mice were treated by i.v. injection of T cells as indicated. For rechallenge experiments, mice were injected subcutaneously with $0.5\times10^6$ cells in the flank opposite to the site of the previously rejected tumor. All experiments were randomized and blinded. For neutralization experiments, anti-IFN-γ antibody R4-6A2 (BioXcell, USA) or isotype control (BioXcell, USA) was applied i.p. at a dose of 200 µg per animal every three days for four doses. Tumor growth and condition of mice were monitored every other day.

2.4 T-Cell Transduction

The retroviral vector pMP71 (Schambach et al., Mol Ther 2(5) (2000), 435-45; EP-B1 0 955 374) was used for transfection of the ecotrophic packaging cell line Plat-E (Platinum-E). Transduction was performed according to the method described by Leisegang et al., J Mol Med 86 (2008), 573-83; Mueller et al., J Virol. 86 (2012), 10866-10869; Kobold et al., J Natl Cancer Inst (2014), in press. In brief, packaging cell line Plat E (as described by Morita et al., Gene Ther 7 (2000), 1063-6) was seeded in 6-well plates and grown over night to 70-80% confluence. On day one, 16 μg of DNA were mixed together with 100 mM CaCl2 (Merck, Germany) and 126.7 μM Chloroquin (Sigma, USA). Plat-E cells were starved for 30 min in low serum medium (3%) and then incubated for 6 h with the precipitated DNA. Medium was then removed and exchanged with culture medium. On day two, primary splenocytes were harvested from C57Bl/6 mice (Harlan Laboratories, The Netherlands). Single cell suspensions of splenocytes were stimulated with anti-CD3 (clone 145-2c11 BD Pharmingen, USA), anti-CD28 (clone 37.51, BD Pharmingen, USA) and recombinant murine IL-2 (Peprotech, Germany) in T cell medium over night. On day 3, 24-well plates were coated with 12.5 μg/ml recombinant retronectin (Takara Biotech, Japan) for 2 h at room temperature, blocked with 2% bovine serum albumin (Roth, Germany) for 30 min at 37° C. and washed with PBS. Supernatant of Plat E was harvested and passed through a filter (40 μm, Milipore, USA). Fresh T cell medium was then added to Plat E cells. 1 ml of filtered supernatant was distributed in each well and spinoculated for 2 h at 4° C. Supernatant was then removed from the 24-well plate. $10^6$ T cells were seeded in one ml T cell medium supplemented with 10U IL-2 and 400000 anti-CD3 and anti-CD28 beads (Invitrogen, Germany) per well and spinoculated at 800 g for 30 min at 32° C. On day four, Plat E supernatant was again harvested and filtered. 1 ml was added to each well of the 24-well plate and spinoculated at 800 g for 90 min at 32° C. Cells were subsequently incubated for 6 additional hours at 37° C. 1 ml supernatant was replaced by T cell medium with IL-2. On day five, cells were harvested, counted and reseeded at $10^6$ cells/ml density in T cell medium supplemented with 10 ng IL-15 per ml (Peprotech, Germany). T cells were kept at this density until day 10 when cell analysis or functional assays were performed.

2.5 Co-Culture of T Cells and Tumor Cells

T cells and tumor cells were co-cultured for 48 h at a ratio of 10:1 in the presence or absence of anti-PD-1 blocking antibody (10 μg/ml, clone RPM1-14, Biolegend) or anti-mouse H2kb SIINFEKL antibody (20 μg/ml, clone 25.D1-16, Miltenyi Biotech, Germany). Supernatants were analyzed for IFN-γ by ELISA (BD).

EXAMPLE 3: CYTOKINE RELEASE, T CELL PROLIFERATION AND KILLING ASSAYS 3.1 Functional T Cell Assays T cells were stimulated with either anti-CD3e antibody (100 ng/ml, clone 145-2C11, eBioscience), anti-CD28 antibody (2 μg/ml, clone 37.51, eBioscience) or recombinant PD-L1 Fc chimera (5 μg/ml, R&D Systems) or the combination of these for 48 h. Cytokines were quantified in supernatants by ELISA (IL-2 and IFN-γ, both BD; catalogue number: DY402 and DY485, respectively) or qualitatively detected by immunoblotting (murine cytokine array from R & D; catalogue number: ARY006). For proliferation assays, cells were stimulated as described above for 24 h before staining as described. Cells were counted by addition of counting beads (Life Technologies, Germany; catalogue number: C36950) and subsequent analysis by flow cytometry. For killing assays, 300.000 T cells transformed with the fusion proteins were stimulated for 40 h with anti-CD3e antibody and recombinant PD-L1 (R&D, catalog number: 1019-B7-100), as indicated above. In the meantime, PaneOVA-tumor cells were seeded at a density of 15.000 per well of an 8-well plate and grown overnight. After 16 h, stimulated T cells were added to the wells containing tumor cells and cell numbers were continuously monitored by impedance measurement using an ICELLigence instrument (ACEA Bioscience, USA).

3.2 Stimulation of Human T Cells

Human CD3+ PBMCs were retrovirally transduced with human PTM (hPTM) fusion protein (SEQ ID NOs: 23 (nucleic acid (cDNA)) and 24 (protein)), and expanded for 4 days using IL-2 (Peprotech) and IL-15 (Peprotech). T cell stimulation was determined performing a stimulation assay. Therefore, flat bottom 96-well plates were coated with either PBS containing 0.1 μg/ml anti-human CD3 antibody (clone: HIT3a; eBioscience) or 0.1 μg/ml anti-human CD3 antibody and 5 μg/ml recombinant human Fc B7-H1 chimera (R&D) or 0.1 μg/ml anti-human CD3 antibody and 2 μg/ml anti-human CD28 antibody (clone: cd28.2; eBioscience) overnight at 4° C. $3.0 \times 10^5$ transduced cells per well were placed in the coated 96-well plate. After 48 h incubation at 37° C., 5% $CO_2$ cell supernatants were collected. Human IFN-γ release was quantified using the human IFN-γ-ELISA (BD Bioscience) according to manufactures guidelines.

3.3 Restimulation of Splenocytes

Splenocytes from mice after tumor rejection or from control mice were incubated for 4 h (ICS), 1 μg/ml of the peptides SIINFEKL (SEQ ID NO: 65), TRP2 or P15E (all from JPT Peptides, Germany) prior to analysis by flow cytometry. Background normalization was done by calculating the ratio of stimulation with active versus control peptide TRP2: calculated with the formula: % CD8+ IFNγ+ cells from target condition/% CD8+ IFNγ+ of TRP2 condition.

3.4 Flow Cytometry

Multi-color flow cytometry in a BD FACS Canto II (BD bioscience, Germany) used the following antibody panels: for analysis of adoptively transferred OT-1 T cells, anti-PD-1 (PE-Cy7, clone 29F.1A12) and anti-CD8 (APC, clone 53.6-7, both from Biolegend, USA); for p-Akt analysis, anti-mouse CD8a (Pacific Blue, clone 53-6.7) and anti-mouse PD-1 (PeCy7, clone 29F.1A12, both Biolegend, USA), subsequent fixation and permeabilization using a Foxp3/Transcription Factor Staining Buffer Set (eBioscience, USA) and staining with anti-Akt (p5473) (AlexaFluor 647, clone M89-61, eBioscience). For ki67 and proliferation analysis, cells were stained with Fixable Viability Dye (eFluor™ 780, eBioscience), anti-mouse CD8a and anti-mouse PD-1 (APC clone 29F.1A12, Biolegend) and were subsequently fixated and permeabilized. After intracellular staining with anti-Ki67 (PE, clone 16A8, Biolegend), cells were washed and resuspended in PBS containing Count Bright Absolute Counting Beads (Life Technologies). For tracking experiments, cells were stained with anti-mouse CD8a (APC-Cy7, clone 53-6.7, Biolegend), anti-mouse CD45.1 (APC, clone A20, eBioscience) or anti-mouse CD90.1 (PeCy7 or Pacific Blue™, Biolegend clone OX7). For co-tracking experiments, the ratio between CD45.1 and CD90.1 cells was calculated. Cells were fixated/permeabilized and stained intracellularly with anti-mouse IFN-γ antibody (FITC, clone XMG1.2, Biolegend). For in vitro restimulation, cells were stained with anti-CD3e-APC (clone 145-2C11, Biolegend), anti-CD8-PerCP (clone 53-6.7, Biolegend) and anti-IFN-γ-FITC (clone XMG1.2, Biolegend) antibodies. For PD-L1 binding capacity, cells were incubated with 5 μg/ml of recombinant PD-L1-Fc (R & D) and were stained with anti-human IgG-APC antibody (clone HP6017, Biolegend). For PD-L1 expression analysis, tumor cells were stimulated with recombinant IFN-γ as indicated (Peprotech, Germany) for 48 h. Cells were stained with anti-PD-L1-APC antibody (clone 10F.9G2, Biolegend). Staining of myeloid-derived suppressor cells was done using anti-CD45 (PacBlue, clone 30F11, Biolegend), anti-CD11b (Percp-Cy5.5, clone M1/70, Biolegend), anti-Ly6 (APC-Cy7, HK1.4, Biolegend) and anti-Gr1 (FITC, clone RB6-8C5, Biolegend) antibodies. Regulatory T cells were detected by anti-CD4 (APC-Cy7, clone GK1.5, Biolegend), anti-CD8 (Percp, 53-6.7, Biolegend) antibodies and intracellular staining for Foxp3 (eFluor450, clone FJK-16s, eBioscience).

3.5 Statistical Analysis

For statistics, GraphPad Prism software version 5.0b was used. All variables reported are continuous. Differences between experimental conditions were analyzed using the unpaired two-sided Student's t-test. For comparison of experimental conditions of individual mice, the Mann-Whitney test was used. p-values <0.05 were considered significant. For in vivo experiments, differences between groups were analyzed using two-way ANOVA with correction for multiple testing by the Bonferroni method.

Overall survival was analyzed by log-rank test. Survival is defined in days from tumor induction until natural death or until mice were euthanized because one of the following predefined criteria was reached: tumor size >225 mm$^2$, weight loss >15% or severe distress. Data are shown as mean values ±SEM of a minimum of three biological replicates or independent experiments, as indicated.

3.6 Results 3.6.1 Rationale and Design of a New PD-1-CD28 Fusion Receptor

Efficacy of adoptive transfer of OVA-specific CD8$^+$ T cells was assessed in mice bearing established OVA-expressing Panc02 (Panc02-OVA) tumors. Transferred T cells failed to reject tumors in most animals. This was paralleled by upregulation of PD-1 on the transferred T cells infiltrating the tumor (FIGS. 5A and 5B). Given that Panc02-OVA cells express the ligand for PD-1 (PD-L1), which is upregulated by IFN-γ (FIGS. 5C and 5D), this points to a relevant role of the PD-1-PD-L1 axis in suppressing the antigen-specific T cell response in the tumor. Without being bound by theory, it was assumed that protection of the transferred T cells from PD-1-mediated suppression may enhance the efficacy of adoptive T cell therapy. Because PD-1 is a member of the CD28/CTLA-4 family, it appeared possible that receptor signaling could be compatible and that a fusion PD-1-CD28 receptor construct could turn engagement of PD-1 by PD-L1 into CD28 costimulatory activity (scheme in FIG. 5E). Therefore fusion receptors consisting of the extra- and transmembrane portion of PD-1 with the intracellular domain of CD28 for transduction in primary murine T cells were designed.

3.6.2 Functional Analysis of Transduced T Cells In Vitro

To test the functionality of the murine PD-1-transmembrane PD-1-CD28-fusion protein (PTM, SEQ ID NOs: 13 (cDNA) and 14 (protein)), primary murine T cells were transduced and stimulated with agonistic anti-CD3 antibodies and recombinant PD-L1 (SEQ ID NOs: 29 and 30). PTM-transduced T cells showed markedly increased IFN-γ (170+/−26 vs 0.5+/−0.5 ng/ml, p=0.003, FIG. 1A) and IL-2 induction as compared to untransduced T cells (FIG. 6F). Additional stimulation with anti-CD28 antibody further boosted cytokine production (FIG. 7A). Cytokine induction was paralleled by downstream phosphorylation of AKT upon PD-L1 engagement (FIG. 1B), demonstrating CD28 signaling in transduced T cells. Activation of the PTM receptor statistically significantly enhanced the number of viable cells as compared to untransduced T cells (42+/−4 vs 6+/−1 cells per bead, p=0.001, FIG. 1C). This increase in cell numbers was associated with strong ki67 upregulation by the transduced T cells (FIG. 1D), indicating strong mitotic activity. When coculturing PTM-transduced OT-1 T cells with Panc02-OVA or Panc02 cells, strong costimulatory activity was observed, as evidenced by IFN-γ-release in transduced as compared to untransduced T cells (545+/−37 vs 191+/−0.5 ng/ml, p<0.001, FIG. 1E). The costimulatory activity of the murine PTM fusion protein was dependent on the presence of PD-L1, on OVA expression by the tumor cells and on TCR engagement, as evidenced by MHC-I blocking (FIG. 1E) and by coculture with OVA-negative Panc02-PD-L1 cells (FIG. 7B). Anti-CD3 antibody- and PD-L1-prestimulated PTM receptor-transduced T cells mediated immediate and complete lysis of tumor cells, whereas untransduced T cells were ineffective (p<0.001 from 22 h, FIG. 1F). Together, these findings indicate that T cells transduced with the murine PTM fusion protein have become resistant to PD-1-PD-L1 mediated anergy. These results demonstrate the functionality and the therapeutic potential of the murine PD-1-CD28 fusion protein (PTM, SEQ ID NOs: 13 (nucleic acid (cDNA)); 14 (protein)) receptor in vitro.

3.6.3 Functional Comparison of Different PD-1-CD28 Fusion Constructs

Two PD-1-CD28 fusion proteins have been described with up to two-fold cytokine induction, little proliferative activity and some cytolytic potential (Ankri et al., J. Immunol 191(8) (2013), 4121-4129 and Prosser et al., Mol. Immunol. 51(3-4) (2012), 263-272). Given the strong effects observed with the murine PTM fusion protein, it was analyzed whether the difference to our results is related to the structure of the PD-1-CD28 fusion protein (PTM). Therefore, additional fusion proteins for PD-1-CD28 fusion receptor constructs were generated containing the (murine) CD28 transmembrane domain (CTM, SEQ ID NOs: 43 (nucleic acid (cDNA)); 44 (protein)) or the CD28 transmembrane domain plus part of the CD28 extracellular domain (CEX, SEQ ID NOs: 49 (nucleic acid (cDNA)); 50 (protein)); see FIG. 2A. When stimulated with anti-CD3 antibodies and recombinant PD-L1, all receptors were functional as assessed by IFN-γ release (79+/−0.9 vs 4+/−1 vs 7 +/−2 ng/ml, p<0.001, FIG. 2B) and by induction of proliferation (540+/−45 vs 278+/−37 vs 279+/−46 cells per bead, p=0.01 and 0.02, respectively, FIG. 2C). The PTM fusion protein, however, was far superior to the CTM and CEX receptors in terms of both IFN-γ secretion and proliferation. Mechanistically, the enhanced activity was paralleled by enhanced binding of PD-L1 to the PTM fusion protein as opposed to the CTM and CEX fusion protein (MFI 9315+/−165 vs 2311+/−144 vs 2997+/−167, p<0.001, FIG. 2D). The enhanced binding of the PTM fusion protein can only partly be explained by increased surface expression of this construct, as expression on CD8-T cells by flow cytometry was not largely superior for all fusion proteins (FIG. 2E). The enhanced binding of the PTM fusion protein may be responsible for its markedly superior functional activity in comparison to the other fusion proteins CEX and CTM.

3.6.4 Functional Domains Required for PTM Fusion Protein Function

To further dissect the mechanisms underlying the activity of PTM, we generated mutant PD-1-CD28 PTM fusion proteins where the signaling domains of CD28 were rendered non-functional. The YMNM motif of the intracellular CD28 domain is required for optimal cytokine secretion upon CD28 activation and the PYAP motif is essential for both cytokine production and cell proliferative activity (Boomer and Green, Cold Spring Harb Perspect Biol 8 (2010), a002436). We generated a PTM-FMNM mutant construct (SEQ ID NOs: 51 (nucleic acid (cDNA)); 52 (protein)), a PTM-AYAA mutant construct (SEQ ID NOs: 53 (nucleic acid (cDNA)); 54 (protein)) and a PTM-FMNM-AYAA double mutant construct (SEQ ID NOs: 55 (nucleic acid (cDNA)); 56 (protein)) for expression in primary murine T cells (FIG. 3A). T cells expressing the PTM construct or one of the three mutant constructs were stimulated with anti-CD3 antibodies and recombinant PD-L1. PTM fusion construct-transduced T cells produced statistically significantly more IFN-γ than PTM-FMNM, PTM-AYAA or PTM-FMNM-AYAA (22+/−2 vs 8+/−1 vs 1+/−0.07 vs 0.1+/−0.05 ng/ml, p<0.001, FIG. 3B). PTM fusion construct engagement induced proliferation in a PYAP-dependent manner, while YMNM was dispensable for the proliferative effect (FIG. 3C). In contrast, production of various cytokines and chemokines by PTM fusion construct engagement seems to be dependent on both motifs, since mutant constructs were weaker inducers compared to native PTM fusion protein (FIG. 3D).

3.6.5 Therapeutic Efficacy of PD-1-CD28 Fusion Protein-Transduced OT-1 T Cells in a Murine Pancreatic Cancer Model To further assess the potency of murine PD-1-CD28 (PTM; SEQ ID NOs: 13 (nucleic acid (cDNA)); 14 (protein)) fusion protein-transduced antigen-specific T cells, we treated mice bearing subcutaneous Panc02-OVA tumors with untransduced OT-1 T cells or PTM fusion protein-transduced OT-1 T cells. PTM receptor-transduced T cells induced superior anti-tumor immunity as compared to mice receiving untransduced T cells (FIG. 4A).

Interestingly, PTM fusion protein-transduced OT-1 T cells retained their therapeutic potential in the Panc02-OVA-PD-L1 model strongly overexpressing PD-L1 while the effect of untransduced OT-1 cells was almost completely abrogated (FIG. 7C). When rechallenged with Panc02-OVA cells, 11 of 12 mice previously treated with PTM fusion protein-transduced OT-1 T cells remained tumor free compared to 0% of control mice (p<0.001, FIG. 4B). Moreover, when rechallenged with wild-type Panc02 cells, 9 of 11 mice previously treated with PTM fusion protein-transduced OT-1 T cells remained tumor free (p<0.001, FIG. 4C). These results are suggestive of epitope spreading in cured mice leading to immunity against other Panc02-specific tumor-associated antigens, such as p15E (Bauer et al., Gut 56(9) (2007), 1275-1282). Therefore, lymph nodes of tumor-free mice were analyzed for the presence of SIINFEKL (OVA; SEQ ID NO: 65)) and of p15E (gp70)-specific CD8$^+$ T cells. A statistically significant increase in numbers of SIINFEKL-specific CTL cells were found in mice following transduced T-cell transfer compared CTL specific for control peptide (13+/−3 vs 1+/−0, p=0.008, FIG. 4D). We also detected a small, but statistically significant increase of p15E-specific CTL (3+/−1 vs 1+/−0, p=0.008, FIG. 4D). The resulting immunity was transferable as shown by tumor protection in 3 out of 9 mice adoptively transferred with splenocytes from cured mice and delay in tumor outgrowth, compared to none out of 3 mice transferred with naïve splenocytes (FIG. 4E).

3.6.6 Distribution of Adoptively Transferred T Cells in Tumor Bearing Mice

To differentiate whether the therapeutic efficacy of PTM fusion protein-transduced vs untransduced OT-1 T cells is due to the presence of the CD28 domain in the PTM fusion protein or merely to the expression of a non-signaling PD-1 on the T cell surface, we expressed a PD-1 deletion mutant, devoid of the intracellular portion of PD-1 (PD-1del, SEQ ID NOs: 57 (nucleic acid (cDNA)); 58 (protein)). Injection of PD-1del-transduced OT-1 T cells did not improve the therapeutic efficacy compared to untransduced OT-1 T cells in the Panc02-OVA model, in contrast to injection of PTM fusion protein-transduced OT-1 T cells (FIG. 5A). These results indicated dependency on the intracellular CD28 domain of the PTM fusion protein. We next investigated the fate of PTM fusion protein (SEQ ID NOs: 13 (nucleic acid (cDNA)); 14 (protein))-transduced versus untransduced OT-1 T cells in tumor bearing mice. PTM fusion protein-transduced T cells showed enrichment in Panc02-OVA tumors compared to untransduced T cells (59+/−2 vs. 49+/−1%, p=0.002). This effect was not observed in lymph nodes or in organs of non-tumor bearing mice (FIG. 5B). In addition, the PTM fusion protein-transduced OT-1 T cells produced statistically significantly more IFN-γ than untransduced OT-1 T cells in the tumor compared to other organs or to non-tumor bearing mice (1.5+/−0.2 vs 0.6+/−0.02 vs 0.9+/−0.03 ratio of PTM IFN-γ+ to untransduced IFN-γ+ T cells, p=0.002, FIG. 5C). Neutralization of IFN-γ in vivo almost completely abrogated the therapeutic impact of PTM-transduced OT-1 T cells, indicating the importance of this cytokine for the function of receptor (FIG. 7D). To further dissect the signaling motifs responsible for the accumulation of PTM fusion protein-transduced OT-1 T cells in the tumor, we used the PTM-FMNM (SEQ ID NOs: 51 (nucleic acid (cDNA)); 52 (protein)), PTM-AYAA (SEQ ID NOs: 53 (nucleic acid (cDNA)); 54 (protein)) and PTM-FMNM-AYAA (SEQ ID NOs: 55 (nucleic acid (cDNA)); 56 (protein)) mutant construct-transduced T cells described above to compare their fate to PTM fusion protein-transduced OT-1 T cells in tumor bearing animals. The T cell infiltration and persistence of PTM fusion protein-transduced T cells at the tumor site seem to be dependent on both YMNM (SEQ ID NO: 29) and PYAP (SEQ ID NO: 30) motifs, since T cells carrying the mutants were found in lower amounts compared to T cells carrying the wild type receptor (FIG. 5D). The increase in infiltrating PTM fusion protein-transduced OT-1 T cells shifted the ratio of infiltrating CD8$^+$ T cells to myeloid-derived suppressor cells (MDSC) in favor of the PTM fusion protein-transduced OT-1 T cells (0.7+/−0.1 vs. 0.1+/−0.03, p<0.001, PTM-CD8$^+$ T cells to MDSC ratio, FIG. 5E). A similar effect was observed for the ratio of CD8$^+$ T cells to regulatory T cells (FIG. 7E). Together, these findings indicate that adoptive transfer of PTM fusion protein-transduced T cells tipped the balance from immunosuppression towards productive immunity.

EXAMPLE 4: GENERATION OF A PD-1-CD28 RECEPTOR WITH HUMAN SEQUENCE (SEQ ID NOS: 23 (NUCLEIC ACID (CDNA) AND 24 (PROTEIN))

In line with the method as described in above Example 1.1, the human homologue PD-1-CD28 fusion protein was generated and cloned into the pMP71-vector after NotI and EcoRI digestion and ligation. The resulting human PD-1-transmembrane fusion protein (hPTM (SEQ ID NOs: 23 (nucleic acid (cDNA)) and 24 (protein)) consists of the PD-1 extracellular (Uniprot Entry No.: Q15116 (accession number with the entry version number 138 and version 3 of the sequence), AA 1-170; SEQ ID NOs: 17 (nucleic acid (cDNA)) and 18 (protein)), the human PD-1-transmembrane sequence (Uniprot Entry No.: Q15116 (accession number with the entry version number 138 and version 3 of the sequence), AA 171-191, SEQ ID NOs: 19 (nucleic acid) and 20 (protein)) and the human CD28 intracellular region (Uniprot Entry No.: P10747 (accession number with the entry version: 164 and version 1 of the sequence), AA 180-220, SEQ ID NOs: 21 (nucleic acid (cDNA)) and 22 (protein)).

4.1 Functionality of the Human PD-1-CD28 Fusion Protein (SEQ ID NOs: 23 (Nucleic Acid (cDNA)) and 24 (Protein)) in Human T Cells Primary human T cells were transduced with the human PD-1-CD28 fusion protein (hPTM, SEQ ID NOs: 23 (cDNA) and 24 (protein)) and stimulated with anti-CD3 antibody, alone or in combination with anti-CD28 antibody or with recombinant PD-L1 (R&D, Catalogue no.: 156-B7-100). Simultaneous stimulation of T cells with anti-CD3 antibody and PD-L1 lead to significantly increased induction of IFN-γ in transduced T cells, but not in untransduced T cells, compared to anti-CD3 antibody-stimulated cells. This demonstrates the functionality and stimulation advantage of T cells transduced with the human PD-1-CD28-fusion protein.

EXAMPLE 5: TRANSDUCTION OF T-CELLS AND CYTOTOXIC KILLING ASSAYS

Select experiments of Example 3 were repeated using a sorted CD4+ T cell population and/or the tumor cell line, EG7-PD-L1. The materials and methods for these experiments were identical to those outlined in Examples 2 and 3 with the exceptions indicated below.

5.1 Cell Lines

The murine pancreatic cancer cell line Panc02 and its ovalbumin-transfected counterpart Panc02-OVA were as described in section 2.1, above.

The tumor cell line EG7-PD-L1 was based on cell line EL4. The tumor cell line EL4 was created via lymphoma-induction in a C57BL mouse by 9,10-dimethyl-1,2-benzanthracene. Electroporation based transfection with the pAc-neo-OVA plasmid, carrying a copy of chicken ovalbumin (OVA) mRNA and a neomycin (G418) resistance gene, lead to the establishment of the EL4 derivate E.G7-OVA (Moore M W et al., Cell 54; 777-785, 1988). EG7-OVA-PDL1 was then generated by retroviral transduction with pMX-s (Kitamura et al., Exp. Hematol. 31 (2003), 1007-1014) containing full length murine PD-L1 SEQ ID NOs: 29 (nucleic acid (cDNA)) and 30 (protein) and by subsequent FACS-based cell sort for PD-L1 positive cells (anti-PD-L1, APC, clone 10F.9G2, BioLegend). EG7-PD-L1 tumor cells were cultured in RPMI 1640 with 10% FBS, 1% PS and 1% L-glutamine, 1% sodium pyruvate, 1 mM HEPES and 50 μM β-mercaptoethanol were added to the T cell medium.

5.2 Animals

Mice transgenic for a CD8+ T cell receptor specific for ovalbumin (OT-1) and for a CD4+ T cell receptor specific for ovalbumin (OT2) were obtained from the Jackson Laboratory, USA, and were bred in our animal facility under specific-pathogen free (SPF) conditions. Wild type C57BL/6 mice were purchased from Janvier, France.

5.3 CD4+ T-Cell Sorting and Transduction

The retroviral vector pMP71 (Schambach et al., Mol Ther 2(5) (2000), 435-45; EP-B1 0 955 374) was used for transfection of the ecotrophic packaging cell line Plat-E (Platinum-E). Transduction was performed according to the method described by Leisegang et al., J Mol Med 86 (2008), 573-83; Mueller et al., J Virol. 86 (2012), 10866-10869; Kobold et al., J Natl Cancer Inst (2014), in press. In brief, packaging cell line Plat-E (as described by Morita et al., Gene Ther 7 (2000), 1063-6) was seeded in 6-well plates and grown over night to 70-80% confluence. On day one, 18 gg of DNA were mixed together with 100 mM $CaCl_2$ (Merck, Germany). Plat-E cells were incubated for 6 h with the precipitated DNA. Medium was then removed and exchanged with culture medium. On day two, primary splenocytes were harvested from C57Bl/6 mice (Harlan Laboratories, The Netherlands) and sorted for CD4+ T cells with a MACS CD4+ (L3T4) T cell isolation kit (Miltenyi Biotec, Germany). The CD4+ T cells were stimulated with anti-CD3 (clone 145-2c11 BD Pharmingen, USA), anti-CD28 (clone 37.51, BD Pharmingen, USA), recombinant murine IL-2 (Peprotech, Germany) and 50 μM β-Mercaptoethanol in T cell medium over night. On day three, 24-well plates were coated with 12.5 μg/ml recombinant retronectin (Takara Biotech, Japan) for 2 h at room temperature, blocked with 2% bovine serum albumin (Roth, Germany) for 30 min at 37° C. and washed with PBS. Virus-containing supernatant from Plat-E cultures was harvested and passed through a filter (45 μm, Millipore, USA). Fresh T cell medium was then added to Plat-E cells. One ml of filtered supernatant was distributed in each well of the 24 well plates and spinoculated for 2 h at 4° C. Supernatant was then removed from the 24-well plate. $1 \times 10^6$ T cells were seeded in one ml T cell medium supplemented with 100 U IL-2 and 400,000 anti-mouse CD3 and anti-mouse CD28 beads (Invitrogen, Germany) per well and spinoculated at 800×g for 30 min at 32° C. On day four, Platinum-E supernatant was again harvested and filtered. One ml of the filtered supernatant was added to each well of the 24-well plate and spinoculated at 800×g for 90 min at 32° C. Cells were subsequently incubated for 6 hours at 37° C. Subsequently, cells were harvested, counted and reseeded at $1 \times 10^6$ cells/ml density in T cell medium supplemented with 10 ng IL-15 per ml (Peprotech, Germany) and 50 μM β-Mercaptoethanol. T cells were kept at this density until day 10 when cell analysis or functional assays were performed.

5.4 Functional T Cell Assays

For antibody-based stimulation assays, 96 well plates were prepared by coating with PBS (vehicle solution) containing murine anti-CD3 antibody (100 ng/ml, clone 145-2C11, eBioscience) alone or in combination with either anti-CD28 antibody (2 μg/ml, clone 37.51, eBioscience) or recombinant PD-L1 Fc chimera (5 μg/ml, R&D Systems) for 12 hours at 4° C. Wells containing only PBS were also prepared as controls. Subsequently, 300,000 T cells per well added and incubated for 36 hours. Cells were counted by addition of counting beads (Life Technologies, Germany; catalogue number: C36950) and subsequent proliferation, viability and phenotype analysis by flow cytometry (as described below). Cytokines were quantified in supernatants by ELISA (for IL-2 and IFN-γ, both BD according to manufacturer's instructions).

For T cell proliferation and phenotype analysis in tumor cell co-culture experiments, transduced or untransduced CD8+ and/or CD4+ T cells were stimulated in a 96-well plate previously coated with murine anti-CD3e antibody and recombinant murine PD-L1 as described above at 0.3×

$10^6$ cells per well (for isolated CD4+ cells, $0.15 \times 10^6$ cells per well) for 36 hours (end of stimulation was timepoint 1). Four hours prior to the end of stimulation $0.030 \times 10^6$ PancOVA tumor cells per well (in the experiments with isolated CD4+ cells, $0.04 \times 10^6$ PancOVA cells per well) were seeded in a new 96 well plate. At the end of the 36 hour stimulation, two thirds of the volume a well containing the pre-stimulated T cells was added to a well containing the target tumor cells and co-cultured for further 12 hours (timepoint 2). Cells were counted by addition of counting beads (Life Technologies, Germany). T cell phenotypes (CD62L, CCR7) and activation markers (CD69, PD-1) were determined by flow cytometry (as described below) at timepoints 1 and 2.

For in vitro killing assays, transduced or untransduced, CD8+ and/or CD4+ T cells per well were stimulated for 36 hours as described above with anti-CD3e antibody and recombinant PD-L1 Fc chimera. Four hours prior to the end of stimulation tumor cells were seeded in a 96-well plate as described above. The exact number of tumor cells depended on the tumor cells applied: $0.03-0.040 \times 10^6$ PancOVA, and $0.02 \times 10^6$ EG7-PD-L1. Following stimulation, two thirds of the volume of a well containing the pre-stimulated of T cells was added to a well containing the target tumor cells. Co-cultures ran from 8 to 18 hours, depending on the tumor cells applied (8 hours for PancOVA tumor cells, 18 hours for EG7-PDL1). Then, the supernatant was collected and T cell killing capacity was analyzed using LDH-based cytotoxicity assay (Promega, US) or murine Granzyme B ELISA (R&D Systems, US). IFN-γ levels in supernatants were quantified by ELISA (IFN-γ, BD).

For in vivo experiments, 200,000 EG7-PD-L1 cells were subcutaneously injected per mouse. When tumors were palpable, $10 \times 10^6$ PTM transduced T cells or untransduced OT-1 per mouse were intravenously injected via the tail vein. Tumor size was measured every 2-3 days, and mice were sacrificed when tumors had reached a maximal size of 225 mm². Cured mice and control animals were re-challenged with 30,000 tumor cells (per mouse, again subcutaneously injected) 30 days after tumor rejection.

5.5 Flow Cytometry

Multi-color flow cytometry was performed using a BD FACS Canto II (BD bioscience, Germany), and used the following antibody panels.

For antibody-based stimulation assays, cells were stained with Fixable Viability Dye (AmCyan, BioLegend), anti-mouse CD4 (PacBlue, clone GK1.5, BioLegend) and anti-mouse PD-1 (APC clone 29F.1A12, Biolegend). Cells were subsequently fixated and pernieabilized. After intracellular staining with anti-Ki67 (PE, clone 16A8, Biolegend) and anti-EOMES (PeCy7, clone Danl lmag, eBioscience), cells were washed and re-suspended in PBS containing Count Bright Absolute Counting Beads (Life Technologies, US). Alternatively, anti-IL17 (FITC, clone TC11-18H10.1, BioLegend) and anti-FoxP3 (PE, clone 150D, BioLegend) were included in the intracellular staining process for the differentiation of specific T cell subsets.

For phenotyping experiments, cells were stained with Fixable Viability Dye (AmCyan, BioLegend), anti-mouse CD8a (APCCy7, clone 53-6.7, BioLegend), anti-mouse CD4 (PE, clone GK1.5, BioLegend), anti-mouse CD62L (PacBlue, clone MEL-14, BioLegend), anti-mouse CCR7 (PerCP/Cy5.5, clone 4B12, BioLegend), anti-mouse CD69 (PeCy7, clone H1.2F3, BioLegend) and anti-mouse PD-1 (APC clone 29F.1A12, Biolegend).

5.6 Results 5.6.1 Functional and Phenotypic Analysis of Transduced CD4+ T Cells In Vitro To test the functionality of the murine PD-1-transmembrane PD-1-CD28-fusion protein (PTM, SEQ ID NOs: 13 (cDNA) and 14 (protein)), primary murine CD4+ T cells were transduced and stimulated with agonistic anti-CD3 antibodies or agonistic anti-CD3 antibodies in combination with either recombinant PD-L1 (SEQ ID NOs: 29 and 30) or anti-CD28 antibodies. PTM-transduced CD4+ T cells showed markedly increased IFN-γ (19998 vs 291 pg/ml, $p<0.001$, FIG. 9A) as compared to untransduced CD4+ T cells. Activation of the PTM receptor resulted in statistically significant improvements of proliferation and viability relative to controls (for proliferation: 151 vs 68 cells per bead (anti-CD3 antibody and recombinant PD-L1 vs. anti-CD3 antibody, respectively), $p<0.001$ FIG. 9B; and for viability: 60% vs 40%, (anti-CD3 antibody and recombinant PD-L1 vs. anti-CD3 antibody, respectively), $p<0.001$, FIG. 9C). This increase in cell number was associated with strong ki67 and eosmesdermin/Tbr2 (EOMES) upregulation, indicating strong mitotic activity and enhanced transcription/pronounced state of activation (FIGS. 9D and 9E, respectively).

The activation of the PTM receptor was also not associated with any increase in IL-17 or FoxP3 production. The expression of IL-17 and FoxP3 in PTM transduced CD4+ T cells was similar to that in control cells (FIGS. 10A and 10B, respectively), indicating that activation of the PTM receptor does not result in a phenotypic shift towards either a Th17 or Treg cell subtype within the T helper cell population.

Co-culture of pre-stimulated PTM-transduced T cells with PancOVA cells resulted in a decreased percentage of effector and an increased percentage of central memory T cells for both CD8+(FIGS. 11A and 11B) and CD4+ populations (FIGS. 11C and 11D). These results may also partially explain the favorable activity of the PTM transduced T cells in vivo, as central memory T cells have been described as having improved anti-tumoral effector activity relative to effector memory T cells. Expression of the early activation marker CD69 decreased during co-culture for both PTM-transduced or untransduced CD4+ and CD8+ T cells (FIGS. 11E and 11F), while expression of the late activation marker PD1 increased (FIG. 11G).

5.6.2 Therapeutic Efficacy of PD-1-CD28 Fusion Protein-Transduced T Cells in a Murine Pancreatic Cancer Model PD-1-CD28 (PTM; SEQ ID NOs: 13 (nucleic acid (cDNA)); 14 (protein)) protein-transduced antigen-specific T cells (OT-1 T cells as described in Examples 2 and 3), were used to treat mice bearing subcutaneous EG7-PD-L1 tumors. Similar tumor bearing mice treated with PBS or untransduced untransduced OT-1 T cells served as controls. PTM receptor-transduced T cells also induced superior anti-tumor immunity in this model as compared to control mice (FIG. 12A) significantly improving survival (p=0.03; FIG. 12B). When rechallenged with EG7-PD-L1 cells, mice previously treated with PTM transduced had been effectively cured, and remained tumor free in comparison to control, naïve mice (FIG. 12C).

The invention claimed is:

1. A lentiviral vector engineered to bring about expression of a mRNA transcript in a transduced human CD4+ or CD8+ T-cell via a constitutive promoter, wherein the mRNA transcript encodes two in frame fusion proteins separated by a self-cleaving peptide sequence; wherein one of the two fusion proteins comprises:
   i) a human PD-1 polypeptide that comprises:
      a) a PD-1 extracellular domain, comprising an amino acid sequence having PD-L1 binding activity, and
      b) a PD-1 transmembrane domain, consisting of the amino acid sequence as set forth in SEQ ID NO: 20; and
   ii) an intracellular domain of a CD28 polypeptide, consisting of the amino acid sequence as set forth in SEQ ID NO: 22,
   wherein the PD-1 transmembrane domain is fused via its C-terminus to the CD28 polypeptide; and
   wherein the other of the two fusion proteins confers anti-tumoral specificity to the transduced T-cell.

2. The lentiviral vector of claim 1, wherein the other of the two fusion proteins is a selected from the group consisting of: a chimeric antigen receptor, an alpha/beta T cell receptor, a natural T cell receptor, an anti-CD3 T cell engager, and a T-cell receptor (TCR) fusion protein (TFP).

3. A transduced human CD4+ or CD8+ T-cell comprising the lentiviral vector of claim 1, and wherein the cell expresses the two fusion proteins encoded by the mRNA transcript.

4. A method for the production of a transduced human CD4+ or CD8+ T-cell expressing two fusion proteins encoded by the mRNA transcript of claim 1 comprising the following steps:
   (a) transducing a T-cell with the lentiviral vector engineered to bring about expression of the mRNA transcript encoding the fusion proteins;
   (b) culturing the transduced cell under conditions allowing the expression of the fusion proteins in or on said transduced cell; and
   (c) recovering the transduced cell from the culture.

5. A transduced human CD4+ or CD8+ T-cell obtained by the method of claim 4.

6. A pharmaceutical composition comprising a transduced human CD4+ or CD8+ T-cell comprising the lentiviral vector of claim 1, wherein the cell expresses the two fusion proteins encoded by the mRNA transcript.

7. A transduced human CD4+ or CD8+ T-cell comprising the lentiviral vector of claim 1, wherein the cell expresses the two fusion proteins encoded by the mRNA transcript, and wherein the other of the two fusion proteins confers anti-tumoral specificity for a tumor antigen associated with lung cancer, ovarian cancer, melanoma, colon cancer, gastric cancer, renal cell carcinoma, esophageal carcinoma, glioma, urothelial cancer, retinoblastoma, breast cancer, Non-Hodgkin lymphoma, pancreatic carcinoma, Hodgkin's lymphoma, myeloma, hepatocellular carcinoma, leukemia, cervical carcinoma, cholangiocarcinoma, oral cancer, head and neck cancer, or mesothelioma.

8. A kit comprising a container housing the lentiviral vector of claim 1.

9. The lentiviral vector of claim 1, wherein the human PD-1 polypeptide comprises the sequence of SEQ ID NO: 16 or a sequence which has 1 to 10 substitutions, deletions or insertions in comparison to SEQ ID NO: 16 and which is characterized by having a PD-L1 binding activity.

10. A nucleic acid molecule encoding a fusion protein, that consists of SEQ ID NO: 24.

11. The lentiviral vector of claim 1, wherein the one of the two fusion proteins comprises a PD-1 polypeptide comprising a sequence which has 1 to 10 substitutions, deletions or insertions in comparison to SEQ ID NO:18 and which is characterized by having a PD-L1 binding activity.

* * * * *